(12) United States Patent
Vukasinovic

(10) Patent No.: US 9,701,938 B2
(45) Date of Patent: Jul. 11, 2017

(54) INTRA-CULTURE PERFUSION METHODS AND APPLICATIONS THEREOF

(71) Applicant: Jelena Vukasinovic, Atlanta, GA (US)

(72) Inventor: Jelena Vukasinovic, Atlanta, GA (US)

(73) Assignee: Lena Biosciences, Inc., Atlanta, GA (US)

( * ) Notice: Subject to any disclaimer, the term of this patent is extended or adjusted under 35 U.S.C. 154(b) by 371 days.

(21) Appl. No.: 14/050,619

(22) Filed: Oct. 10, 2013

(65) Prior Publication Data

US 2014/0106452 A1 Apr. 17, 2014

Related U.S. Application Data

(60) Provisional application No. 61/712,943, filed on Oct. 12, 2012.

(51) Int. Cl.
*C12N 5/00* (2006.01)

(52) U.S. Cl.
CPC ........ *C12N 5/0068* (2013.01); *C12N 2533/30* (2013.01); *Y10T 29/49826* (2015.01)

(58) Field of Classification Search
CPC ........................................................ C12N 5/00
See application file for complete search history.

(56) References Cited

U.S. PATENT DOCUMENTS

| | | | |
|---|---|---|---|
| 5,266,476 A | 11/1993 | Sussman et al. | |
| 6,471,993 B1 | 10/2002 | Shastri et al. | |
| 7,767,446 B2 | 8/2010 | Robbins et al. | |
| 2004/0071960 A1* | 4/2004 | Weber | C03C 17/001 428/336 |
| 2004/0209360 A1* | 10/2004 | Keith | C12N 5/0068 435/404 |
| 2008/0009027 A1* | 1/2008 | Fraker | C12M 23/04 435/29 |
| 2009/0209035 A1* | 8/2009 | Watanabe | A61F 2/062 435/395 |

OTHER PUBLICATIONS

Comley, D.J., 2010. 3D cell culture easier said than done. Drug Discovery World. 11(3): 25-41.
Cullen, D. K., Vukasinovic, J., Glezer, A., LaPlaca M.C. 2007. Microfluidic engineered high cell density three-dimensional neural cultures. J Neural Eng 4(2):159-172.
Fait, E., Malkusch, W., Gnoth, S.-H. et al. 1998. Microvascular patterns of the human large intestine: morphometric studies of vascular parameters in corrosion casts. Scanning Microscopy 12(4):641-651.
Fissell, W.H, Hofmann, C.L., Ferrell, N. et al. 2009. Solute partitioning and filtration by extracellular matrices. Am J Physiol Renal Physiol 297(4):F1092-F1100.
Marasanapalle, V., Li, X., Polin, L., et al. 2006. Novel in vitro model barriers for evaluation of the permeability of antitumor compounds, thioxanthones. Invest New Drugs 24(2):111-116.
Martini, J. and Honig, C.R. 1969. Direct measurement of intercapillary distance in beating rat in situ under various conditions of O2 supply. Microvasc Res. 1(3):244-256.
McCarty, W.J. and Johnson, M. 2007. The hydraulic conductivity of matrigel. Biorheology 44(5-6):303-317.
Rambani, K., Vukasinovic, J., Glezer, A. et al. 2009. Culturing thick brain slices: an interstitial 3D microperfusion system for enhanced viability. J Neurosci Methods 180(2):243-254.
Spencer, B.J. and Verma, I.M. 2007. Targeted delivery of proteins across the blood-brain barrier. Proc Natl Acad Sci U S A. 104(18):7594-7599.
Swartz, M. A., and Fleury, M.E. 2007. Interstitial flow and its effects in soft tissues. Annu. Rev. Biomed. Eng. 9: 229-256.
Sailon, A. M., Allori, A. C., Davidson, E. H., Reformat, D. D., Allen, R. J., & Warren, S. M. (2009). A novel flow-perfusion bioreactor supports 3D dynamic cell culture. BioMed Research International, 2009.
Deepa et al., Compositions of Perineuronal Net Extracellular Matrix in Rat Brain, Journal of Biological Chemistry, vol. 281, No. 26, pp. 17789-17800 (2006).
Hench, The Story of Bioglass, J Mater Sci: Mater Med, 2006, V17, p. 967-978.
Iida, Matrigel Invasion Assays, online publication at http://www.iprotocol.com (2004).
Nazhat et al. Controlled Microchannelling in Dense Collagen Scaffolds by Soluble Phosphates Glass Fibers. Biomacromolecules, v8, p. 543-551.
Nguyen et al., Characterization of Type I and IV Collagens by Raman Microspectroscopy: Identification of Spectral Markers of the Dermo-Epidermal Junction, Spectroscopy: An International Journal, vol. 27, Issue 5-6, pp. 421-427.
Sigma, "ECM gel from Engelbreth-Holm-Swarm mouse sarcoma", ProductInformation, Catalog No. E1270, Published Oct. 2006.
Sykova et al., Diffusion in Brain Extracellular Space, Physiol. Rev., vol. 88, pp. 1277-1340 (2008).
Karageorgiou, V. & Kaplan, D. (2005). Porosity of 3D biomaterial scaffolds and osteogenesis. Biomaterials. 26: 5474-5491.
Liu, X. et al. (2009). Bioactive borosilicate glass scaffolds: improvement on strength of glass-based scaffolds for tissue engineering. Journal of Materials Science: Materials in Medicine. 20: 365-372.
Howe, C.L. (2006). Coated glass and vicryl microfibers as artificial axons. Cells Tissues Organs. 183: 180-194.
Oh, S.H. et al. (2003). Fabrication and characterization of hydrophilic poly(lactic-co-glycolic acid)/poly(vinyl alcohol) blend cell scaffolds by melt-molding particulate-leaching method. Biomaterials. 24: 4011-4021.
Delong, S.A. et al. (2005). Covalently immobilized gradients of bFGF on hydrogel scaffolds for directed cell migration. Biomaterials. 26: 3227-3234.

(Continued)

*Primary Examiner* — Ruth Davis
(74) *Attorney, Agent, or Firm* — Meunier Carlin & Curfman LLC

(57) ABSTRACT

Disclosed are intra-culture perfusion methods applied to standard cell culture disposables using three-dimensional cell culture scaffold and synthetic vasculature compositions in high-throughput screening and high-content screening applications, and assay development.

21 Claims, 32 Drawing Sheets

(56) References Cited

OTHER PUBLICATIONS

Singh, M. et al. (2008). Strategies and applications for incorporating physical and chemical signal gradients in tissue engineering. Tissue Engineering: Part B. 14(4): 341-366.

Tanriverdi, S. et al. (2007). Electrospinning and characterization of alumina borosilicate ceramic nanofibres. Materials Science-Poland. 25(4): 957-968.

* cited by examiner

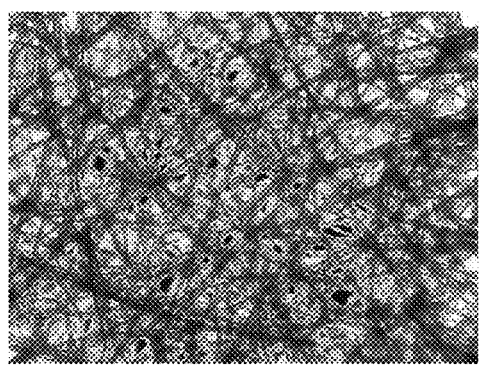
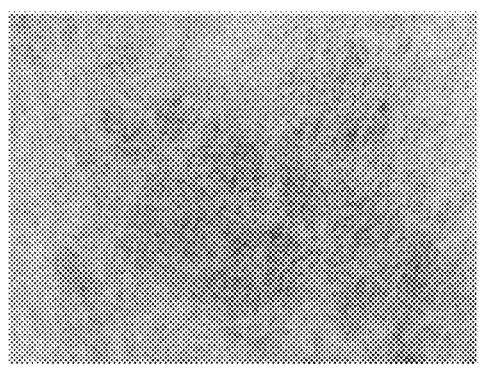
FIG. 2A                FIG. 2B
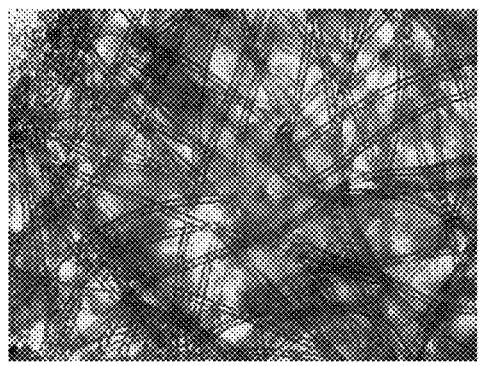
FIG. 2C                FIG. 2D

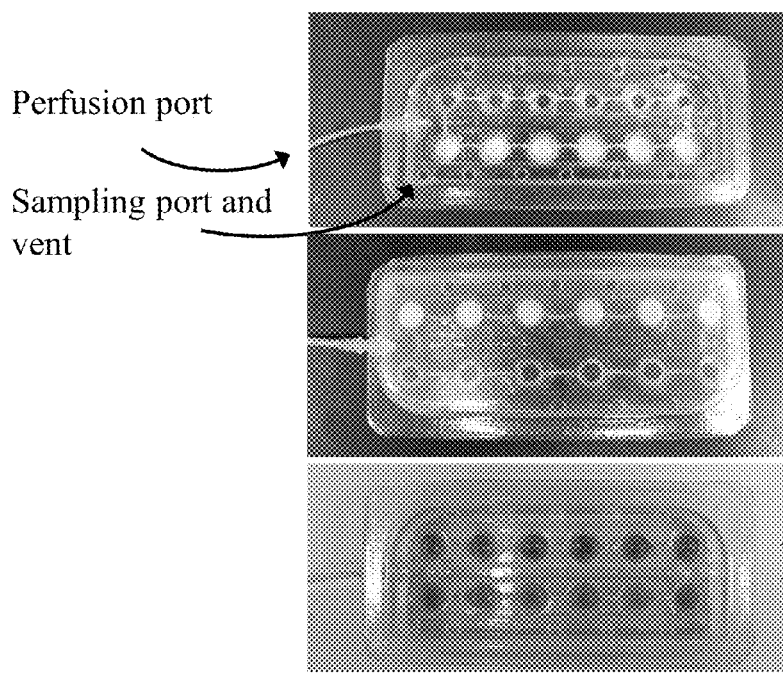

Hydrophilic, rigid and absorbent material

Hydrophilic, rigid and absorbent scaffold-vasculature
+
MATRIGELTM extracellular matrix + Cells Pump: peristaltic pump Pump: push/pull syringe pump with 2 syringes

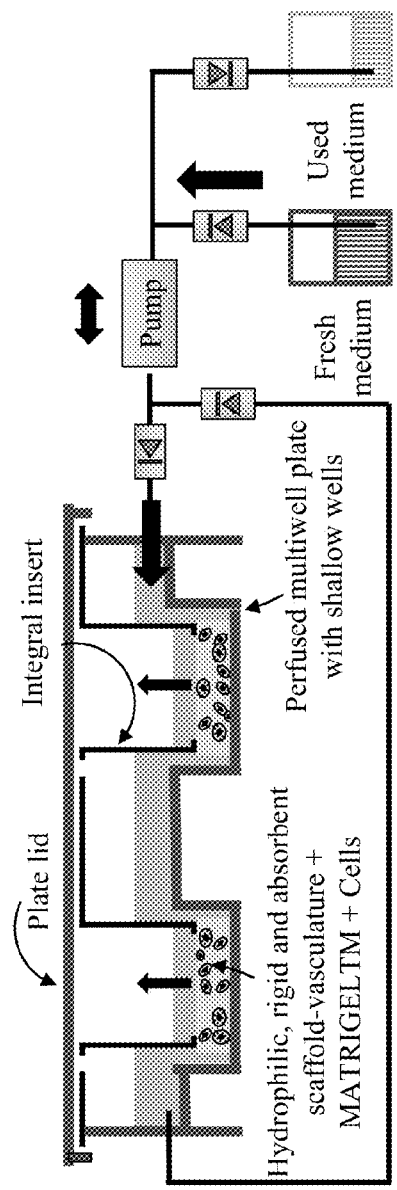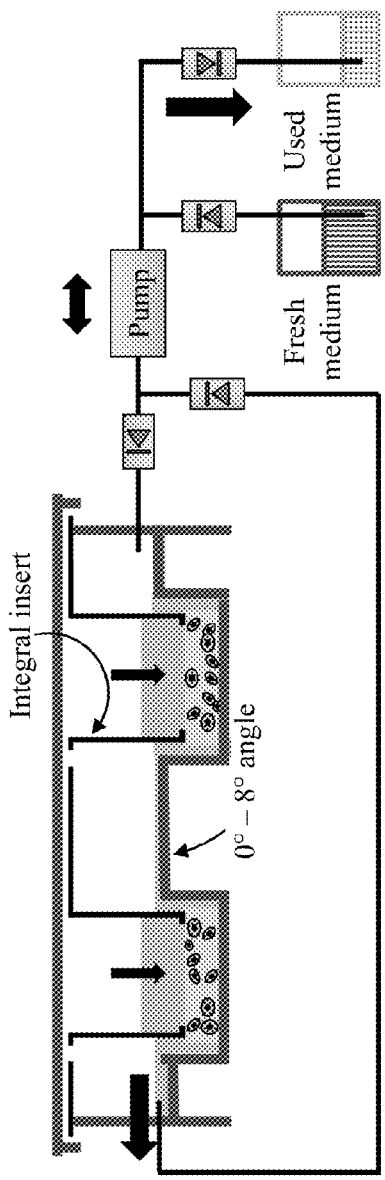

48-well plate for assaying

Air vent | Integral insert seated into a server insert | Lid

Server insert

Hydrophilic scaffold-vasculature + Cells (+ Optional ECM gel) | Multiwell plate with shallow wells and a reservoir above the wells

INTRA-CULTURE PERFUSION METHODS AND APPLICATIONS THEREOF

CROSS REFERENCE TO RELATED APPLICATIONS

This application claims the priority benefit of U.S. Provisional Patent Application Ser. No. 61/712,943 filed on Oct. 12, 2012.

STATEMENT REGARDING FEDERALLY SPONSORED RESEARCH OR DEVELOPMENT

This invention was made with government support under 1 R43 NS065543 and 5 R43 NS065543 awarded by the National Institutes of Health. The U.S. government has certain rights in this invention.

BACKGROUND OF THE INVENTION

To reduce high attrition rates and accelerate discovery and development timelines, the pharmaceutical industry seeks in vitro alternatives to interrogate drug candidates prior to animal, humanized animal, and human studies. Enormous cost, ethical concerns and increased pressure from regulatory agencies all drive demand for cell-based models and perfusion methodologies that can be used for in vitro screening of both large and small molecule drugs, and to triage toxic and ineffective leads earlier, prior to in vivo studies. However, it has been difficult finding a cell-based model that mimics function of living tissues, and a corresponding perfusion system which mimics both the function of vasculature and in vivo tissue perfusion for physiologically closer tissue modeling, tissue metabolic sustenance, and the delivery, distribution and testing of compounds within the interior of tissue mimicking cell mass.

Recently, three-dimensional (3D) cell cultures have emerged as an alternative to screening in a flat layer of cells as means to model tissues with improved physiological relevance for biomedical research and in vitro drug testing of all stages. 3D cultures are cellular networks organized in three dimensions—an environment that is much more similar to that found in vivo. Examples include 3D cell cultures grown in extracellular matrix (ECM) gels or gels mimicking the ECM; 3D cell aggregates such as tumor spheroids, embryoid bodies and hanging drop cell cultures; and cultures grown in 3D rigid scaffolds, among others.

For most drug screening applications, mature, tissue-like 3D cell cultures with well developed cell networks, cell-cell and cell-ECM signaling and interactions are needed. However, it has been challenging to grow and maintain such cultures due to diffusive mass transport limitations within their interior, and especially in the case of a common 3D ECM gel culture model or a high-cell-density spheroid model. Accordingly, without functional vasculature and non-invasive yet efficient intra-3D-culture perfusion, it has been difficult to deliver and distribute nutrients, drugs and other compounds intra-3D-culture for physiologically closer tissue modeling and drug testing in the same. The latter is especially true for large molecule drugs (e.g. monoclonal antibodies, therapeutic proteins, tissue growth factors, etc.) and drugs which mass transport in vivo relies on convection.

In standard, diffusion-limited culturing systems in vitro, 3D cultures which model tissues perfused in vivo suffer from the same problems as do slices of said explanted tissue. Tissues and tissue-like 3D gel cultures pose high resistance to mass transport due to steric hindrance and ionic interactions between solutes and ECM gel constituents. This reduces molecular diffusivities by approximately 18% to 93% from free solution values [Swartz, M. A., and Fleury, M. E. 2007. Annu Rev. Biomed. Eng. 9: 229-256]. From the 3D culture periphery to its interior, intra-culture availability of nutrients and gas reduces and metabolic waste accumulates, leading to formation of a necrotic, inner core. Accordingly, in mature 3D cultures, the necrosis and inconsistent decay that progresses culture-to-culture calls into question the reproducibility of cell outcomes and interpretation of screening results (cultures decay before studies are completed, adhere poorly, begin to float, or are simply aspirated during media exchanges in standard protocols).

Prior art 3D cell culture perfusion tools have also been riddled with problems. Lack of intra-culture perfusion methods (intra-gel or through a dense mass of cells); cumbersome priming and out-gassing; pressure surges and clogging of miniaturized components, complex setup, frequent user interventions in operation with overall poor culture performance relative to user input and cost have been some of the problems even when throughput was low. In part, this is because these tools were originally developed for perfusion of cell monolayer cultures, and then applied with little modification to perfusion of 3D cultures. For example, in a two-dimensional (2D) cell culture having one layer of cells, gel is typically absent. However, perfusion intra-gel is necessary if cells are to be perfused in a 3D gel cell culture plug.

Since prior art flow geometry has rarely been optimized for intra-3D-culture perfusion forcing flow around 3D culture rarely made flow of concentrated solutions pass intra-3D-culture (due to higher culture resistance), and the dominant mode of intra-3D-culture mass transport has remained diffusion-limited. The common prior art "superfusion" approach succeeded mainly to efficiently mix, stir or otherwise maintain high nutrient and gas concentration in the medium that surrounds the culture. Accordingly, forcing flow intra-culture (e.g. 3D cell culture gel plug) and forcing it non-invasively has remained a delicate task.

Another frequently overlooked problem in prior art cell culture perfusion, whether with 2D cultures or 3D cultures, is that the vast majority of perfusion tools have been based on unidirectional perfusion. In this perfusion setting, signaling molecules cells secrete to regulate their environment, growth and many other functions have been constantly washed away with the one-way flow. This is of concern because trophic factors, autocrine and paracrine signaling molecules cell secrete, need, and are surrounded by, are critical for sustained 3D cell culture growth, function, and drug testing. Although medium recycling has been used to mitigate this effect, relatively high liquid volume to culture volume in a single loop have generally contributed to dilution and delay in bringing these molecules back to cells.

Each of these issues likely contributes to the findings of the Comley article [Comley, D. J., 2010. Drug Discovery World. 11(3): 25-41] relating to the lack of adequate perfusion methods and tools to support 3D cell cultures in high-throughput screening and high-content screening applications. Specifically, in discussing state of the art in 3D cell culture perfusion tools the Comley article stated "Currently they are optimised to quite specific 3D applications (e.g. invasion assay profiling) or to support specific tumour cell models."

Accordingly, what is needed in the art are methods and tools dedicated to 3D cell culture perfusion, to force flow intra-cultures non-invasively and without abrupt fluctuations; with delivery and distribution of nutrients, gas, and test compounds within the 3D cultures in a manner analogous to the in vivo situation at a minimal loss of cell secreted molecules; and in high-throughput. More specifically, what is needed are (A) materials which mimic function of in vivo vasculature to efficiently deliver and distribute agents to the interior of tissue mimetic cultures in high-throughput; materials which mimic the function of vasculature in unperfused cultures under hydrostatic and osmotic pressure differences; materials which mimic the function of vasculature in forced convection intra-culture perfusion; (B) methods of making synthetic vasculature and methods of controlling the synthetic vasculature volume fraction in a 3D culture volume, capillary diameters and inter-capillary distances; methods of using said vasculature to vascularize cell cultures and to deliver and distribute soluble factors and gas; (C) perfusion methods and tools to non-invasively deliver and distribute agents intra-culture without abrupt fluctuations in culturing conditions, and without prohibitively high shear and normal stresses causing cellular injuries; perfusion tools and methods which prevent loss of cell signaling molecules while removing waste products; perfusion tools and methods that enable easy plating of cultures, minimize paths of low resistance around the cultures, and evacuate air in high-throughput manner; and (D) methods of making and using perfusion platforms and their integrative platform variations (which meet A-C) in a high-throughput format for ease of automation and user adoption.

SUMMARY OF THE INVENTION

The present invention answers the need for a perfusion system that provides for routine and automated culturing of three-dimensional (3D) cell cultures, and routine dug delivery and distribution within the interior of said cultures by way of intra-culture perfusion method.

The present invention further answers the need to vascularize 3D cell cultures, and discloses materials and methods of making and using synthetic intra-culture vasculature in conjunction with a scaffold and the intra-culture perfusion method, wherein the vasculature poses lower resistance to flow than do other extracellular components of the culture, whether soft or rigid.

The present invention furthermore answers the need for a perfusion tool which incorporates an intra-culture perfusion method, a scaffold, and a synthetic vasculature to deliver nutrients, dissolved gas and test compounds within the interior of 3D cultures analogous to in vivo situation.

The invention discloses materials and methods of making and using 3D cell culture perfusion tool comprising perfused compartment(s), and one or more hydrophilic component(s) into which cells or cells in a sol-state gel are seeded. In one embodiment, the hydrophilic component is the rigid scaffold. In another embodiment the hydrophilic component comprises the rigid scaffold and vasculature.

The invention further discloses a perfusion method which limits loss of cell signaling molecules, and provides for a design solution to evacuate air in the domain outside of the culture(s) following culture plating, prior to and during perfusion.

The invention also answers the need for a perfusion tool which incorporates (1) an intra-culture perfusion method, wherein said method also limits loss of cell signaling molecules, and further enables air evacuation in the domain outside of cultures(s); and (2) the rigid scaffold and/or the synthetic vasculature to deliver nutrients, dissolved gas and test compounds within the interior of 3D cultures consistently, reproducibly, and in high-throughput.

The invention also discloses methods and design solutions to integrate the above into a kit of cell culture disposables suitable for routine, high-throughput 3D culture plating, culturing, perfusion, assaying, high-throughput screening, high-content screening and pharmacological profiling.

BRIEF DESCRIPTION OF THE DRAWINGS

FIG. 2 contains photographs of hydrophilic and absorbent materials. FIG. 2A shows Pall conjugate pad type 8301, stained with a brown dye, followed by a 30-minute room temperature drying at 4× in bright field (x=2.45 mm, y=1.84 mm). FIG. 2B and FIG. 2C show Cerex Advanced Fabrics SpectraMax® in 24 g/m$^2$ and 68 g/m$^2$ fabric weight, respectively. FIG. 2D is a photograph of SpectraMax® (68 g/m$^2$ fabric) at 10× in bright field (x=980 μm, y=735 μm) after staining with brown dye solution in DI water, followed by a 30-minute drying. Absorbent content, whether the fiber or the fiber coating was stained and appears dark in FIG. 2A and FIG. 2D.

FIG. 3A shows the 24-well insert after 45-minute Matrigel gelation in the incubator. FIG. 3B shows a 24-well plate with Methylene Blue solution. FIG. 3C shows the 24-well insert seated into the 24-well plate for the vascular permeability assay. The insert wells had no liquid (other than that bound by the gel, where applicable). FIG. 3D shows the 24-well insert after 2-minute sitting in the 24-well plate with Methylene Blue solutions. FIG. 3E shows the insert which was further subjected to 3 minute immersion in Methylene Blue solutions with DI water added to the insert to equilibrate the pressure. FIG. 3F shows the insert further subjected to 3 minute immersion in Methylene Blue solutions and then flipped upside down for imaging.

FIG. 4 comprises photographs of a 12-well insert system used in perfused vasculature permeability assay (FIGS. 4A-4C) and schematic drawings of the experimental setup used in said assay (FIGS. 4D-4E). The top and bottom view of the insert are shown in FIGS. 4A-4B. FIG. 4A shows that the top row wells were blind and that the bottom row wells had a built-in hydrophilic and absorbent non gel-based scaffold-vasculature. FIG. 4C shows the top view of the insert after plating and gelation of 16 mg/ml MATRIGEL™ delivered to each insert well. FIG. 4D shows MATRIGEL delivery into the wells.

FIG. 4E shows the injection of the Methylene Blue with the corresponding rise in liquid level in the reservoir.

In FIGS. 5A-5G the perfusion rate was 100 µl/min. In FIGS. 5H-5N the flow rate was 200 µl/min. In FIG. 5O the perfusion was stopped.

FIGS. 6A-6E show mass transport in MATRIGEL™ top-row control wells and in MATRIGEL™ embedded in hydrophilic and absorbent scaffold-vasculature in bottom-row wells during perfusion. FIGS. 6F-6G show the 12-insert after perfusion was stopped. MATRIGEL™ controls were poorly stained by the Methylene Blue drug and had no liquid above the gel; MATRIGEL™ acted as a plug during perfusion. MATRIGEL™ in scaffold/vasculature was completely stained and had the liquid above the gel; it allowed flow to pass. FIGS. 6H-6I, taken at the end of experiment, show MATRIGEL™ controls in the reservoir and the MATRIGEL™ embedded in the scaffold-vasculature in the insert wells, respectively.

FIG. 7 contains 3D renderings of fluorescently labeled MATRIGEL™ 3D cell culture surrogates after 2 days in unperfused FIGS. 7A-7C, and perfused condition FIGS. 7D-7F. FIGS. 7D-7F show that perfused MATRIGEL™ eroded at the bottom where the flow entered into it. The 3D renderings of confocal z-stacks comprise a series of images which were taken approximately every 20 µm in the z-direction through the full gel thickness in a field of view close to the center of the well. The stacks were taken at 10× (x=898.24 µm, y=898.24 µm) using Zeiss LSM 510 confocal microscope with two-channel excitation for the Calcein and Rhodamine gel staining to get a strong signal through the thick gel.

FIG. 8 contains schematic drawings of the experimental arrangement used in the perfusion flow permeability assay in a cross section view comprising one of each, a well with the non-gel hydrophilic scaffold-vasculature and a blind well (FIGS. 8A-8B), and an image sequence showing the assay (FIG. 8C-8I).

FIG. 11 contains 2 schematic drawings depicting bi-directional cell culture perfusion arrangement using a custom 12-well integral insert system comprising an anchoring, hydrophilic and absorbent scaffold-vasculature.

FIG. 12 contains z-stacked confocal micrographs showing live cells intracellularly labeled green by Calcein AM and dead cell nuclei labeled red by EthD-1.

FIG. 13 contains z-stacked confocal micrographs of the Calcein AM (green) labeled live cells and EthD-1 (red) labeled dead cell nuclei.

FIG. 14 contains z-stacked confocal micrographs of a live/dead cell assay Calcein AM/EthD-1 for two representative 7-day perfused 3D cultures cultured in the uncoated- (FIG. 14A and FIG. 14C) and PDL-coated (FIG. 14B and FIG. 14C) rigid and absorbent synthetic 3D scaffold-vasculature.

Figure 15A:
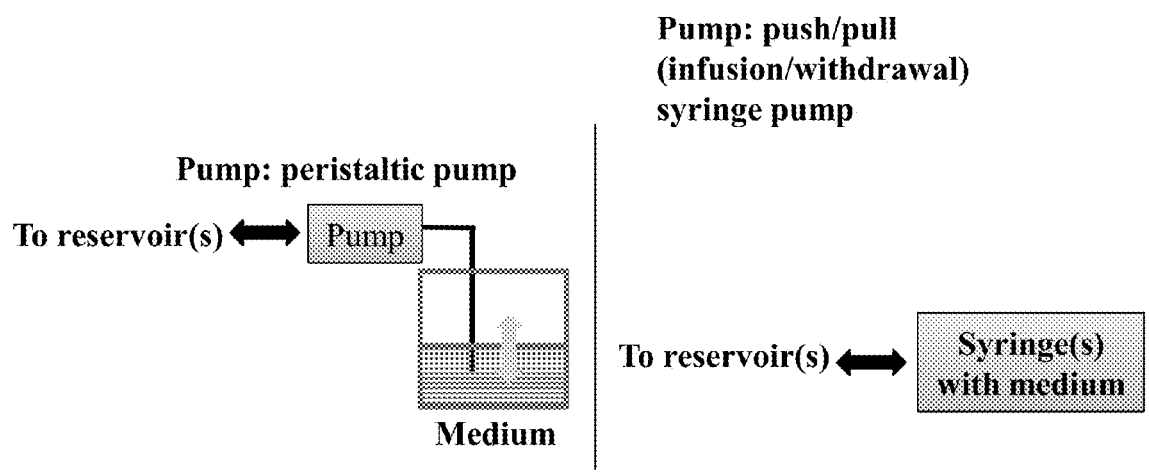
Figure 15B:
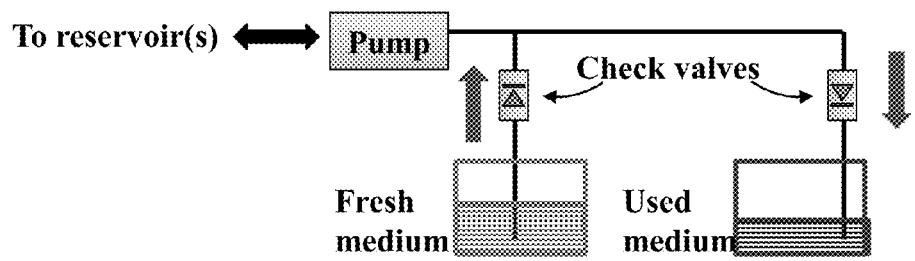
Figure 15B:
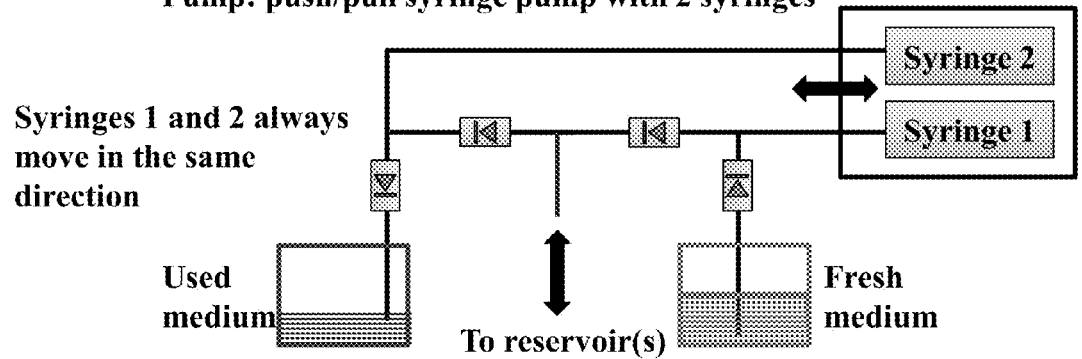

FIG. 15 is a schematic drawing of the perfusion system for bi-directional intra-culture perfusion with one fluidic port disposed in the reservoir. FIG. 15A (left) shows medium recycling mode of operation using a peristaltic pump which cyclically pumped the medium in and out of the reservoir. FIG. 15A (right) shows medium recycling mode of operation setup via a syringe pump operated in a continuous push/pull infusion/withdrawal mode so as to cycle the medium in and out of the reservoir. FIG. 15B shows cyclic infusion of fresh medium into the reservoir during infusion stroke and withdrawal of used medium from the reservoir during withdrawal stroke. FIG. 15B (top) shows a peristaltic pump which cyclically infused fresh and withdrew used medium from the reservoir by way of two check valves and two medium bottles, one of each for fresh and used medium, respectively. FIG. 15B (bottom) shows a syringe pump which cyclically infused fresh medium and withdrew used medium from the reservoir by way of four check valves and two medium bottles, one of each for fresh, and used medium, respectively.

Figure 16A:
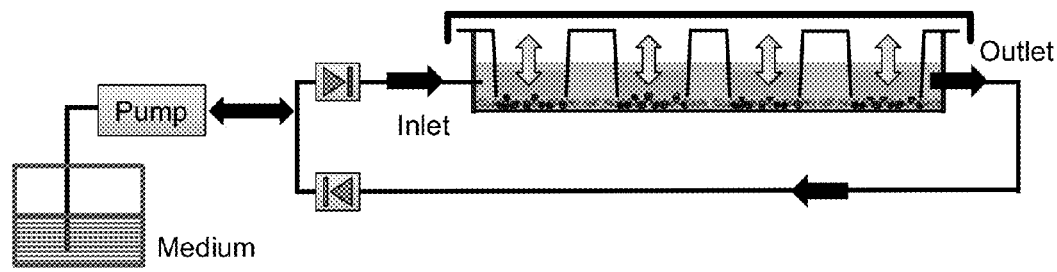
Figure 16B:
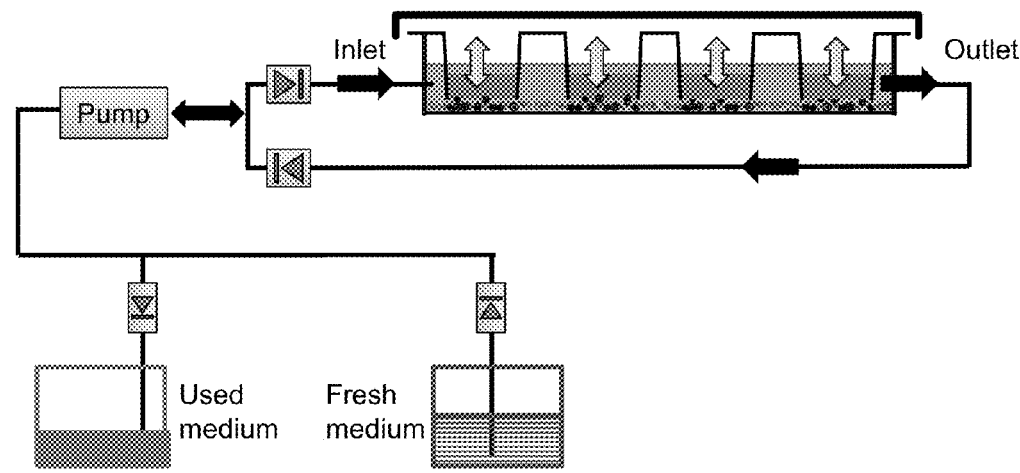

FIG. 16 is a schematic drawing of the perfusion system for bi-directional intra-culture perfusion with two fluidic ports disposed in the opposing sides of the reservoir for unidirectional flow through the reservoir. FIG. 16A depicts a configuration in which the medium is recycled using a peristaltic pump and a pair of check valves (one-way flow through the reservoir; intra-culture perfusion mode: bi-directional with medium recycling). FIG. 16B shows a configuration in which fresh medium is delivered into the reservoir using medium from the fresh medium bottle during infusion stroke, and the used medium is withdrawn from the reservoir and dispensed into the used medium bottle during withdrawal stroke (one-way flow through the reservoir—fresh medium infused/used medium withdrawn; intra-culture perfusion mode: bi-directional).

Figure 17C:
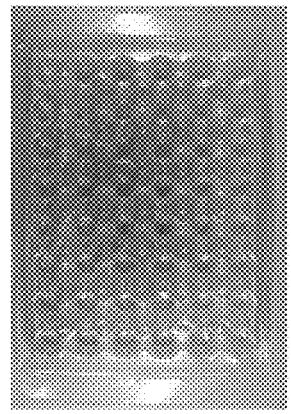
Figure 17D:
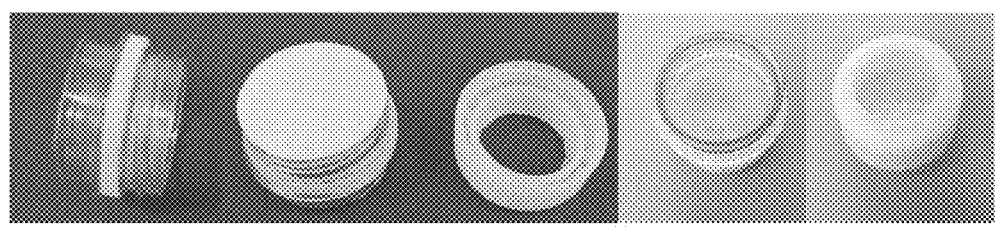
Figure 17E:

FIG. 17 contains images of a flow design and the multi-well insert system tool which provided for no cross-talk between cultures during perfusion. FIGS. 17A-17B are schematic drawings of the bi-directional cell culture perfusion in a uni-directionally perfused system, wherein the cultures were perfused in parallel and sequestered during culturing. The key component of the system was a perfused 48-multiwell plate comprising shallow wells (seating the respective insert wells) and a reservoir above the said wells with one-way flow through the reservoir. FIG. 17A shows the custom multiwell insert system, the operation of external fluidic architecture during infusion stroke, and the flow through the reservoir and the flow intra-culture. FIG. 17B shows the same during the withdrawal stroke. FIG. 17C is a photograph of the custom 48-well plate with shallow wells and a reservoir above the wells. FIGS. 17D-17E show threaded and snap-fit attachment of the porous materials to the insert wells, respectively.

FIG. 18 contains a photograph and a schematic drawing of a thermoformed 48-well perfused insert system. FIG. 18A is a photograph of the custom 48-well well insert system (without the lid) as it was vacuum formed and after making the insert wells blind via a circular punch tool, exemplary feed tray comprising 8 reservoirs with interfaced fluidic ports, and a standard 48-well plate into which the insert comprising cultures was transferred to for assaying. The porous substrates built into the 48-well insert are not shown for clarity. FIGS. 18B-18C are schematic drawings demonstrating an exemplary use of the perfused 48-well insert system in the assay development. Depicted system comprised an integral insert, universal feed tray, multi-reservoir feed tray, a multiwell plate and a lid. In this exemplary arrangement, cells and matrix were seeded into the insert wells for automated perfusion feeding in a universal feed tray for 1-2 weeks until 3D cultures were matured enough for drug studies (FIG. 18B). Next, the insert was transferred into the 8-reservoir feed tray, and perfused with 8 different drugs or drug concentrations; one per reservoir (FIG. 18C). Next, the insert was transferred to a standard 48-well plate for assaying individual cultures (FIG. 18D).

Figure 19A:
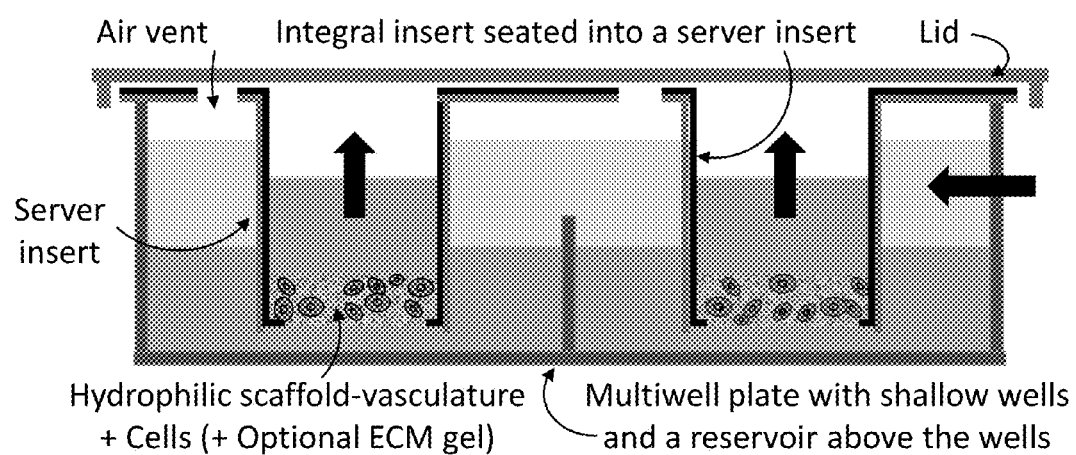
Figure 19B:
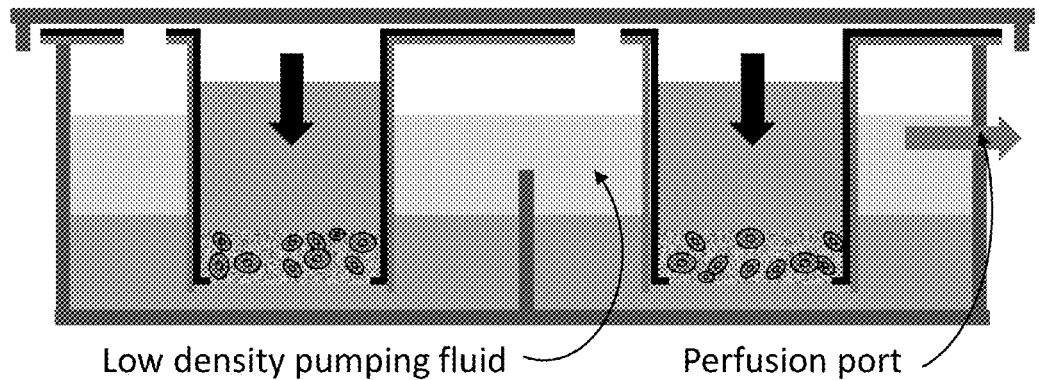
Figure 19C:
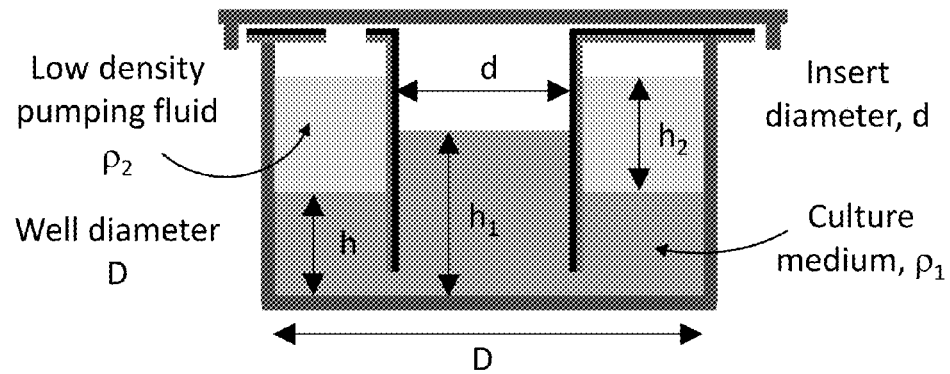

FIG. 19 shows schematic drawings of the perfusion arrangement used for sequestered bi-directional 3D cell culture perfusion via the density gradient perfusion method wherein the pumping liquid was the liquid of a lower density than that of the culture medium, immiscible or substantially immiscible in culture media and aqueous solutions, and non cyto-toxic. FIGS. 19A-19B show the infusion and withdrawal stroke, respectively, assuming infinitesimally small density difference between the pumping liquid and the culture medium. FIG. 19C shows liquid-to-liquid and liquid-to-air interfaces under hydrostatic equilibrium without the cultures.

Figure 20A:
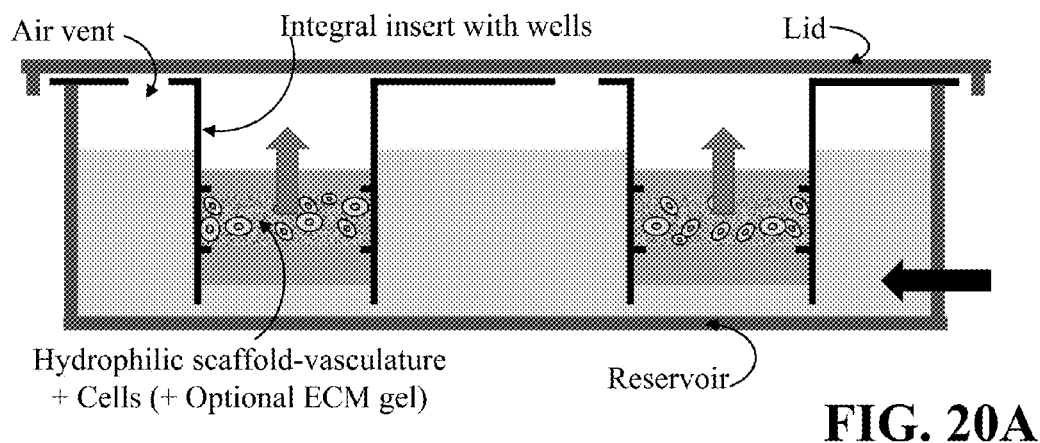
Figure 20B:
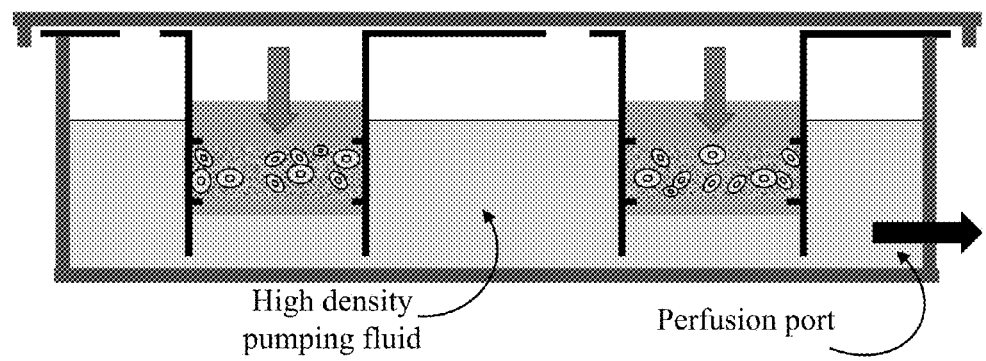
Figure 20C:
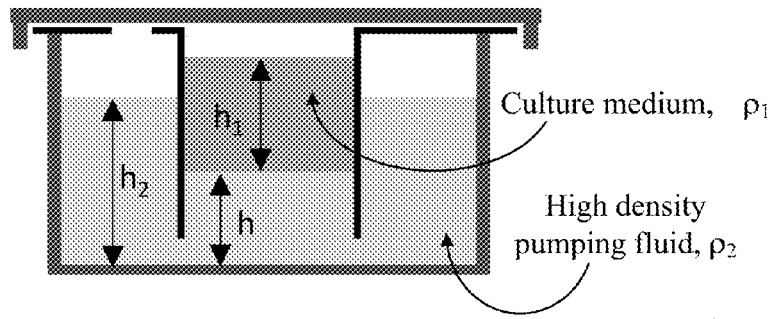

FIG. 20 shows schematic drawings of the perfusion arrangement used for sequestered bi-directional 3D cell culture perfusion via the density gradient perfusion method wherein the pumping liquid was the liquid of a higher density than that of the culture medium, immiscible or substantially immiscible in culture media and aqueous solutions, and non cyto-toxic. FIGS. 20A-20B show the infusion and withdrawal stroke, respectively, assuming infinitesimally small density difference between the pumping liquid and the culture medium. FIG. 20C shows liquid-to-liquid and liquid-to-air interfaces under hydrostatic equilibrium without the cultures.

Figure 21:
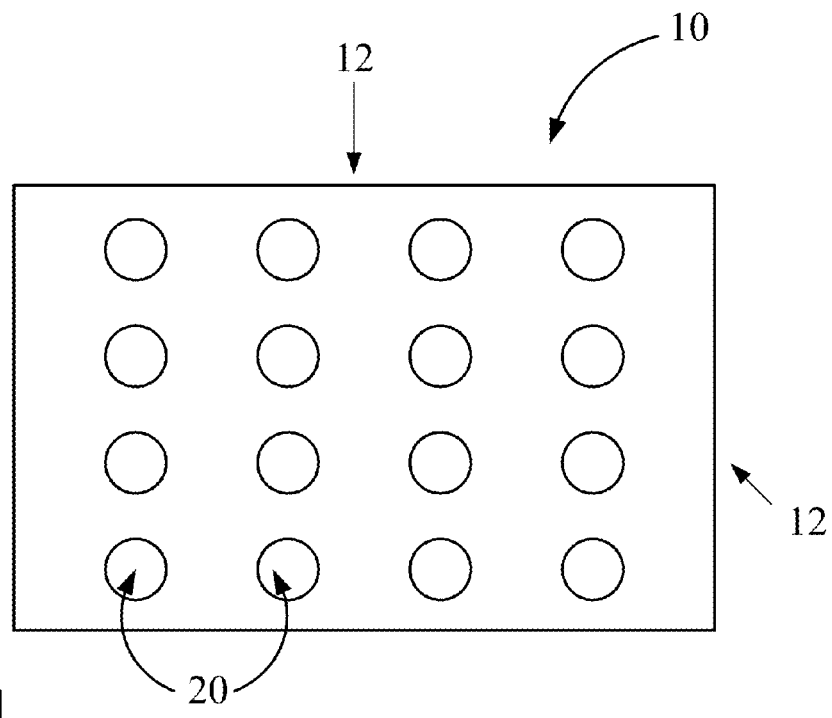

FIG. 21 is a top plan view of one embodiment of a plate for use in culturing cells according to the present invention.

Figure 22:
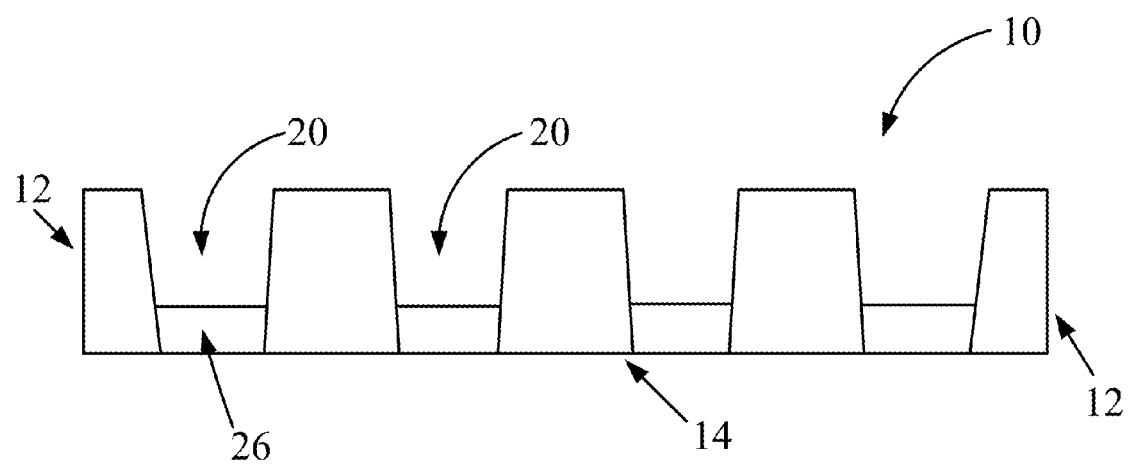

FIG. 22 is a side plan view of one embodiment of a plate for use in culturing cells as shown in FIG. 21.

Figure 23:
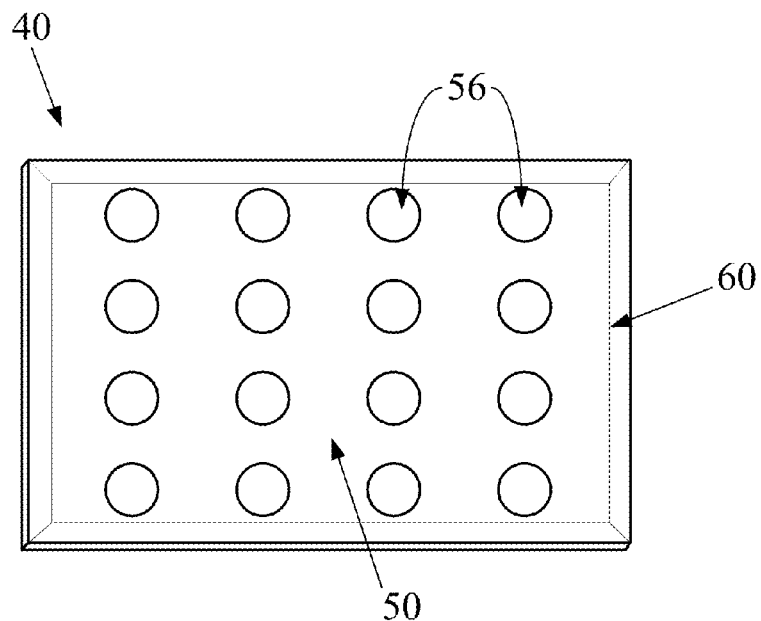

FIG. 23 is a perspective view of one embodiment of a housing for use in culturing cells according to the present invention.

Figure 24:
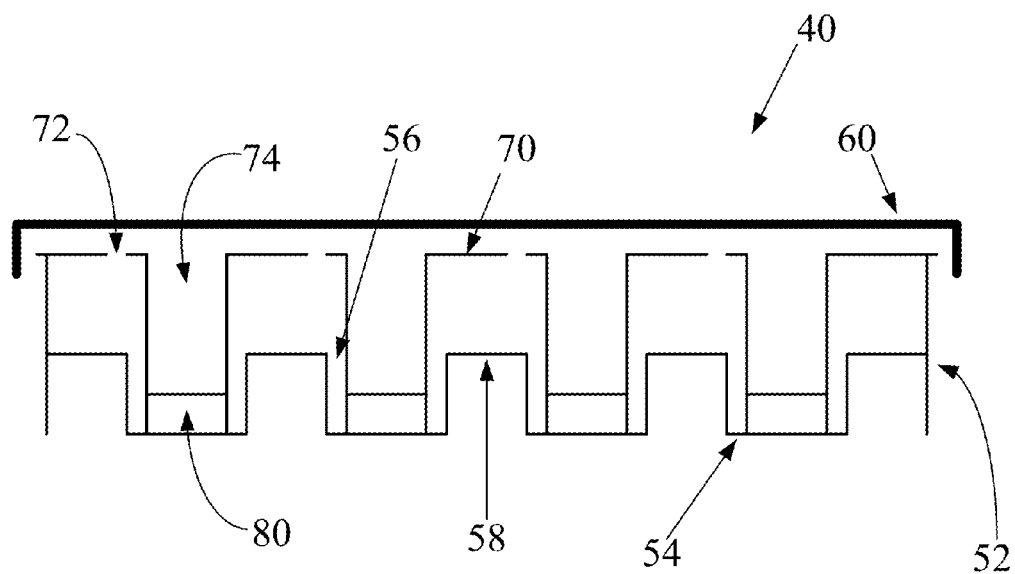

FIG. 24 is a side plan view of one embodiment of a housing for use in culturing cells as shown in FIG. 23.

Figure 25:
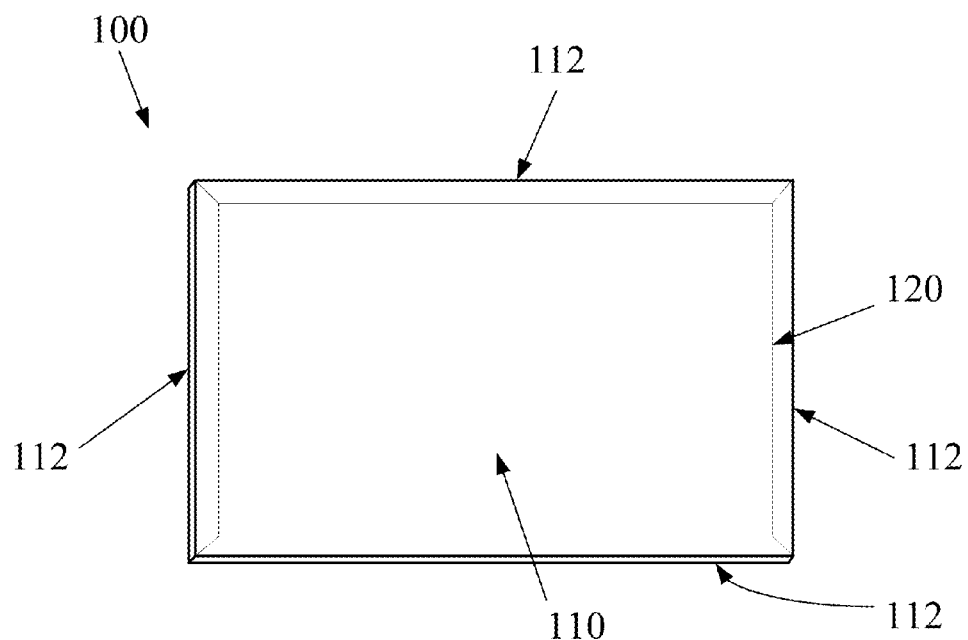

FIG. 25 is a perspective view of one embodiment of a housing for use in culturing cells according to the present invention.

Figure 26:
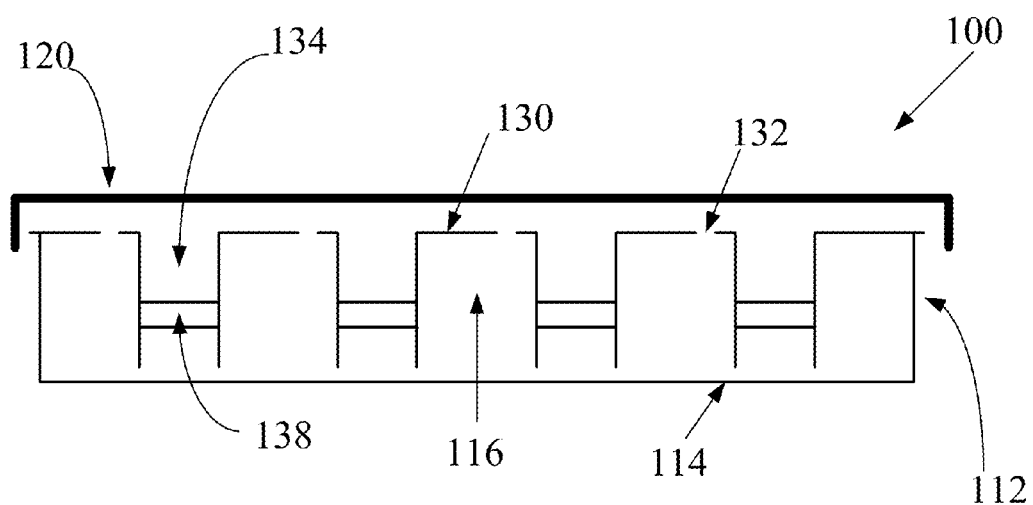

FIG. 26 is a side plan view of one embodiment of a housing for use in culturing cells as shown in FIG. 25.

DETAILED DESCRIPTION OF THE INVENTION

Described herein is a rigid three-dimensional, cell culture scaffold composition. The scaffold composition is configured such that it has a dry-state, interior, nonrigid and non-absorbent volume (hereinafter referred to as a "void volume") of between approximately 60% and 95%. In some embodiments, this void volume of the scaffold composition comprises a gel and/or one or more cells.

The scaffold is a scaffold more rigid than a gel scaffold. The scaffold comprises a network of one or more 3D organized and connected hydrophilic fiber(s). Non-limiting examples of hydrophilic fibers are naturally hydrophilic fibers, fibers impregnated by a hydrophilic coating or otherwise rendered hydrophilic. Preferably, the fiber material has a water contact angle of less than 60°. The hydrophilic fiber is preferably between approximately 5 and 100 µm in diameter. The fibers are preferably insoluble and non-degradable. In one embodiment, hydrophilic fibers are transparent when immersed in cell culture solutions.

It is a surprising finding of the present invention that the above defined scaffold which comprises hydrophilic fibers forms intra-culture capillary voids which function as intra-culture vasculature in forced convection flow intra-culture, wherein the culture comprises gel with one or more cells embedded within the scaffold. As used herein, the term "intra-culture perfusion" describes perfusion methodology in which flow passes through the interior of the culture.

Also disclosed is a rigid 3D cell culture scaffold/synthetic vasculature composition comprising a 3D network of connected hydrophilic fibers, wherein at least one type of fiber is absorbent and/or comprises an absorbent coating. The absorbent component is hydraulically conductive so as to functions as synthetic intra-culture vasculature in intra-culture perfusion. In one embodiment, 3D scaffold/synthetic vasculature comprises a mixture of rigid, optically transparent hydrophilic staple fibers and optically transparent absorbent staple fibers, wherein absorbent fibers or fibers coated with an absorbent coating comprise a polymer network which swells when immersed in aqueous solutions. In some embodiments the absorbent staple fiber is a fibrillated fiber, wherein the fiber fibrillates into a network of many fibers. This combination of materials and compositions yields a scaffold suitable for routine 3D culture plating and handling, of significant fibrillation to better mimic the in vivo vasculature, and of excellent transparency for ease of intra-culture imaging.

In the present invention, 3D network of absorbent fibers and/or fibers impregnated by an absorbent coating extends to at least one surface bounding the culture embedded within and adhered to said scaffold. In a preferred embodiment, the 3D network of absorbent fibers and/or fibers impregnated by an absorbent coating extends to all surfaces bounding the culture embedded within and adhered to the scaffold, wherein the scaffold contains the culture and the culture comprises gel and one or more cells.

Disclosed is a method of using the scaffold and/or scaffold coating as intra-culture vasculature under suitable conditions. In some embodiments the entire scaffold and/or scaffold coating functions as synthetic intra-culture vasculature. In other embodiments a part of the scaffold and/or scaffold coating functions as synthetic intra-culture vasculature. Suitable conditions under which the intra-culture vasculature is functional are: (a) hydraulic resistance, or the resistance to fluid flow per unit area and per unit length of flow permeable fibers or their permeable coatings, is less and preferably very less than the same posed by the culture, wherein the culture comprises gel and one or more cells or 3D cell spheroids through which absorbent fibers or fibers comprising an absorbent coating pass; (b) intra-culture vasculature extends to at least one surface of the culture and preferably all; and (c) the magnitude of flow rate imposed through the culture does not generate prohibitively high normal and shear stresses to injure cells or disintegrate other present extracellular material.

Disclosed are also methods to synthetically vascularize 3D cell cultures by way of a controllable volume fraction of the synthetic vasculature in the overall scaffold composition. The coating of one or more fibers with an absorbent, hydrophilic coating, wherein the coated fiber(s) may be subsequently mixed with other hydrophilic but non-absorbent fibers in the process of making the scaffold and the synthetic vasculature is a method to control the amount of absorbent component and the vasculature volume fraction within the culture. The weight content of absorbent fibers in the final 3D fiber network composition is also a method to control the vasculature volume fraction in the final scaffold/synthetic vasculature composition. The combined weight content of absorbent fibers and/or absorbent coating on the coated fibers is yet another method to control the vasculature volume fraction in the final scaffold/synthetic vasculature composition.

Furthermore, disclosed are methods to control geometrical properties of synthetic vasculature by way of selecting, combining and mixing a controlled amount of the absorbent staple fibers or the fibers comprising an absorbent coating (in some embodiments with the other fibers). The diameter, length and 3D distribution of absorbent fibers and/or the absorbent coating on other fibers is a method to control geometrical properties of the synthetic vasculature to better mimic those in vascularized tissues in vivo. As shown in the U.S. Provisional Patent Application Ser. No. 61/712,943 and U.S. patent application Ser. No. 13/962,403 the production method used and production parameters used dictate external and internal scaffold dimensions, wherein fiber to fiber distances, porosity and tortuosity is adjusted by respective fiber percent weights in the slurry, total fiber weight in the suspension, the fiber dispersion and mixing method including any additives, the base area of the vessel containing the fiber suspension during settling, and pressure, vacuum and/or temperature during dispersion and/or drying and/or post-drying to control the scaffold thickness in an exemplary wet-laid production method. However, disclosed scaffold and/or synthetic vasculature compositions can be made by any method known to those of skill in the art that provides for a void volume of between approximately 60% and 95%.

The alteration of absorbent component composition and characteristic dimensions in the non-gel scaffold further provides for a method to control intra-culture delivery and distribution of molecules intra-culture even if the cultures are not perfused. When the absorbent component combined mass transport resistance to diffusion and osmosis is lower than that of the gel such as commonly used MATRIGEL™ extracellular matrix and/or cell layers, the absorbent component enables more efficient mass transport intra-culture. The lower the absorbent component resistance to said mass transport, the more uniform the agent delivery by way of synthetic vasculature within the interior of gel-based 3D cell cultures even without perfusion.

The alteration of hydraulically conductive absorbent component composition and characteristic dimensions in the non-gel scaffold is also a method to control intra-culture delivery and distribution of molecules intra-culture by way of convective flow of molecules due to both imposed pressure differences across the culture and osmotic pressure differences.

The synthetic vasculature comprising a part or the entire rigid scaffold, wherein the vasculature is permeable to either diffusive-, convective mass transport, or both and the scaffold holds gel and one or more cells within its void volume, distinguishes the present invention from all prior art three-dimensional cell culture compositions. Vascularized 3D cell cultures of the present invention are particularly advantageous for high-throughput screening, and even more advantageous for high-content screening of lead compounds in pre-clinical studies.

Disclosed intra-culture perfusion methods, wherein said perfusion takes place through the core of cells mass via synthetic vasculature and/or through a gel is advantageous for long-term maintenance of tissue mimetic cultures for drug screening in the same, and even more advantageous for high-throughput screening and high-content screening of larger molecule pharmaceuticals such as monoclonal antibodies, therapeutic proteins, cytokines, tissue growth factors etc.

Bi-directional intra-culture perfusion, cyclic forth-and-back perfusion, is a method to reduce loss of cell secreted signaling molecules, otherwise lost in one-way perfusion yet vital for normal cell- and culture growth and function. In a preferred embodiment, bi-directional perfusion cycles substantially the same medium through the culture in more than one forth-and-back cycle.

The methods of using bi-directional intra-culture perfusion in a standard format comprising a multiwell insert system wherein the insert system comprises hydrophilic scaffold or hydrophilic and absorbent scaffold functioning as intra-culture vasculature is a method to mirror the in vivo tissue perfusion and to deliver and distribute compounds intra-culture, and particularly large molecule compounds which efficacy, potency, and safety cannot be assessed in diffusion limited culturing conditions in vitro.

The invention also discloses how to make and use multiwell insert systems in intra-culture perfusion by way of communicating compartments which are fluidically connected through hydraulically conductive scaffold comprising cell culture; and how to fluidically interface these systems to perfuse a plurality of cultures, whether the medium is recycled or not. Furthermore, the invention discloses how to sequester cultures during perfusion. In one embodiment, a dimensional analysis is used to show that in a one-way flow through the reservoir, with bi-directional flow through the cultures, the rate of convection is still large enough even for a small molecule like glucose not to cross from one well to another. Next, it is disclosed that a superposition of unidirectional flow acting as a DC offset to alternating bi-directional flow through the cultures also prevents or eliminates well-to-well cross-talk without raising intra-culture flow velocities in a design solution in which the cultures only "feel" the bi-directional flow (as explained in Example 11). This provides for a method to sequester perfused cultures without complicated plumbing or miniature components prone to clogging and failure. Accordingly, disclosed is a flow configuration and a tool in which said flow configuration was used to sequester cultures. The perfusion tool comprised an integral insert with one or more wells, hydrophilic scaffold or hydrophilic and absorbent scaffold functioning as intra-culture vasculature seated into each insert well, and a perfused multiwell plate or a perfused reservoir seating the insert. The perfused multiwell plate or a perfused reservoir comprises 3 ports, 2 of which are disposed on the opposing sides of the reservoir to setup a constant one-way flow through the reservoir, and at least one port is used to setup bi-directional flow.

Also disclosed is a perfused multiwell insert system in which cultures are sequestered during bi-directional intra-culture perfusion using two fluidic ports (Example 11, FIGS. and 17A-17B). The system comprises a multiwell insert, wherein the insert comprises one or more wells; a perfused multiwell plate with one or more shallow wells, wherein the perfused multiwell plate comprises a shared reservoir above the wells; and a lid. Each insert well comprises hydrophilic scaffold or hydrophilic and absorbent scaffold functioning as intra-culture vasculature, and is seated into the shallow well such that the height of each well in the multiwell plate is above the top of the scaffold by at least 0.1 mm during perfusion. The bottom of the reservoir forms an angle in x-direction, y-direction, or both from the inlet disposed in one side of the reservoir to the outlet disposed on the other side of the reservoir, wherein the x-direction is aligned with a longer side of the reservoir, and the y direction is aligned with the shorter side of the reservoir, and the outlet is below the inlet in z-direction. The reservoir is fed by cyclic infusion of medium and withdrawal of the same. In an exemplary fluidic arrangement shown in FIGS. 17A-17B in Example 11, during infusion stroke fresh medium is infused from the side of the reservoir which bottom is at a higher elevation, and no fluid is drawn from the reservoir. During withdrawal stroke medium is withdrawn from the side of the reservoir which bottom is at a lower elevation, and no fluid is injected into the reservoir. This flow configuration with a one-way flow through the reservoir and bi-directional perfusion intra-culture, as well as the exemplary perfused multiwell insert system design provide for a "time lag" in well-to-well cross talk during filling such that no "information" from the downstream well (with respect to the direction of the one-way flow through the reservoir) can be carried upstream to the next well. This limits well-to-well cross-talk during reservoir filling, while all cultures are perfused equally driven by a fluid height difference between that in a well of the multiwell plate and that in the respective insert well. Essentially, this provides for a zero residence time of fluid passing over the upstream wells during filling until the level of liquid within the entire reservoir exceeds that within the insert. Further, during withdrawal, the inclination of the reservoir towards the exit facilitates draining without causing well-to-well cross-talk due to outgoing flow from respective wells in which the liquid level recedes. This particular design combined with dimensional analysis, is a method to control well-to-well cross-talk or to eradicate it. Finally, as each culture contains the same level of liquid in the respective plate well when the fluid from the reservoir is drained, this fluid is injected into the culture during the next infusion stroke; therefore, limiting the loss of culture signaling molecules, and ensuring consistent culture growth. As shown in Example 10, it is the lack of efficient intra-culture perfusion and not the lack of extra-culture nutrient availability which limits survival of tissue mimetic cultures, and the disclosed perfusion systems and methods of making and using the same efficiently address this problem which was poorly diagnosed in prior art.

Further, in Example 12 disclosed are methods of using liquids of different densities as pumping fluids for sequestered bi-directional culture perfusion in a multiwell insert system, and the methods of making, using and interfacing the same. In one embodiment, the density gradient perfusion uses a pumping liquid of lower density than that of the culture medium. In another embodiment, the pumping liquid has a higher density than that of the culture medium. In both embodiments, the insert system design and perfusion methodology ensure that each culture is perfused only by its own medium and the culture medium is immiscible with the non-toxic pumping liquid and stays separated from it during perfusion. In the first embodiment, the integral insert comprising the cultures is seated in a server insert and has no contact internal or external with the pumping liquid. In the second embodiment, the high-density pumping liquid is preferably a perfluorinated liquid such as Perfluorodecalin. These liquids are advantageous because of their high gas solubility which provides for improved gas exchange at the bottom side of the culture.

Disclosed multiwell insert systems, methods of making and using the same in bi-directional intra-culture perfusion provide for means to routinely culture a plurality of 3D cell cultures for the period of days and weeks, and to routinely deliver and distribute compounds intra-culture for pharmacological profiling in a high-throughput screening and high-content screening compliant format. The disclosed systems are advantageous as they do not require special skill to extract high-content information from information-rich consistent 3D cell cultures.

For all exemplary disclosed perfusion platforms, the disposables, i.e. the multiwell insert system disposables can be made using any method known in the art which provides for mono-well or multiwell configuration of any footprint or well arrangement in standard microtiter plate plastic materials. It is to be understood that fluidic ports can be disposed on any side of the reservoir; however, for practical purposes if the perfused system is to be imaged in situ in operation, the preferred location of the ports is on the sides of the reservoir which were closest to being vertical. The port openings could also be made by any method known in the art which provided for an opening, including piercing or puncturing the material.

It is to be understood that when scaffold/synthetic intra-culture vasculature is built-into the reservoir, the surface of the reservoir on which the scaffold/synthetic vasculature is attached or built into can be recessed down or protruded up from the interior surface of the reservoir base. It is also understood, that when the scaffold/synthetic intra-culture vasculature is built into the insert well, the distance between the bottom of the scaffold/synthetic vasculature from the interior surface of the reservoir under it is arbitrary for the perfusion system to function properly, so long as the cultures plated into the scaffold/synthetic intra-culture vasculature is at least 0.1 mm below the free surface of the medium within the insert well or the reservoir during perfusion.

It is to be understood that additional components can be added to the underside of the scaffold/synthetic intra-culture vasculature so long as these additional components do not hinder flow in bi-directional intra-culture perfusion if the insert is perfused.

Further provided herein, and as shown in at least FIGS. 21 and 22, is a plate 10 for use in cell culture experiments, comprising sides 12, a bottom 14, and a plurality of wells configured to contain a cell culture, each well 20 having an open top portion and a hydraulically conductive three dimensional scaffold 26 in an open bottom portion, the bottom portion allowing for fluid communication between adjacent wells when the plate 10 is filled with a fluid. In some embodiments, the plate 10 comprises 48 wells, however, it is to be understood that the present invention encompasses a plate 10 having more (i.e., 96 wells) or less wells (i.e., 24 wells). In some embodiments, the plate further comprises a lid.

In some embodiments, the hydraulically conductive three dimensional scaffold 26 contacts or sits on the plate bottom 14. As used herein, the term "hydraulically conductive" refers to a material that is hydrophilic and has interconnected pores. Various hydraulically conductive materials are described throughout the application. In some embodiments, the hydraulically conductive scaffold 26 comprises a non-gel hydrophilic porous material with a void volume of between approximately 60% and 95%. In some embodiments, the hydraulically conductive material has a lower hydraulic resistance than a gel such as MATRIGEL™.

In other or further embodiments, the hydraulically conductive scaffold 26 comprises an absorbent material as defined herein. The absorbent material may be evenly distributed throughout the scaffold or may be distributed in certain regions of the scaffold 26, which regions connect at least two sides of the scaffold 26. When the absorbent material is more hydraulically conductive than a gel material (i.e., a MATRIGEL™ material), the hydraulically conductive scaffold 26 comprising the absorbent material is referred to herein as a synthetic vasculature.

In some embodiments, the plate 10 further comprises at least one fluid port. A "fluid port" is defined herein as an opening that allows for the ingress (inlet) and/or egress (outlet) of a liquid from a structure such as a plate or housing. In one embodiment, the plate 10 comprises an inlet fluid port and an outlet fluid port disposed on opposite sides of the plate 10. These fluid ports can be removably coupled to a fluid pump and one or more fluid source units. For example, a fluid source unit is configured to be removably coupled to the fluid pump such that the fluid source unit may be reusable or disposable for fluid addition. Similarly, the plate 10 may be removably coupled to first a fluid pump unit such that a second, or different, fluid pump unit can replace the first to associate the cell cultures with different fluid/dynamic environments. In some embodiments, a peristaltic fluid pump is removably coupled to the plate 10.

The present invention further includes methods of using the plate 10 described herein. Provided herein is a method of using the plate 10, comprising 1) providing the plate 10, 2) adding one or more cells to one or more of the scaffolds 26 in the wells 20, 3) adding one or more liquids to the one or more wells 20, and 4) culturing the cells. The cells may be mixed with a gel prior to adding the cells to the one or more scaffolds 26. The gel can be any as described herein, and in one embodiment, the gel is a MATRIGEL™.

Also provided herein, and shown in at least FIGS. 23 and 24, is a housing 40 for use in cell culture experiments, comprising a plate 50, a lid 60, and a well insert 70, wherein 1) the plate comprises sides 52, a bottom 54, and a plurality of large wells configured to contain a cell culture, each large well 56 having a height lower than the plate sides 52, and 2) the well insert 70 comprises one or more air openings 72 and a plurality of small wells configured to contain a cell culture, wherein each small well 74 is smaller in width and depth and greater in height than the corresponding large well 56 that it fits within, wherein each small well 74 has an open top portion and a hydraulically conductive three dimensional scaffold 80 in between, and in one embodiment in a bottom portion. In some embodiments, the plate 50 comprises 48 wells, however, it is to be understood that the present invention encompasses a plate 50 having more (i.e., 96 wells) or less wells (i.e., 24 wells).

In some embodiments, the plate 50 further comprises at least one fluid port. In one embodiment, the plate 50 comprises an inlet fluid port and an outlet fluid port disposed on opposite sides of the plate 50. These fluid ports can be removably coupled to a fluid pump and one or more fluid source units. For example, a fluid source unit is configured to be removably coupled to the fluid pump such that the fluid source unit may be reusable or disposable for fluid addition. Similarly, the plate 50 may be removably coupled to first a fluid pump unit such that a second, or different, fluid pump unit can replace the first to associate the cell cultures with different fluid/dynamic environments. In some embodiments, a peristaltic fluid pump is removably coupled to the plate 50.

Further, in some embodiments, the plurality of large wells are separated by a substantially horizontal surface 58 disposed at the height of the large wells. The substantially horizontal surface 58 can have approximately no incline, or can be inclined in a single direction across the plate 50 between approximately 1 and 8 degrees.

The hydraulically conductive scaffold 80 of the small well 74 can be any described throughout the application. In some embodiments, the hydraulically conductive scaffold 80 comprises a non-gel hydrophilic porous material with a void volume of between approximately 60% and 95%. In some embodiments, the hydraulically conductive material has a lower hydraulic resistance than a gel such as MATRIGEL™.

In other or further embodiments, the hydraulically conductive scaffold 80 comprises an absorbent material as defined herein. The absorbent material may be evenly distributed throughout the scaffold or may be distributed in certain regions of the scaffold 80, which regions connect at least two sides of the scaffold 80. When the absorbent material is more hydraulically conductive than a gel material (i.e., a MATRIGEL™ material), the hydraulically conductive scaffold 80 comprising the absorbent material is referred to herein as a synthetic vasculature.

The present invention further includes methods of using the housing 40 described herein. Provided herein is a method of using the housing 40, comprising 1) providing the housing 40, 2) adding one or more cells to one or more of the scaffolds 80 in the small wells 74, 3) adding one or more liquids to the one or more small 74 and large 56 wells, and 4) culturing the cells. When two liquids are added to the small 74 and large 56 wells, the liquids may be immiscible and of a different density. In one embodiment, a fluid having a lower density than a culture medium is added to one or more small wells 74, and the culture medium is added to one or more large wells 56. In another embodiment, a culture medium is added to one or more small wells 74, and a fluid having a lower density than a culture medium is added to one or more large wells 56. The cells may be mixed with a gel prior to adding the cells to the one or more scaffolds 80. The gel can be any as described herein, and in one embodiment, the gel is a MATRIGEL™.

Also provided herein, and shown in at least FIGS. 25 and 26, is a housing 100 comprising a plate 110, a lid 120, and a well insert 130, wherein 1) the plate 110 comprises sides 112 and a bottom 114 which define a plate reservoir 116, 2) the well insert 130 comprises one or more air openings 132 and a plurality of wells configured to contain a cell culture, wherein each well 134 has an open top portion, an open bottom portion, and a hydraulically conductive three dimensional scaffold 138 disposed in between, and 3) the well insert 130 is disposed within the plate reservoir 116. In some embodiments, the plate 110 comprises 48 wells, however, it is to be understood that the present invention encompasses a plate 110 having more (i.e., 96 wells) or less wells (i.e., 24 wells).

In some embodiments, the plate 110 further comprises at least one fluid port. In one embodiment, the plate 110 comprises an inlet fluid port and an outlet fluid port disposed on opposite sides of the plate 110. These fluid ports can be removably coupled to a fluid pump and one or more fluid source units. For example, a fluid source unit is configured to be removably coupled to the fluid pump such that the fluid source unit may be reusable or disposable for fluid addition. Similarly, the plate 110 may be removably coupled to first a fluid pump unit such that a second, or different, fluid pump unit can replace the first to associate the cell cultures with different fluid/dynamic environments. In some embodiments, a peristaltic fluid pump is removably coupled to the plate 110.

The hydraulically conductive scaffold 138 of the well 134 can be any described throughout the application. In some embodiments, the hydraulically conductive scaffold 138 comprises a non-gel hydrophilic porous material with a void volume of between approximately 60% and 95%. In some embodiments, the hydraulically conductive material has a lower hydraulic resistance than a gel such as MATRIGEL™.

In other or further embodiments, the hydraulically conductive scaffold 138 comprises an absorbent material as defined herein. The absorbent material may be evenly distributed throughout the scaffold or may be distributed in certain regions of the scaffold 80, which regions connect at least two sides of the scaffold 138. When the absorbent material is more hydraulically conductive than a gel material (i.e., a MATRIGEL™ material), the hydraulically conductive scaffold 138 comprising the absorbent material is referred to herein as a synthetic vasculature.

The present invention further includes methods of using the housing 100 described herein. Provided herein is a method of using the housing 100, comprising 1) providing the housing 100, 2) adding one or more cells to one or more of the scaffolds 138 in the wells 134, 3) adding one or more liquids to the wells 134 and the plate reservoir 116, and 4) culturing the cells. When two liquids are added to the wells 134 and the plate reservoir 116, the liquids may be immiscible and of a different density. In one embodiment, a fluid having a higher density than a culture medium is added to the plate reservoir 116, and the culture medium is added to the wells 134. The cells may be mixed with a gel prior to adding the cells to the one or more scaffolds 80. The gel can be any as described herein, and in one embodiment, the gel is a MATRIGEL™.

It should be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

EXAMPLES

Example 1

The Anchoring (Hydrophilic, Absorbent) Scaffold Compositions Comprising Hydrophilic and Absorbent Synthetic Vasculature which Extended to all Exterior Surfaces of the Scaffold U.S. Provisional Patent Application Ser. No. 61/712,943 and the U.S. patent application Ser. No. 13/962,403 disclosed production methods and materials which were suitable examples of 3D scaffolds comprising absorbent synthetic vasculature, wherein the vasculature extended to all exterior surfaces of the scaffold. In one embodiment, the entire 3D scaffold was absorbent and made from PVOH fibers. In another embodiment, the scaffold was made of borosilicate glass fibers coated with the absorbent polyvinyl alcohol (PVOH). In a further embodiment, scaffold compositions comprising PVOH fibers and PVOH-coated borosilicate glass fibers were disclosed. In another embodiment, the scaffold was made using absorbent fibrillated cellulose fibers and PVOH-sized borosilicate glass fibers. In yet another embodiment, the scaffold was coated by an additional absorbent coating and/or the percent weight of the absorbent component in the scaffold composition altered by subsequent treatments and/or sterilization methods.

Next, it was shown that the absorbent component in these materials wicked and absorbed aqueous solutions, and the fibers became swollen. Further, these materials wicked even proteinaceous (8-16 mg/ml protein) ice-cold sol-state MATRIGEL™ extracellular matrix which was commonly used in the process of making 3D cell cultures. Furthermore, it was shows that cells of various origins and sources, including multipotent stem cells, primary brain cells such as neurons, secondary brain cells such as astrocytes, and cell lines including hepatocellular carcinoma cells, connective tissue cells and even the bone forming cells can be successfully cultured in these materials. Depending on cell type, culturing conditions, and the number of days culture, cells grew as 3D aggregates such as hepatospheres or neurospheres, as 3D distributed cell networks, or 3D distributed cell networks in an extracellular matrix in these materials. Accordingly, whenever an absorbent fiber or a fiber having an absorbent coating was positioned such that it was partly within a 3D cell aggregate (3D cell spheroid, for example), or when cells grew on said fibers and were surrounded by the other cells and the extracellular matrix, the absorbent materials functioned as passive synthetic vasculature. As used herein, the term "passive", denotes unperfused synthetic vasculature comprising absorbent materials in which capillary and diffusive mass transport is higher than is that through the mass of cells which surround it, or an absorbent material in which capillary and diffusive mass transport is higher than is that through the extracellular matrix when cells are distributed in it.

For all Example presented herein, the absorbent synthetic vasculature was efficient so long as the flow and mass transport resistance through the absorbent fiber(s) and/or the absorbent coating(s) was lower than that through the mass of cells surrounding the vasculature (for example, when vasculature passed through 3D cell spheroids) or lower than that of the gel comprising one or more embedded cells (for example, in a MATRIGEL™-based cell culture).

Figure 1:
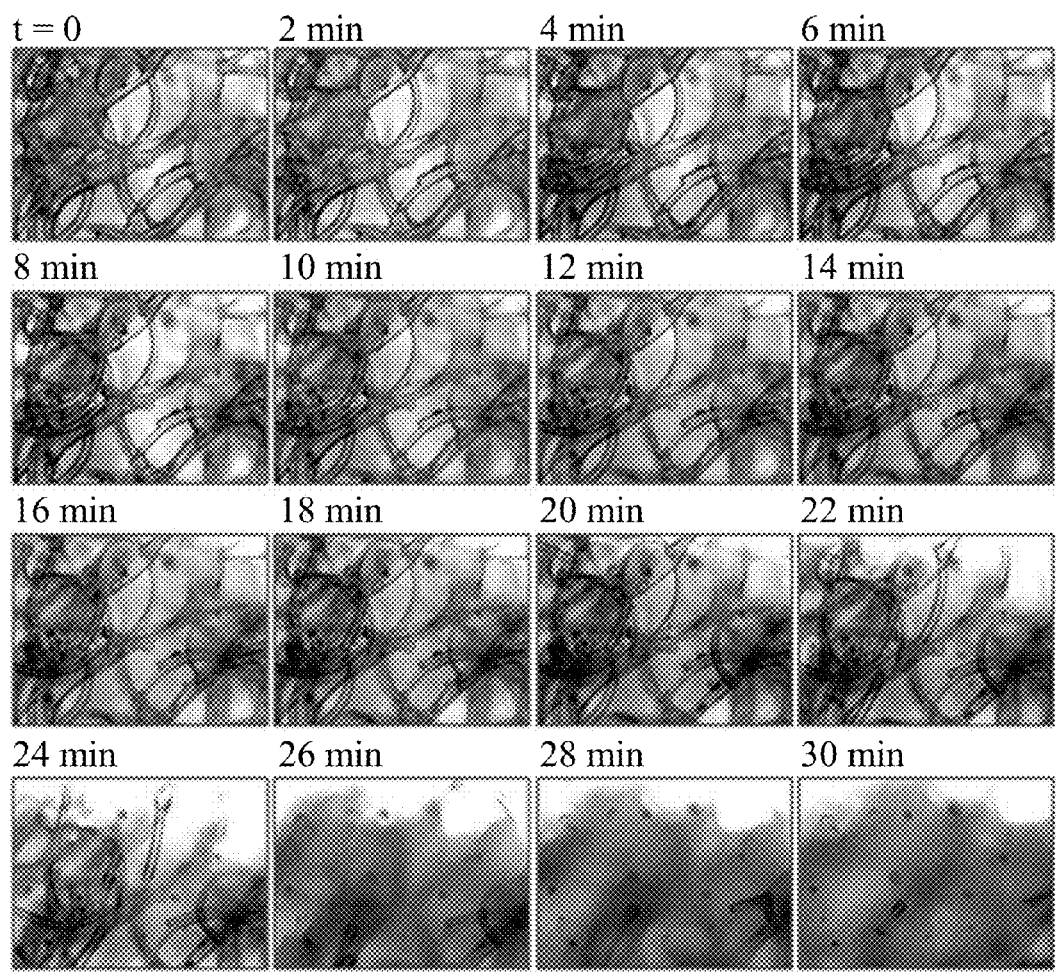
FIG. 1 contains a sequence of photographs taken during 30-minute room temperature drying of the PVOH hydrophilic and absorbent scaffold and synthetic vasculature at 10× in bright field (x=980 μm, y=735 μm). During drying, the swollen PVOH fiber diameter reduced, but it was still swollen with respect to its dimensions in a dry state; thus, enabling 3D cell culture transfer from and to disposables without excessive culture drying.

The sequence of images in FIG. 1 shows the drying of a custom-produced (wet laid) scaffold-vasculature comprising Kuraray Kuralon PVOH fibers. The fibers were supplied by Engineered Fibers Technology, product No. VPB 105-2. Images were taken in a fixed field of view at 10×. Prior to imaging, the material was wetted and then damped between sheets of Kim wipes. During 30-minute room temperature drying, fibers went in and out of the fixed field of view as the material height reduced. However, a dramatic loss in water content was not seen in the first 20 minutes of drying in which the majority of fibers photographed at the start of imaging still remained in the field of view. During this period, the diameter of swollen (absorbent) fibers reduced, but did not halve indicating that PVOH material still retained water. As the material substantially retained water, it enabled the transfer of 3D cell cultures anchored within the said scaffold-vasculature without excessive drying of the cultures during routine transfer from and to cellware disposables.

Accordingly, the use of absorbent or water retentive materials, and/or the absorbent and hydroscopic materials in the process of making a scaffold-synthetic vasculature provided for a method to prevent the excessive 3D cell culture drying during routine manipulations, wherein said 3D cell cultures were anchored within said scaffold comprising synthetic vasculature.

Example 2

Additional Anchoring, Hydrophilic and Absorbent, Scaffold Compositions Comprising Hydrophilic and Absorbent Synthetic Vasculature which Extended to all Exterior Surfaces of the Rigid Scaffold A material comprising a blend of cellulose and synthetic fibers with PVOH binder was acquired from Pall Corporation, product No. SMCON01 (conjugate pad type 8301). According to the supplier the material thickness was 355.6-444.5 µm, typical basis weight of 50 g/m$^2$, tensile strength of 10.3 lbs in MD, water absorption capacity of 28 µl/cm$^2$ and the average wicking rate of 226 seconds per 3 cm. The material was punched into disks of 9.5 mm in diameter. The measured thickness was approximately 400 µm. FIG. 2A shows a 4× photograph of the material in bright field after staining with a brown dye solution in DI water, followed by 30 minute room temperature drying. At least one type of fiber and/or its coating was absorbent and swollen in the aqueous solution (and stained dark). In wicking tests, the disks wicked 30 µl of ice-cold 8 mg/ml protein sol-state Growth Factor Reduced (GFR) MATRIGEL™ extracellular matrix instantly or within 10 seconds. GFR MATRIGEL™ was delivered to the disks by a standard micropipette and standard pipette tip. The pipette tips were kept in the freezer prior to dispensing (in order to be ice-cold when dispensing MATRIGEL™, in agreement with BD Biosciences protocols).

Another exemplary material was SpectraMax® from Cerex Advanced Fabrics (the supplier). According to the supplier, SpectraMax® was non-toxic, nonwoven spunbond nylon suitable for medical application. Product brochure stated that the material was Nylon 6.6, with water absorption of 1.4%; 2.5% at 23° C., 50% RH; and 8.5% at 23° C., 100% RH (ASTM D-570). The material safety data sheet (dated May 20, 2010) stated that the material composition was adipic acid—hexamethylenediamine resin (Nylon 6,6) 92%-100%, polycaprolactum (Nylon 6) 0-6%, and titanium dioxide 0-2%. SpectraMax® in various thicknesses was found to be hydrophilic and wick water. SpectraMax® in 68 g/m$^2$ and 102 g/m$^2$ fabric weight (ASTM D3776), respective thickness of 0.33 and 0.43 mm (ProGage, ASTM D5729), and respective air permeabilities of 0.7 and 0.41 (Tex Test, ASTM D737), wicked, spread and self-contained the absorbed DI water. These materials further wicked 30 µA of ice-cold 8 mg/ml GFR MATRIGEL™ (dispensed by a micropipette) within 10 seconds. The thinner materials such as SpectraMax® in 24 g/m$^2$ fabric weight (FIG. 2B) had to be folded and/or overlapped once or multiple times to self-contain micropipette-dispensed water drops in 30 µA volume or higher when seated in a Petri dish. SpectraMax® in 68 g/m$^2$ fabric weight (and higher) had a "herring bone" pattern (FIG. 2C) which was made (according to the supplier) by spinning and thermally bonding 3 denier continuous filaments of nylon (PA66) into a conformable, textile-like fabric. SpectraMax® materials formed 3D network of hydrophilic fibers (scaffold) with an absorbent coating (vasculature) which extended to all of the material surfaces. Hydrophilic, wicking and absorbent properties of SpectraMax® were attributed to 3D porous material structure and to titanium dioxide coating which also appeared absorbent (see dark staining of fiber perimeter in FIG. 2D after staining with a brown dye solution, followed by drying).

Example 3

Methods of Controlling the Volume Fraction of Synthetic Vasculature and Capillary-to-Capillary Distances The vasculature volume fraction is an important factor in modeling vascularized tissues using 3D cell culture models. Tissues that are perfused in vivo generally have different volume fraction of capillaries within their interior. Accordingly, to model said tissues using 3D cell cultures, a control of the synthetic vasculature volume fraction was desirable. Production methods disclosed herein and in U.S. Provisional Patent Application Ser. No. 61/712,943 and in U.S. patent application Ser. No. 13/962,403 enabled the control of synthetic vasculature volume fraction by controlling mass fraction of the absorbent component in the final scaffold composition during manufacture, using the exemplary wet-laid process among other disclosed methods, provided for a mixture of absorbent fibers, absorbent fibers and other fibers, absorbent coating on the fibers etc.

While in most in vivo tissues cell distance from capillaries is between 10 µm and 100 µm, this distance varies with a tissue type and it was desirable to control it in 3D cell culture models of said tissues. For example, the mean inter-capillary distance in the human brain is about 40 µm with the average distance of neuron to capillary of 8 µm to 20 µm [Spencer, B. J. and Verma, I. M. 2007. Proc Natl Acad Sci USA. 104(18):7594-7599]. In a rat and human heart, capillary to capillary distance is about 20 µm [Martini, J. and Honig, C. R. 1969. Microvasc Res. 1(3):244-256]. This distance is approximately 110 µm for human large intestine [Fait, E., Malkusch, W., Gnoth, S.-H. et al. 1998. Scanning Microscopy 12(4):641-651], and approximately 15 µm for liver. Mixing of known mass of the absorbent fiber or absorbent component in a final fiber slurry, wet laying, followed by pressing and other methods disclosed herein and in U.S. Provisional Patent Application Ser. No. 61/712,943 and in U.S. patent application Ser. No. 13/962,403 provided for a method to control "capillary-to-capillary" distances intra-3D-culture to mirror those present in tissues in vivo, wherein the "capillaries" in vitro were mass transport permeable and hydraulically conductive fibers, or mass transport permeable and hydraulically conductive coatings on the fibers or both.

Example 4

Methods of Controlling "Capillary" Diameters of the Synthetic Vasculature

Typically capillaries are approximately 5 µm to 10 µm in diameter. However, some capillaries have pores with a wide range of openings in various tissue sections spanning from 50 nm for small fenestrated capillaries to 40 µm for sinusoidal capillaries. In modeling specific tissues and tissue sections using 3D cell culture models it was desirable that capillary diameters be controlled.

The used (1) absorbent fibers in a range of diameters and/or (2) absorbent fibrillated fibers and/or (3) non-absorbent fibers in a range of diameters having same or different thickness of the absorbent coating provided for a method to vascularize 3D cell cultures with "capillaries" which diameters mirror those in tissues in vivo. Suitable examples disclosed in the U.S. Provisional Patent Application Ser. No. 61/712,943 and the U.S. patent application Ser. No. 13/962,403 included "intra-culture capillaries" of varying diameter presented by the absorbent, mass transport permeable and hydraulically conductive (permeable to fluid flow) fibrillated cellulose fibers (Lyocell Tencel); various diameters of the absorbent PVOH fibers which were mixed in a slurry in the exemplary wet-laid process; various thicknesses of the PVOH coating applied to borosilicate glass fibers of different diameter; and their combinations. An exemplary combination included the mixture of cellulose fibers and glass fibers with PVOH coating produced using the exemplary wet-laid process, wherein the material was not toxic to the cells in culture, yet the use of fibrillated fibers in the scaffold-vasculature composition provided for a method to better vascularize 3D cultures in terms of range of intra-culture capillary diameters owing to both the adjustable PVOH coating thickness and the adjustable content of fibrillated fiber in the final material composition.

Accordingly, methods disclosed in the U.S. Provisional Patent Application Ser. No. 61/712,943 and the U.S. patent application Ser. No. 13/962,403 and any other method known in the art which provided for a mixture of fibers wherein at least one fiber in the mixture was absorbent and/or had an absorbent coating, and the absorbent fiber diameter and/or the thickness of the absorbent coating was adjustable provided for a method to control "capillary" diameter of the synthetic intra-culture vasculature.

Example 5

Methods of Controlling Synthetic Vasculature Distribution in the Vertical (z) Direction As disclosed in the U.S. Provisional Patent Application Ser. No. 61/712,943 and U.S. patent application Ser. No. 13/962,403; in custom formulations comprising PVOH fibers and PVOH-coated borosilicate glass fibers, centrifugation during manufacture, which was applied just prior to drying step, provided for a method to stratify fibers in the scaffold. Accordingly, this provided for the means to localize the more mass- and flow-transport permeable PVOH fibers to sit on top of the generally less mass- and flow-transport permeable PVOH-coated glass fibers. This was significant because scaffold-vasculature materials comprising distinct compositions in the z-direction were advantageous for reconstructing multi-layered tissues such as neocortex, or cerebral cortex. In general, such tissues comprise different tissue layers, wherein each tissue layer comprises generally different cell types with the correspondingly layer-to-layer-different cell demands with respect to biomechanical and permeability properties of the extracellular environment. As used herein, the term multi-layered tissue reconstruction designates 3D cell cultures overlaid in multiple layers, wherein each layer includes one scaffold (and synthetic vasculature) with one or more 3D cell cultures embedded in it, and wherein each 3D culture comprises a plurality of cell layers.

Accordingly, the disclosed fabrication methods enabled formation of z-stratified composite scaffolds (with synthetic vasculature) of distinct flow and mass permeability properties in the z direction in a single manufacturing step. However, the same could have been obtained in multiple steps by, for example, overlaying and thermally, ultrasonically, by way of pressure (and heat) or otherwise bonding of different materials in the z-direction, or by way of any other method known in the art which provided for different fibers or their compositions in the z-direction.

Example 6

Vasculature Permeability Assay Under Hydrostatic and Osmotic Pressure Differences Using Methylene Blue as a Model Drug In this assay a 24-well insert system comprising an integral 24-well insert, a 24-well plate and a lid (BD Falcon™ Multiwell 24 well insert system, supplier catalog No. 351185) was used. Each well of the insert had a side port access to a respective well of the 24-well plate when the 24-well insert was seated into the 24-well plate. Each well of the insert further comprised a high density Polyethylene Terepthalate (PET) membrane with 8 µm pores and a pore density of $10^5$ pores/cm$^2$. The effective diameter of the PET membrane was 6.5 mm with effective area of 0.3 cm$^2$, according to the manufacturer. The distance between the PET membrane and the well of the 24-well plate, when the integral 24-well insert was seated into it was 2.16 mm.

Figure 3:
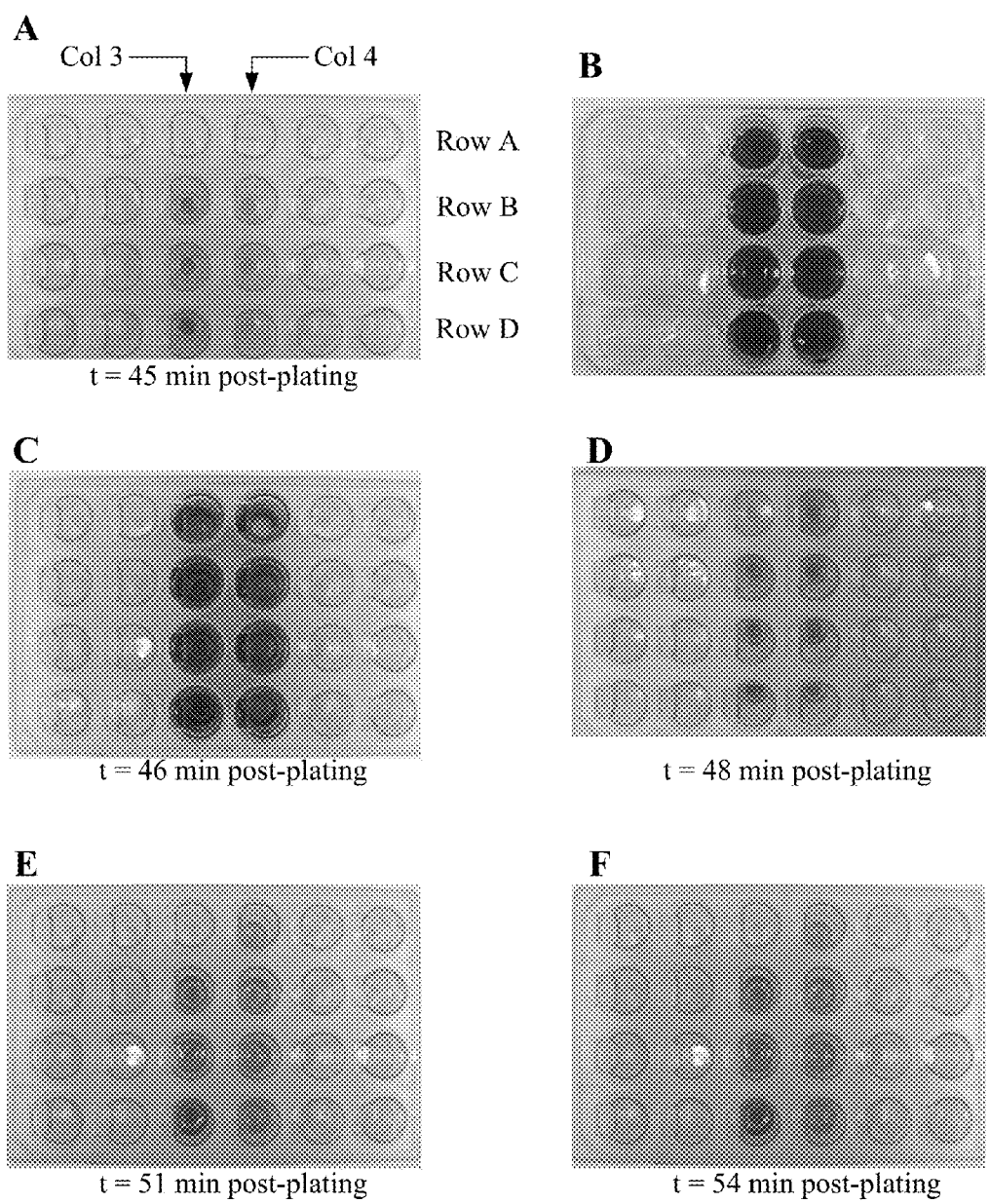
FIG. 3 contains photographs of a vascular permeability assay conducted in a BD Falcon™ Multiwell 24 well insert system using Methylene Blue as a model drug. Row A-Column 3 served as a blank control (PET membrane). Row A-Column 4 had a PDL-coated G041 material adhered to PDL-coated PET membrane. Rows B-D in Column 3 comprised MATRIGEL™ extracellular matrix controls adhered to PDL-coated PET membrane. Rows B-D in Column 4 had MATRIGEL™ embedded into PDL-coated G041 material which was adhered to PDL-coated PET membrane.

Four 6.5 mm disks, punched out of absorbent G041 material supplied by Millipore were sterilized by UV irradiation and then seated into the fourth column of the 24-well insert such that each disk was adhered to respective PET membrane in the corresponding insert well. Next, except for one well (Row A, Column 3), Column 3 and Column 4 of the 24-well insert were coated by 100 µg/ml Poly-D-Lysine (PDL) solution (FIG. 3A). The coating ensured good adhesion of G041 material disks to the PET membrane (Row A-Column 4), and subsequent good adhesion of MATRIGEL™ to PDL-coated PET membrane (Rows B-D in Column 3) or PDL-coated G041 material adhered to PDL-coated PET membrane (Rows B-D in Column 4).

Matrigel Basement Membrane Matrix, Growth Factor Reduced, High Concentration (HC) LDEV-Free (BD part No. 354263) at a final concentration of 16 mg/ml was delivered in a sol-state into Rows B-D in Columns 3-4 (of the 24-well insert) using positive displacement pipette (Gilson, Microman M100) and ice-cold pipette tips (Gilson capillary pistons, CP100ST). 18 µl of MATRIGEL™ was delivered first to wells in Column 3 and then to wells in Column 4 in the following order Row B, Row C and Row D for both columns. This ensured that MATRIGEL™ completely covered the PET membrane in Column 3, and was wicked into the G041 material in Column 4 such that that there were no voids in G041 material as inspected visually. At such a high protein concentration, it was difficult for MATRIGEL™ to distribute and uniformly cover the PET membranes. In contrast, in the presence of G041 material disks in Column 4, MATRIGEL™ was wicked instantly during dispensing (or within 10 seconds) and distributed uniformly within the G041 material as shown in FIG. 3A. Assuming there were no losses in pipetting, MATRIGEL™ thickness on PET membranes, was approximately 540 µm.

Following MATRIGEL™ delivery, the insert system comprising the 24-well insert seated in a 24-well plate and covered by a lid was transferred to 37° C. 5% CO$_2$ incubator for 45-minute MATRIGEL™ gelling. During this time, 1 ml of 0.01% Methylene Blue solution was delivered to another identical 24-well plate to each well in Columns 3 and 4 (FIG. 3B). Next, the insert system was taken from the incubator, the insert removed and placed into the 24-well plate with the Methylene Blue solutions and then covered by a lid (FIG. 3C). Two minutes after sitting in Methylene Blue solutions, the insert with MATRIGEL™ controls and MATRIGEL™ in G041 material, was transferred to another 24-well plate for imaging (FIG. 3D). As seen in color, all insert wells in Column 4 comprising G041 material, were dyed blue. Wells in Row B-D in Column 4 were stained darker blue than was the well in Row A because the latter had no gel to receive the dye (it had only the G041 material). Under identical conditions, insert wells in Column 3, Rows B-D, which comprised MATRIGEL™ controls (the gel on PET membrane), were still stained red with a weak blue staining. The red staining originated from Phenol Red in MATRIGEL™ while low-intensity blue staining originated from Methylene Blue.

As seen and imaged colorimetrically, the intensity of Methylene Blue staining in MATRIGEL™ controls (Column 3, Rows B-D) was insignificant compared to the corresponding wells in Column 4 in which MATRIGEL™ was in G041 material. Accordingly, under conditions tested, MATRIGEL™ residing in the G041 material had lower resistance to mass transport than did MATRIGEL™ alone. This was attributed to the absorbent PVOH synthetic 3D vasculature in G041 material which caused faster uptake of Methylene Blue solution and more uniform staining of MATRIGEL™ residing in the said more absorbent G041 material. Further, in MATRIGEL™ controls, Methylene Blue staining was inconsistent among the 3 replicates. As visually inspected and imaged, blue color in Row D well was barely noticeable. It was discernible in Row B well, and it was the strongest (but not uniform) in Row C well. This showed that MATRIGEL™ controls had poor consistency well-to-well without the absorbent G041 synthetic vasculature. Next, as imaged and shown in FIG. 3D, the insert wells with MATRIGEL™ in G041 material (Column 4, Rows B-D) had an amount of liquid above the gel embedded in the G041 material, whereas in MATRIGEL™ controls in Column 3, only the Row C well had an amount of liquid above the gel (this well also had the strongest Methylene Blue staining among the 3 MATRIGEL™ controls). The presence of liquid above MATRIGEL™ embedded in G041 material corroborated that MATRIGEL™-G041 vasculature model was more permeable to mass transport than was the pure MATRIGEL™ vasculature model, i.e. under conditions studied the former passed more liquid than did the latter.

After imaging, the 24-well insert was transferred back into the 24 well plate with Methylene Blue solutions. Next, Columns 3 and 4 of the insert were filled with 300 µl of DI water per insert well. Under these conditions, hydrostatic pressure difference (which previously facilitated Methylene Blue permeation into the insert wells without liquid), was equilibrated across the PET membrane. Based on manufacturer specifications, to equilibrate pressure across the PET membrane required 1 ml of liquid in the plate well and 300 µl of liquid in the insert well. Hence, following the addition of DI water into the insert wells, predominantly diffusive mass transport was expected. After 3 minutes of sitting in Methylene Blue solution in the corresponding wells of the 24-well plate, the 24-well insert with MATRIGEL™ vasculature and MATRIGEL™-G041 vasculature was transferred to another 24-well plate, and imaged as shown in FIG. 3E. As seen and imaged in color, MATRIGEL™ in G041 material (Column 4, Rows B-D) had uniformly blue-stained gel, while the corresponding wells in Column 3 (MATRIGEL™ controls) still had the red-stained gel with weak bluish staining of increasing intensity but now from Row B, to D, to C.

Following imaging, the 24-well insert was transferred back into the 24-well plate with Methylene Blue solution in Column 3 and 4. After 3 minutes, the 24-well insert was removed and transferred into another 24-well plate for imaging. It was seen that MATRIGEL™ in at least one well in Column 3 failed; i.e. it was in part peeled off or failed to adhere to the PET membrane. To clarify the gel condition, liquid was aspirated from all insert wells and the underside of the insert (the PET membrane) wiped with a Kim wipe. The insert was flipped upside down and imaged (FIG. 3F). It was found that MATRIGEL™ controls in Column 3 failed in 2 out of 3 well replicates in routine transfer protocols. In Row C, MATRIGEL™ was disrupted and peeled off from the center of the PET membrane. In Row B, MATRIGEL™ had distinct vertical channels representative of erosion in the gel due to either high constant pressure difference (for 2 minutes the gel was submerged in Methylene Blue with no liquid in the insert well, FIG. 3D), or sudden surge in pressure and abrupt changes in surface tension due to insert placement or transfer from the plate (with or without DI water in the insert well). The gel erosion due to both excessively high pressure difference across the gel and due to sudden pressure surge were observed previously. Therefore, formation of vertical channels in the gel in the direction of normal pressure and its gradient found herein, were consistent with previous findings in both gel based 3-D cell cultures and slices of explanted tissue [Rambani, K., Vukasinovic, J., Glezer, A. et al. 2009. J Neurosci Methods 180(2):243-254].

This study showed that MATRIGEL™ plated in an absorbent scaffold/vasculature was (1) more permeable to mass transport, (2) more consistent, and (3) could not be peeled off or aspirated in routine aspiration and transfer protocols. The study further showed that even for a small molecule as was Methylene Blue, MW ~320 Da, the PVOH synthetic vasculature improved mass transport intra-MATRIGEL™, resulting in a uniform drug distribution.

This study also showed that materials comprising an absorbent component which was more permeable to mass transport than was commonly used MATRIGEL™ extracellular matrix, can be constructively reduced to practice as synthetic intra-culture vasculature to distribute molecules intra-gel-3D-culture mimicking soft tissue under both hydrostatic and osmotic pressure differences. (The hydrostatic pressure difference was present when the insert contained no liquid and was inserted into the Methylene Blue solution. The PVOH fibers and the PVOH-coating impregnating glass fibers functioned as synthetic vasculature as they reduced diffusive path lengths intra-MATRIGEL™ which mimicked soft tissue.)

As disclosed in the U.S. Provisional Patent Application Ser. No. 61/712,943 and the U.S. patent application Ser. No. 13/962,403, 3D cultures in MATRIGEL™ were cultured successfully in materials with the absorbent PVOH passive synthetic intra-culture vasculature which extended to all exterior surfaces of the rigid scaffold. Next, MATRIGEL™ 3D cultures comprising said vasculature were superior than MATRIGEL™ 3D cell culture controls (see Example 13 in the U.S. patent application Ser. No. 13/962,403). For example, 3D cell networks were more developed and cell processes longer and more spread than in MATRIGEL™ 3D cell culture controls. This was attributed, in part, to improved mass transport intra-3D-culture owing to the more mass transport permeable PVOH passive synthetic intra-3D-culture vasculature. Other advantages included more homogenous cell distribution in 3D and the ease of 3D culture handling, in that, that 3D cultures in MATRIGEL™ embedded in the anchoring scaffold could not be aspirated, or the cultures peeled off, in routine media exchanges or drug screening protocols, while MATRIGEL™ 3D culture controls could and did.

Example 7

Vasculature Permeability Assay Under Forced Convection Flow Perfusion, Wherein the Scaffold-Vasculature was Hydrophilic and Absorbent In this Example, a rigid scaffold comprising an absorbent synthetic intra-culture vasculature and the embedded extracellular matrix was tested to see if it would be more permeable to flow and mass transport in forced convection perfusion than the extracellular matrix (ECM) alone. As in Example 5, the model scaffold/vasculature was Millipore G041 material and the model extracellular matrix was GFR MATRIGEL™ at 16 mg/ml protein.

A custom 12-well insert system was developed and fabricated for use in this assay, as shown in FIGS. 4A-4B in the respective top and bottom view. It comprised an integral 12-well insert; a universal reservoir (feed tray); and a gas-permeable, optically clear, aseptic lid (not shown). The reservoir had a built-in fluidic port positioned mid-way between the two rows of insert wells, wherein each row comprised 6 wells. The insert was designed in a footprint which corresponded to 2 columns of the standard 48-well plate with respect to well-to-well spacing. The system was fabricated in a standard multi-well plate material using a mold and a vacuum former. Next, six disks of 4.8 mm in diameter were punched out of Millipore G041 material. The disks were silicone-sealed to all wells in the bottom row of the 12-well insert as shown in FIG. 4A. The sealant (Dow Corning, Sylgard 184) was prepared in a 1:10 ratio curing agent to pre-polymer, thoroughly mixed and left in the air until it was viscous enough not to permeate G041 material during contact sealing to the blind insert wells. The bottom row wells (FIG. 4A) were then dip coated in viscous non-toxic silicone, followed by attachment of the G041 material disks. The insert, comprising a row of blind wells and a row of wells with the G041 material disks was then placed in the forced convection oven set to 45° C. for a 24-hour disk-to-insert cure (bonding).

Next, 16 mg/ml protein GFR MATRIGEL™ was delivered to all wells; 10 µl per well in each well of the 12-well insert. The insert wells without G041 material had MATRIGEL™ delivered first. The thickness of MATRIGEL™ was approximately 550 µm assuming no losses in pipetting and a uniform gel thickness. The insert system (with the gas permeable membrane) was then transferred to a 37° C. 5% $CO_2$ incubator for 45-minute MATRIGEL™ gelling. Next, the insert system was taken from the incubator, the lid was removed, and the 12-well insert imaged. As shown in FIG. 4C, in the bottom row wells comprising G041 material disks, MATRIGEL™ filled the material disks entirely and uniformly. (Delivered volume of MATRIGEL™ was tested previously with 4.8 mm in diameter G041 material disks and found to yield uniform gel distribution within the material). In the top row wells (wells without G041 material), MATRIGEL™ was present and was intact in all wells except for the right most well in which a bubble was seen in the gel. (Note that the trapping of air bubbles during MATRIGEL™ dispensing on plastic disposables is quite common even for experienced users of MATRIGEL™ extracellular matrix. However, the bubble trapping was never noticed when MATRIGEL™ was delivered to G041 material).

Figure 4D:
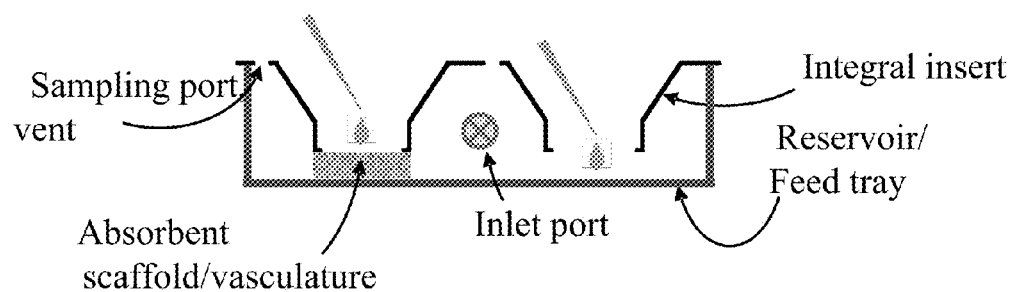
FIGS. 4D-4E are schematic drawings of the experimental setup in a vertical cross section of the insert showing one of each, a blind well and a well with the non-gel hydrophilic and absorbent scaffold-vasculature.
Figure 4E:
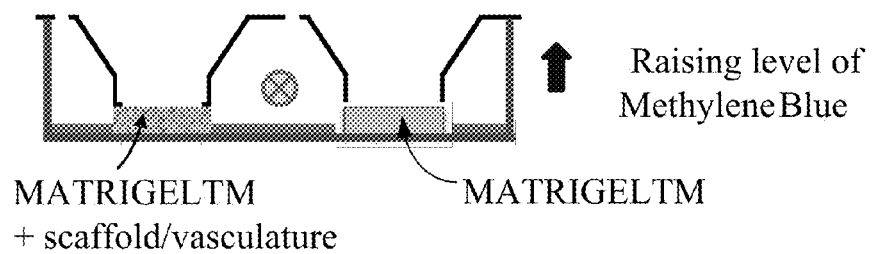

FIG. 4D shows the test setup in a vertical cross sectional view of the insert in a plane comprising one of each, a well with G041 material, and a well without G041 material. For perfusion study, Methylene Blue, known as a potent monoamine oxidase inhibitor was used as a model drug. Methylene Blue (0.01% v/v Methylene Blue in DI water) was then continuously injected into the reservoir through the inlet port using a syringe pump as shown in FIG. 4E. As the liquid level rose, the air in the reservoir evacuated the system through the sampling/vent ports shown schematically in FIG. 4D. During the first 33 minutes of perfusion, the flow rate was 100 µl/min. Then, the flow rate was increased to 200 µl/min without stopping the flow. The rate was then kept constant for another 31 minutes of perfusion.

The perfusion was stopped when the liquid level in the reservoir reached between 4 mm and 5.5 mm in height.

Figure 5:
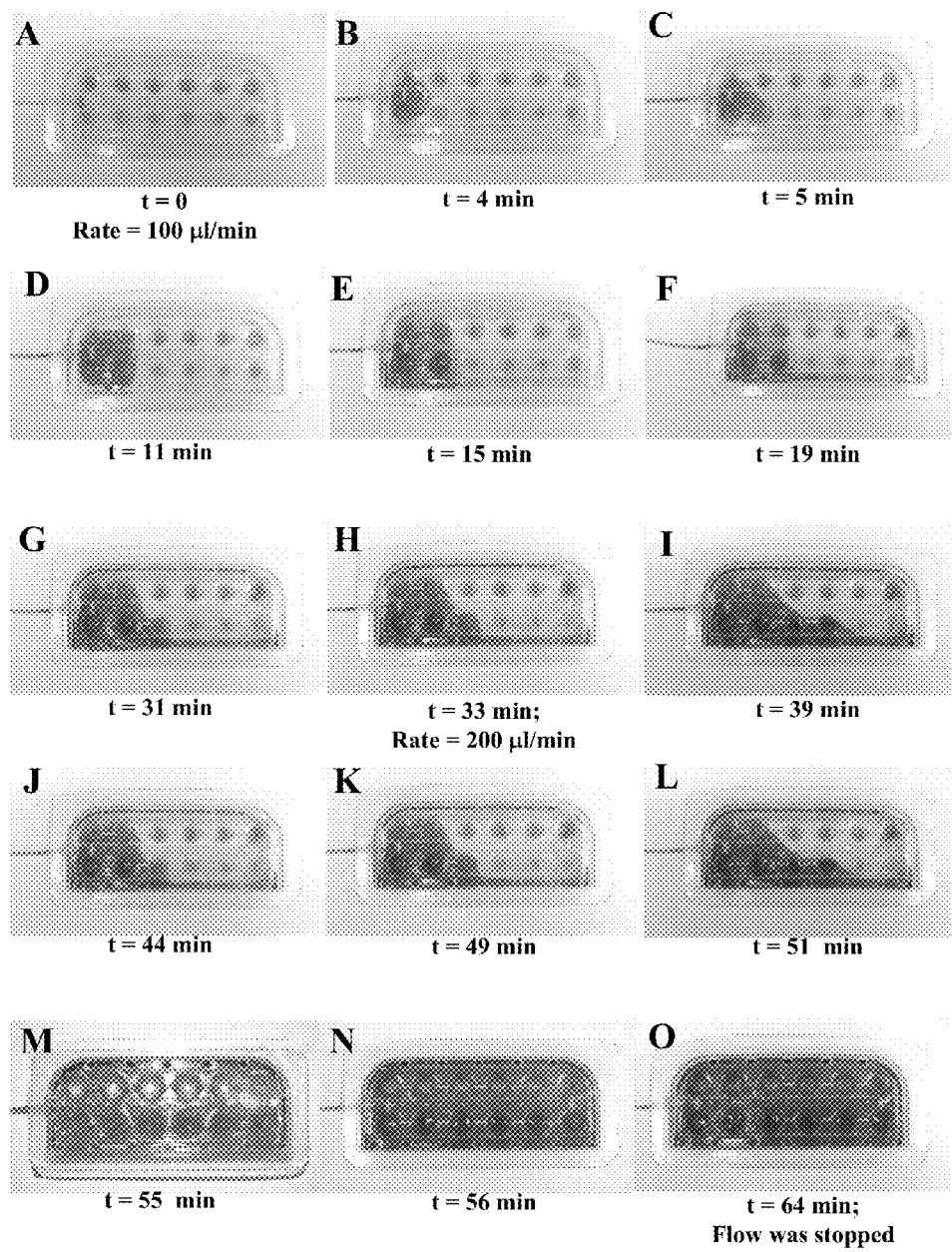
FIG. 5 contains a sequence of time-stamped photographs showing temporal evolution of flow distribution in the reservoir of a custom 12-well insert system with the MATRIGEL™ residing in the insert wells, without (top row) and with (bottom row) non-gel based hydrophilic and absorbent scaffold-vasculature, respectively, during perfusion of a model drug (0.01% Methylene Blue solution).

The sequence of photographs with time stamps in FIG. 5 show temporal evolution of flow distribution in the reservoir with the MATRIGEL™ residing in the insert wells without (top row) and with (bottom row) G041 material disks, respectively. As can be seen from the sequence, when the flow of Methylene Blue (marker) accessed the bottom row wells comprising gel in G041 material, MATRIGEL™ color started to change from dark pink (arising from Phenol Red in MATRIGEL™) to violet, to blue, and to darker shades of blue (FIGS. 5B-5I). Next, when the gel and G041 material could no longer self-contain the excess amount of liquid forced by one-way flow, the liquid level in the bottom row wells started to rise. Further, as the liquid level continued to rise in the reservoir, the liquid level in the bottom row wells also continued to rise (FIGS. 5J-5N). In each well in the bottom row, the liquid level was rising until it was equilibrated with the level of liquid in the reservoir as shown in FIG. 5O. This indicated that 16 mg/ml MATRIGEL™ residing in the G041 material was indeed mass transport permeable and hydraulically conductive, that is, the gel was stained by the marker and there was Methylene Blue solution above the gel.

In contrast, as seen can be seen in FIGS. 5B-5G, MATRIGEL™ controls in the top row wells were not stained by the marker (the staining was not visually observed) not even when the flow rate was doubled and ultimately stopped (FIGS. 5H-5O). (The only exception was the right-most well, in which a bubble was present in the gel. The bubble eventually burst; thus, providing a path of low resistance to flow around the gel in the said well). Further, there was no liquid above the pink stained MATRIGEL™ controls during perfusion, and no liquid was seen above the gel during the period which lasted 40 minutes after perfusion stopped.

The sequence of images in FIGS. 6A-6G corroborate once more that MATRIGEL™ controls in the top row remained pink with no liquid above the gel during and after perfusion, while MATRIGEL™ in G041 material in the bottom row wells was stained blue and had an amount of liquid in the said wells above the gel. When inspected in a side view (FIG. 6F) the liquid level in the bottom row wells was aligned with the level of liquid in the reservoir when the perfusion stopped.

Figure 6:
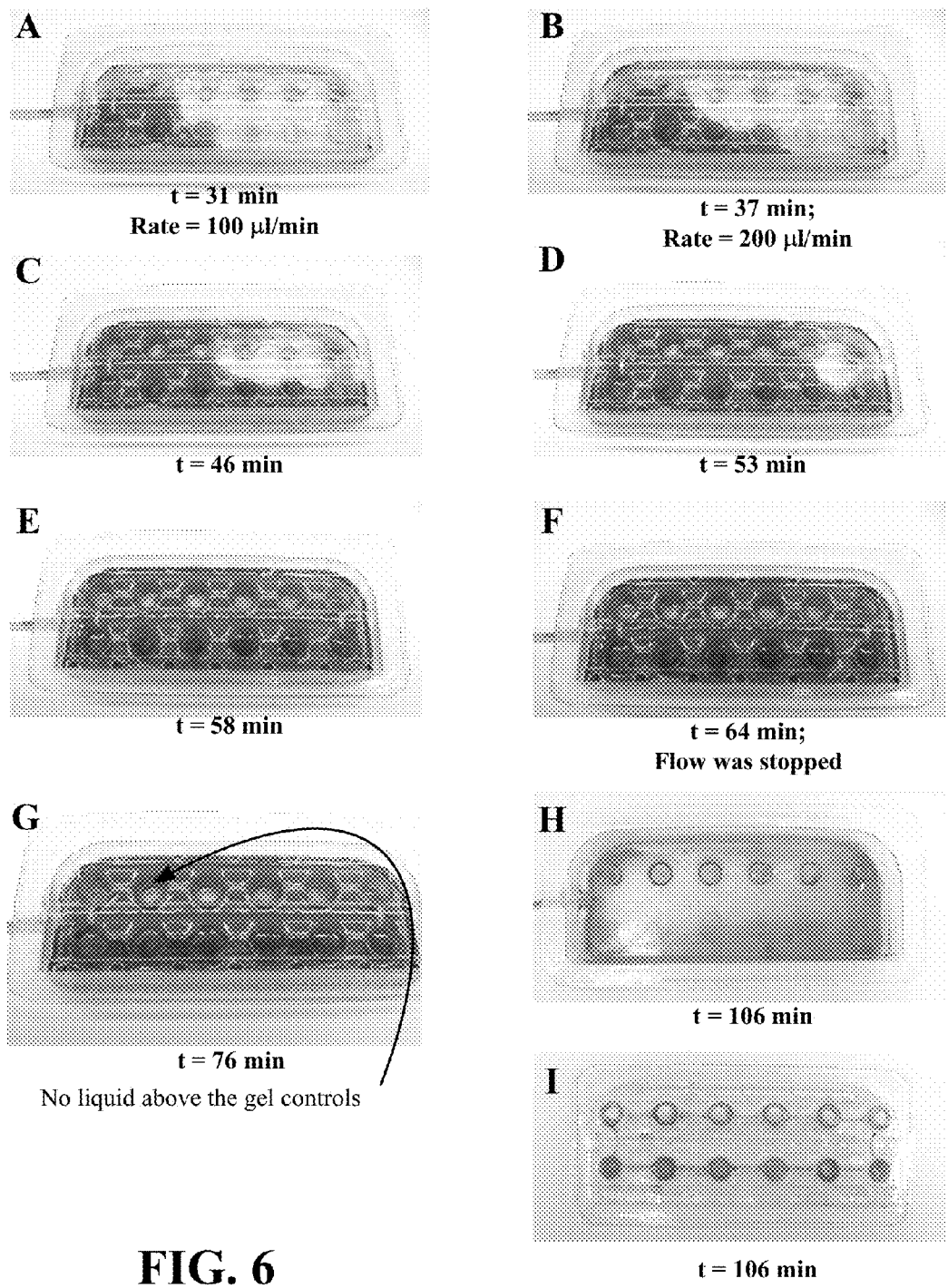
FIG. 6 shows a sequence of photographs of the perfusion permeability assay in a view which shows the level of liquid in the insert wells and the reservoir during the assay.

At the end of study, the insert was removed from the reservoir, and MATRIGEL™ controls remaining in the reservoir imaged. As can be seen in FIG. 6H, in all wells the gel was pink with a bluish hue. A dark blue circle surrounding each gel (except for the right-most gel) clearly demarcated the region in which the flow of Methylene Blue marker attempted to permeate the gel but could not do so because at 16 mg/ml protein MATRIGEL™ acted as a plug. It can further be seen that the right-most gel was damaged by the bubble burst; thus, explaining why only the right-most MATRIGEL™ control well had a liquid above the gel in the perfusion study. Next, the insert was flipped upside down and imaged. As shown in FIG. 6I, MATRIGEL™ embedded in G041 material (bottom row of wells) was uniformly stained blue in all wells by the model drug.

Clearly, MATRIGEL™ embedded in G041 material was more permeable to mass transport in forced convection perfusion than was MATRIGEL™ without it. Accordingly, G041 material functioned as an efficient synthetic intra-culture vasculature distributing molecules intra-gel. First, G041 material was hydrophilic enabling quick wetting. Second, the absorbent component of G041 material started to absorb the marker faster than did the gel. Third, when the absorbent (PVOH) component was saturated, it started to release the marker under pressure difference in a forced convection flow. Fourth, length scales for mass transport in MATRIGEL™ were reduced by approximately an order of magnitude or more by the presence of absorbent materials in G041 material composition. All this facilitated mass transport intra-gel by either convection, diffusion, or both. In essence, the synthetic vasculature acted as a 3D flow distribution network intra-gel.

In sum, the assay confirmed that G041 material functioned as intra-gel vasculature for MATRIGEL™ extracellular matrix under forced convection flow perfusion. MATRIGEL™ embedded in G041 material was more mass transport permeable by convection (forced flow perfusion) plus diffusion as shown by faster and more uniform staining of the gel and G041 material by the marker (Methylene Blue, MW ~320 Da). The assay further showed that under identical conditions, the staining of MATRIGEL™ controls was slow and weak, arising from pure diffusion in the gel. The most important finding was that MATRIGEL™ at 16 mg/ml acted as a gel plug impermeable to flow under conditions tested, whereas MATRIGEL™ embedded in G041 material was permeable to flow and the liquid passed through the gel and collected above it. Finally, throughout the assay the pressure drop imposed through the gel in G041 material never exceeded approximately 60 Pa. This made the synthetic vasculature suitable for non-invasive intra-3D-cell-culture perfusion even when said 3D cell culture comprised 16 mg/ml MATRIGEL™ extracellular matrix.

Example 8

Without Intra-Culture Vasculature, MATRIGEL™ Eroded in One-Way Perfusion

In this study, custom perfusion wells were made in Polydimethylsiloxane (PDMS, Dow Corning, Sylgard 184). Wells measured 4.8 mm in diameter and comprised porous substrate discs of the same diameter. The disks were punched out of hydrophilic, 35 µm porous, 1.6 mm thick polyethylene sheet (Scientific Commodities, Part No. BB2062-35L). Prior to the gel plating, wells with porous substrates were coated overnight in 100 µg/ml Poly-L-Lysine (PLL) solution, rinsed 3× in sterile DI water, followed by 24-hour drying in the cell culture hood. Next, 30 µl of 7.5 mg/ml MATRIGEL™ was plated onto the porous substrates and placed into 37° C. 5% $CO_2$ incubator for 30-minute gelation. Under these conditions, the gel thickness was approximately 1.7 mm assuming that the gel top surface was flat and that there were no MATRIGEL™ losses in pipetting and no MATRIGEL™ losses through the PLL-coated porous disc seating the gel. The porous substrate served to support the gel while permitting entry of flow into the gel. The PLL-coating served to make MATRIGEL™ adhere well to the porous substrate.

There were 3 replicates of each (a) perfused and (b) unperfused 7.5 mg/ml protein GFR MATRIGEL™. After gel gelation, medium was added and the wells with the gel transferred to incubator for a 2-day study. In perfused wells, flow rate was set to 1 µl/min or approximately 58 gel volume exchange per day under forced convection flow of medium comprising Neurobasal+2% B-27+1% G5+0.5 mM Glutamax+1% Pen/Strep. The flow was seen going into and out of the wells during a 2-day long perfusion. PLL-coating ensured that there were no paths of low resistance between the gel and the well; that is, flow forced into the well passed solely through the gel. The flow entry into the gel was at the gel bottom.

Figure 7A:
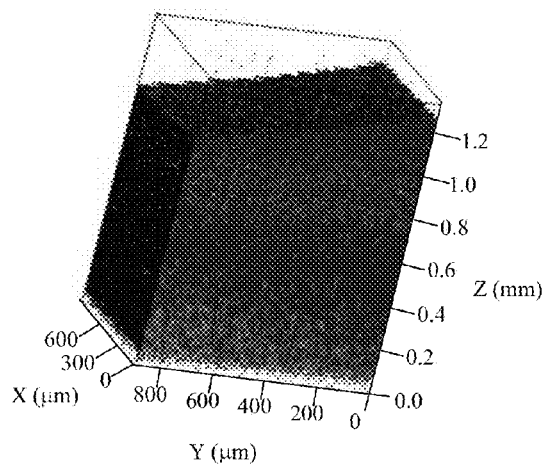
In FIGS. 7A-7C and in FIG. 7E, confocal z-stack was taken bottom-up through the cultures; the plane z=0 is shown at the bottom of the respective cultures.
Figure 7B:
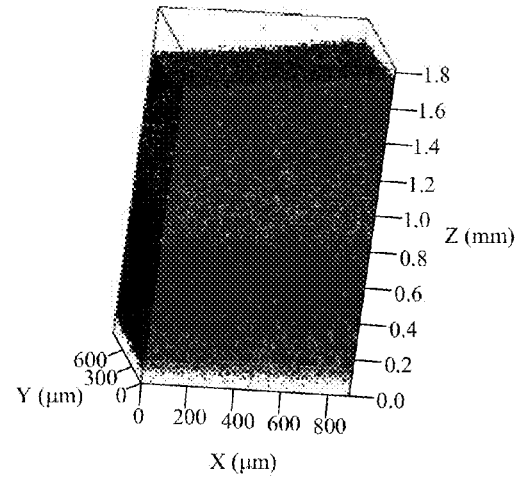
Figure 7C:
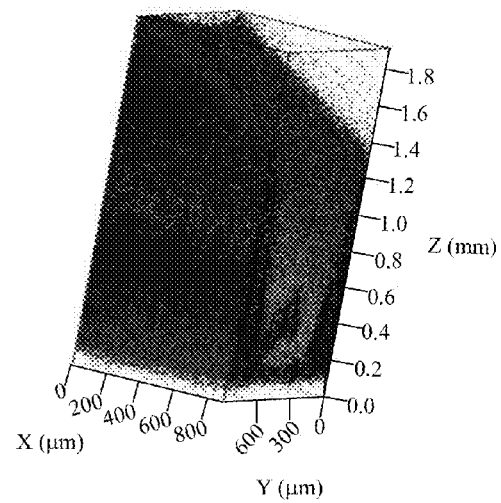
Figure 7D:
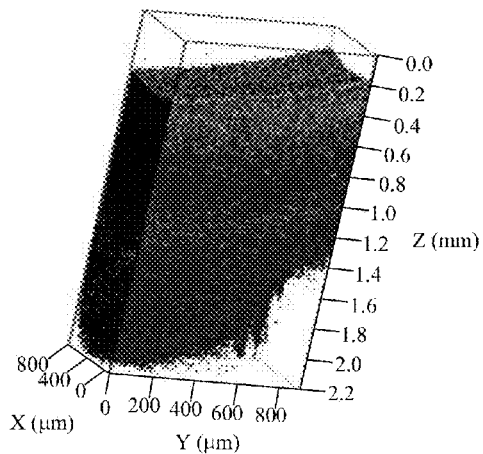
In FIG. 7D and FIG. 7F, confocal z-stack was taken top-down through the cultures; the plane z=0 corresponds approximately to the top of the respective cultures. Perfused MATRIGEL™ was perfused one way, bottom-up, at a rate which was approximately 58 MATRIGEL™ volume exchanges per day.
Figure 7E:
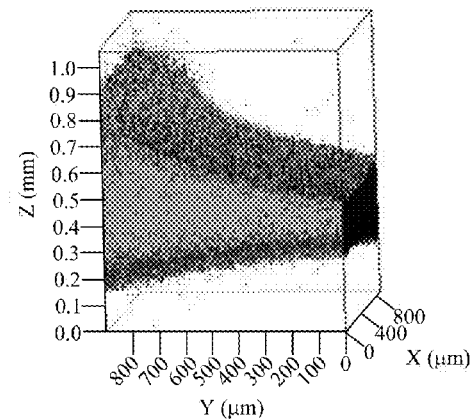
Figure 7F:
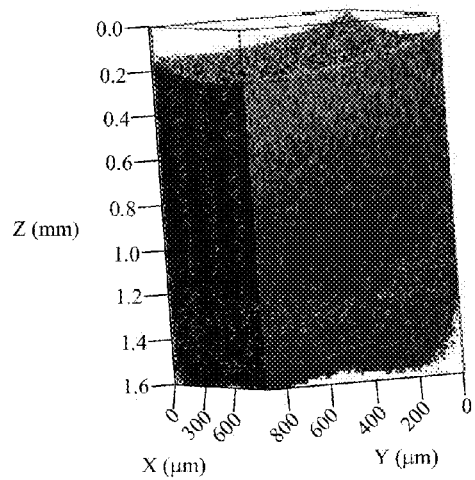

After 2 days, the gel was stained by a mixture of Rhodamine and Calcein and imaged in a z-stack using a 2-channel confocal microscopy. FIGS. 7A-7C show unperfused MATRIGEL™ controls. The unperfused MATRIGEL™ 3D cell culture surrogates were concave at the top, but their bottoms remained flat. The MATRIGEL™ shape on the top was dependent on the boundary conditions and the surface tension at the boundary at plating, and the subsequent gel contraction. FIGS. 7D-7F show perfused MATRIGEL™ 3D culture surrogates which were concave at the top, and eroded at the bottom in a zone where flow entered the gel. While the magnitude of erosion was inconsistent well-to-well, it showed that the gel eroded in perfusion because it was not sufficiently permeable to flow transport by convection under condition tested. (No such erosion was found in unperfused MATRIGEL™ controls.)

This study indicated that thicker gel-based 3D cell cultures comprising widely used MATRIGEL™ extracellular matrix may be impossible to perfuse non-invasively. Notably, at this thickness most gel-based 3D cell cultures, and especially those comprising cells at high densities, needed some form of perfusion to deliver nutrients intra-culture to prevent necrosis, analogous to slices of explanted tissue of the same thickness. Accordingly, to meet the metabolic demands of cells in approximately 400 µm thick and thicker gel-based 3D cell cultures both perfusion and functional synthetic intra-culture vasculature were needed.

Example 9

Vasculature Permeability Assay Under Forced Convection Flow Perfusion, Wherein the Non-Gel Scaffold-Vasculature Fibers were Hydrophilic but not Absorbent The scaffold-vasculature material used in the assay was disclosed in U.S. Provisional Patent Application Ser. No. 61/712,943. Briefly, the material was thermally bonded polyethylene/polyester (PE/PET) bi-component fiber filter media (Midwest Filtration part No. Unitherm 170). As received, the 280 µm thick material was cytotoxic. To make the material non-cytotoxic the material was first cleaned with a scouring solution (1 g Sodium Carbonate+1 mL Tween 20 in 100 mL deionized water) 30-60 minutes at 60° C., then rinsed in 100 mL DI water at 60° C. for 30 minutes, followed by 1-hour treatment in 1% w/v sodium hydroxide solution in DI water at 60° C., rinsing in 100 mL of DI water for 30 minutes at 60° C. to remove traces of NaOH, and dried in the hood overnight. These steps made the material non-toxic but hydrophobic. To make the material non-toxic and hydrophilic, the material was treated by corona discharge in air at an intensity optimized to yield a complete spread of a 25 µl DI water drop dispensed using micropipette.

Figure 8A:
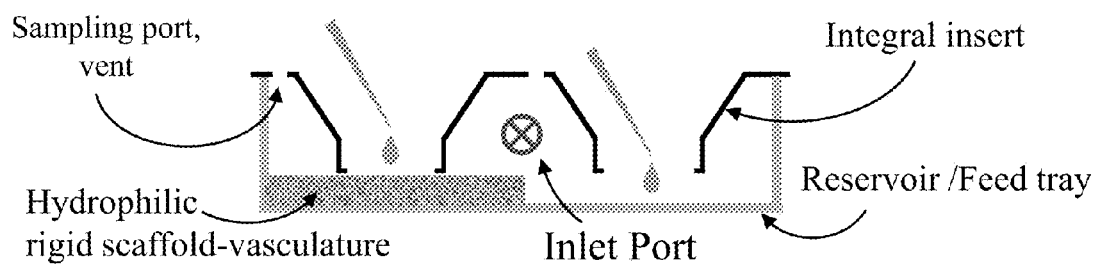
FIG. 8A shows delivery of the gel.
Figure 8B:
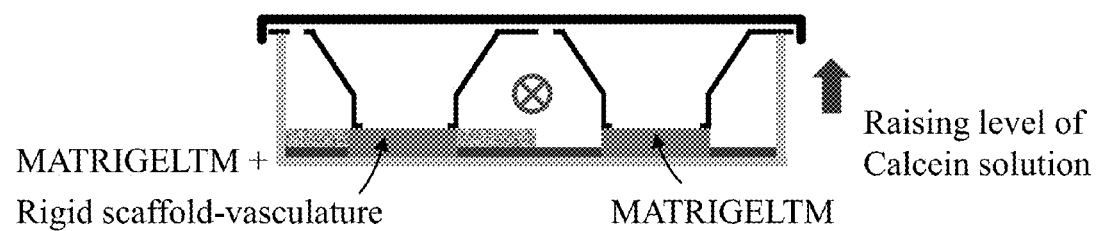
FIG. 8B shows perfusion, the location of MATRIGEL™ in the blind control wells, and the location of MATRIGEL™ in the hydrophilic scaffold-vasculature material.

In this assay, a modified setup comprising 12-well insert system was used (FIGS. 8A-8B). A strip of the corona-treated scaffold-vasculature material was placed into the reservoir such that it covered the area under 6 insert wells in the bottom row (FIG. 8A). The strip covered half the reservoir width at base and the strip length was equal to that of the reservoir. Next, 100 µg/ml Poly-D-Lysine (PDL) solution was added to flood the reservoir comprising the corona-treated Unitherm 170 material and the device incubated in a cell culture incubator overnight with a SealPlate® lid (VWR product No. 60941). Following PDL-coating, the PDL solution was rinsed 1× with sterile DI water, and the device left to air dry for approximately 2 hours in the laminar flow biohazard hood.

Figure 8C:
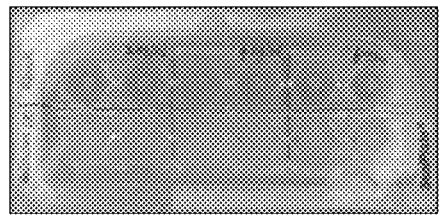
FIGS. 8C-8I show temporal evolution of Calcein marker mass transport intra-MATRIGEL™, without (top row) and with (bottom row) the non-gel based hydrophilic scaffold-vasculature, respectively, during and after perfusion.
Figure 8D:
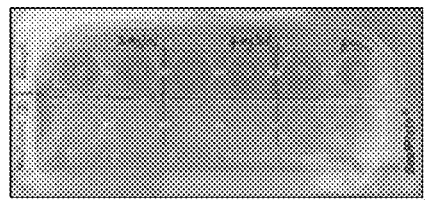
Figure 8E:
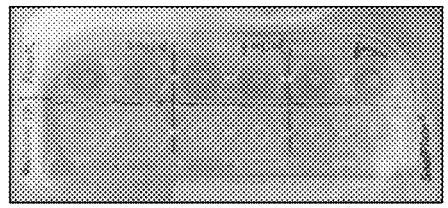
Figure 8F:
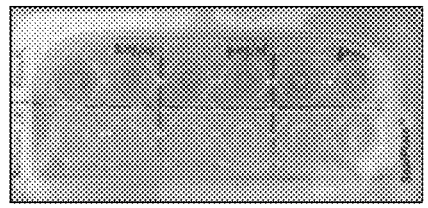
Figure 8G:
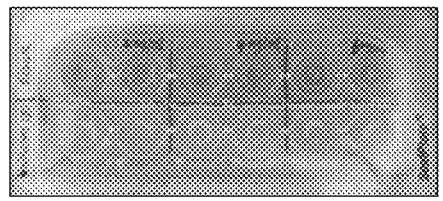
Figure 8H:
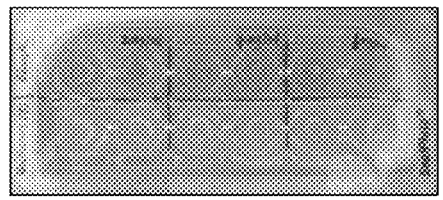
Figure 8I:
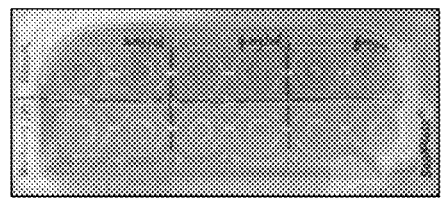

Next, MATRIGEL™ at three concentrations—2 mg/ml, 4 mg/ml, and 6 mg/ml was delivered into the insert wells such that the first two columns had 2 mg/ml, the $3^{rd}$ and $4^{th}$ columns had 4 mg/ml, and the last two columns had 6 mg/ml protein MATRIGEL™; 2 wells per condition as shown in FIG. 8C. The bottom row had the Unitherm 170 material and the top row did not. After approximately 15 minute gelling in the 37° C. incubator and 5 minutes at room temperature, Calcein solution in PBS (the marker) was injected into the reservoir at a rate of 1 ml/min. The perfusion was stopped after 10 minutes. As shown in FIGS. 8C-8F, during forced convection perfusion Calcein entered into the gel embedded in the Unitherm 170 material (bottom row) with accompanied rise in liquid level in said wells; however, Calcein did not pass through MATRIGEL™ controls (top row) except for one well comprising MATRIGEL™ at 2 mg/ml concentration. As shown in FIG. 8G, even after over 20 minutes after the perfusion was stopped, there was no liquid above 4 mg/ml and 6 mg/ml MATRIGEL™ controls (the top row of insert wells). Approximately 1-2 hours after the perfusion was stopped, the liquid level above all MATRIGEL™ controls rose and the gel staining process by the Calcein marker became apparent (FIG. 8H). The slow staining continued and approximately 3-3.5 hours after the perfusion was stopped appeared to be complete (FIG. 8I).

Surprisingly, the assay showed that MATRIGEL™ embedded in a hydrophilic scaffold-vasculature in which the fibers were not absorbent, was also more hydraulically conductive than were MATRIGEL™ controls. Even at a relatively low protein (4-6 mg/ml) MATRIGEL™ acted as plug for flow while MATRIGEL™ embedded in the synthetic scaffold-vasculature material did not. As the PDL-coating was generally not considered absorbent, the surprising finding of this perfusion assay was that a hydrophilic material without an absorbent component also functioned as synthetic intra-MATRIGEL™ vasculature.

The mechanism by which a hydrophilic material without an absorbent 3D distributed component functioned as intra-gel vasculature was thought to be different from the mechanism by which the hydrophilic material comprising an absorbent material functioned as synthetic intra-gel vasculature. Specifically, it was thought that despite the adhesive PDL coating (which made the MATRIGEL™ adhere well to the flat surfaces). MATRIGEL™ did not adhere sufficiently well to the 3D fibrous Unitherm 170 material. Consequently, the imperfections in the gel adhesion to the 3D fibrous network created 3D capillary voids intra-gel which functioned as synthetic intra-gel vasculature. However, the gel could still be transferred, and routinely handled even using tweezers, if embedded in said hydrophilic material.

Figure 9A:
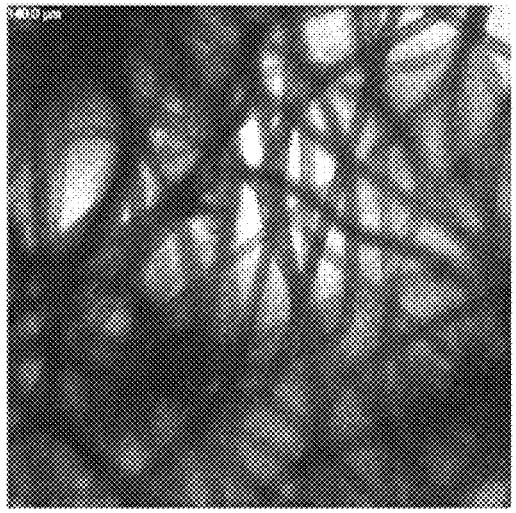
FIG. 9 comprises confocal micrographs of MATRIGEL™ at 2 mg/ml (FIG. 9A), 4 mg/ml (FIG. 9B), and 6 mg/ml (FIG. 9C) embedded into the hydrophilic scaffold-vasculature (without absorbent materials in its composition) after the permeability assay using forced convection flow perfusion. The images were taken at z=140 µm (mid-way through the material thickness) using a Zeiss LSM 510 microscope at 10 (x=898.24 µm, y=898.24 µm).
Figure 9B:
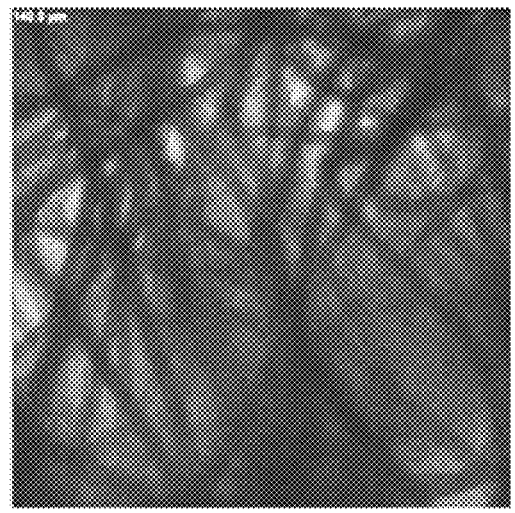
Figure 9C:
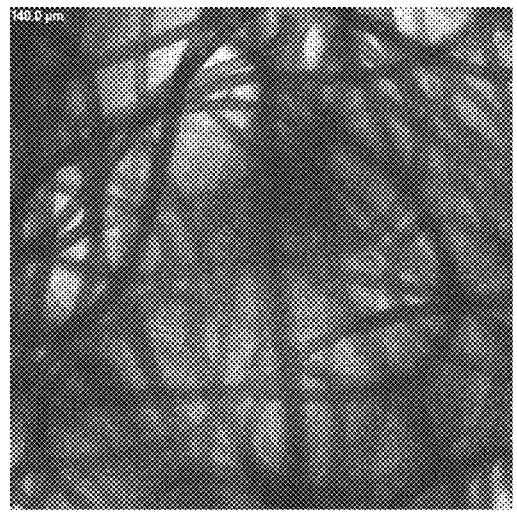

To examine the size of intra-gel capillary voids, the gel in the Unitherm 170 material was imaged in a z-stack using a confocal microscope at the end of the assay. Images taken mid-way through the thickness of Unitherm 170 material (z=140 µm) are shown in FIGS. 9A-9C for 3 tested MATRIGEL™ concentrations. As can be seen, the gel staining by Calcein was uniform and gaps between the gel and the fibers could not be seen at 10×, likely because they were under 10 µm.

In sum, for hydrophilic 3D fibrous network materials to function as synthetic intra-gels 3D cell culture vasculature during perfusion the following three conditions had to be satisfied. First, the gel adhesion to hydrophilic materials had to form intra-gel capillary voids which form 3D network that extends to at least one surface of the gel, and preferably all. Second, the resistance of fluid flow per unit length and unit area of intra-culture capillary voids had to be lower than the same through the gel. Third, during perfusion flow rate had to be sufficiently high for the 3D network of intra-culture capillary voids to remain open for the low to pass.

Example 10

Intra-3D-Culture Perfusion Method, Perfused Multiwell Insert System, and Methods of Making and Using the Same in Conjunction with the Rigid and Absorbent Synthetic Scaffold-Vasculature in Bi-Directional 3D Cell Culture Perfusion Application Six custom 12-well insert systems were used in the following arrangement:

| Perfused cultures (n = 3 × 2 per condition) | Unperfused control cultures (n = 3) |
|---|---|
| Insert system 1: Cells in 8 mg/ml MATRIGELTM in G041 material n = 3 | Insert system 3: Cells in 8 mg/ml MATRIGELTM in G041 material |
| Insert system 2: Cells in 8 mg/ml MATRIGELTM 1 in G041 material n = 3 | |
| Insert system 4: Cells in 8 mg/ml MATRIGELTM in PDL-coated G041 n = 3 | Insert system 6: Cells in 8 mg/ml MATRIGELTM in PDL-coated G041 material |
| Insert system 5: Cells in 8 mg/ml MATRIGELTM in PDL-coated G041 n = 3 | |

Figure 10A:
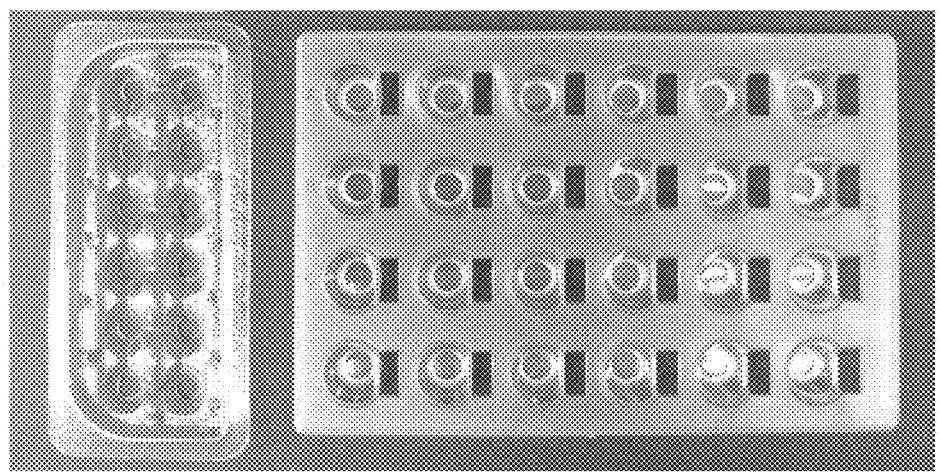
FIG. 10 contains photographs of a custom 12-well insert system. The front and back view of an integral 12-well insert in a format corresponding to 2 columns of the 48-well plate is shown in FIG. 10A and FIG. 10B, respectively. The custom 12-well insert with blind wells (to the left) is shown next to BD Falcon 24-well insert Part No. 351185 (to the right). An unperfused receiving feed tray (the reservoir) is shown in FIG. 10C next to a BD Falcon 24-well plate to show that that the reservoir width was standard at base.
Figure 10B:
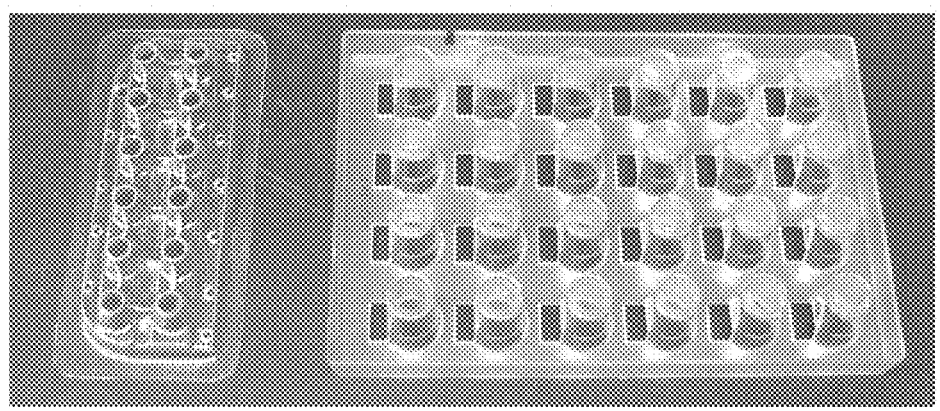
Figure 10C:
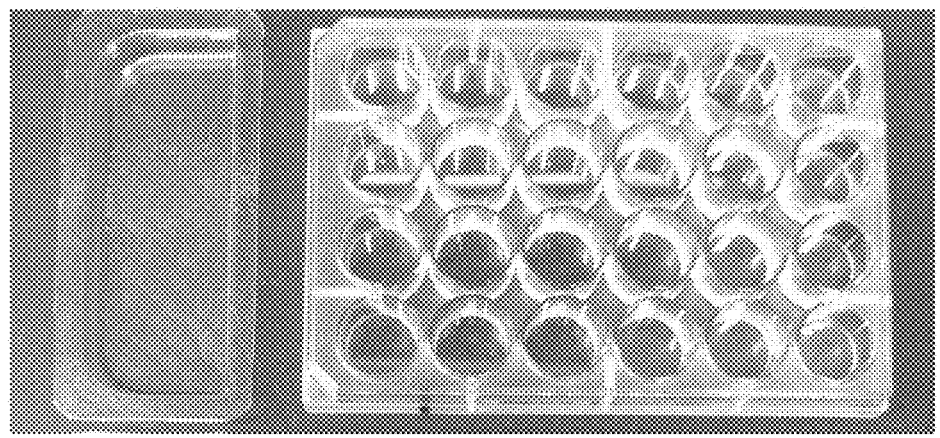

The front and back view of a custom 12-well insert in a format corresponding to 2 columns of the 48-well plate is shown in FIG. 10A and FIG. 10B, in a top and bottom view respectively. The custom insert (to the left) is shown next to BD Falcon 24-well insert Part No. 351185 (to the right) to show that it looked like many of the standard products except that it had blind wells. An unperfused reservoir is shown in FIG. 10C next to a BD Falcon 24-well plate to show that that the reservoir width was standard at base. In perfused and unperfused 3D cell culture studies the 12-well inserts were identical. However, the reservoir (feed tray) had fluidic port(s) in a perfused insert system (FIGS. 4A-4B) and no fluidic ports in an unperfused insert system (FIG. 10C).

In this study, all 12-well insert systems comprised G041 material cut to the shape and size of the reservoir bottom (at base) and seated into the reservoirs. All materials were UV sterilized. Prior to 3D culture plating, the insert systems designated for PDL-coating were incubated overnight in 100 µg/ml PDL solution (Poly-D-Lysine, Sigma-Aldrich Part No. P7405, MW>300 KDa). After coating, the PDL solution was aspirated, and materials rinsed 3× in sterile DI water, followed by drying in a sterile cell culture hood for 24 hours.

After drying, a 1:1 cell ratio of E-18 primary cortical neurons and P0-harvested and passaged astrocytes was plated into G041 materials in 8 mg/ml sol-state MATRIGEL™ using a positive displacement pipettor and ice-cold pipette tips (capillary pistons). Total live cell density at plating was $5 \times 10^6$ cells/ml (50,000 cells in each well). The 3D culture thickness was approximately 400-420 µm. The culture spread in G041 material was slightly larger than the blind well opening to ensure that flow indeed passed through the culture (not around the culture) during perfusion as shown schematically in FIGS. 11A-11B. Within 5 minutes after plating, all six systems were sealed by an aseptic, 25 µm thick, clear, gas permeable membrane Breathe-Easy® (Diversified Biotech) and placed into a 37° C. 5% $CO_2$ incubator for a 30 minute gelation. After that, the 6 inserts were transferred into the cell culture hood. The gas permeable membrane was slightly peeled from each system to expose the reservoir into which the medium was added to an approximate height of 6 mm in 2 perfused system and 2 unperfused systems. The remaining 2 perfused system had the liquid level at the reservoir set to approximately 5 mm in height. This was because of the perfusion arrangement comprising a syringe pump having a pair of opposing syringes on a single drive such that 2 syringes infused medium into their respective insert systems (from 5 mm to 6 mm of liquid height in the reservoir), and 2 syringes withdrew medium form their respective insert systems (from 6 mm to 5 mm of liquid height in the reservoir) simultaneously. The pump was programmed to repetitively cycle the medium back and forth, such that at any time 2 reservoirs received medium and 2 reservoirs had their medium withdrawn. The medium was Neurobasal+2% B27+1% G5+0.5 mM Glutamax+1% Antibiotic/Antimycotic.

The 4 perfused reservoirs were interfaced to a syringe pump (KD Scientific Legato 270) as follows. First, 5 cm or shorter section of 0.04" ID softer tubing was attached to barbed connector built into the reservoir. The opposing end of the soft tube was then interfaced with barb to male luer-lock adapter (Qosina No. 11533). The male luer was then interfaced with female luer slip LuerTight™ fitting (Idex P-629) and connected to 1.5 m long section of FEP hard tubing (Idex No. 1548, 500 µm ID, $\frac{1}{16}^{th}$ inch OD). The hard tubing was routed through the rubber seal on the incubator door. This ensured uninterrupted flow when the door was closed. The opposing end of the FEP tubing was connected to another P-629 female luer slip and interfaced with male luer-lock BD syringe secured to the syringe pump. The short section of flexible tubing remained in the humidified incubator during the study. They were used to prevent stress on the reservoir during manipulations such as the insert system placement on the incubator shelf, i.e. the 12-well insert system did not move even when the hard tubes did during closing and opening of the incubator door.

All 6 insert systems were then placed into the 37° C. 5% $CO_2$ incubator for 7-day culturing. The flow rate was 94.5 µl/hour. In either direction, whether infusion or withdrawal, the target volume was 2.25 ml and the liquid level in the reservoir oscillated by 1 mm in z-direction. Under these conditions, in perfused inserts, the fluid level above the culture oscillated between 5 mm and 6 mm and was cycled up and down through the perfused cultures for 72 hours (3 days). Flow was programmed to reverse direction approximately once daily (every day).

Figure 11A:
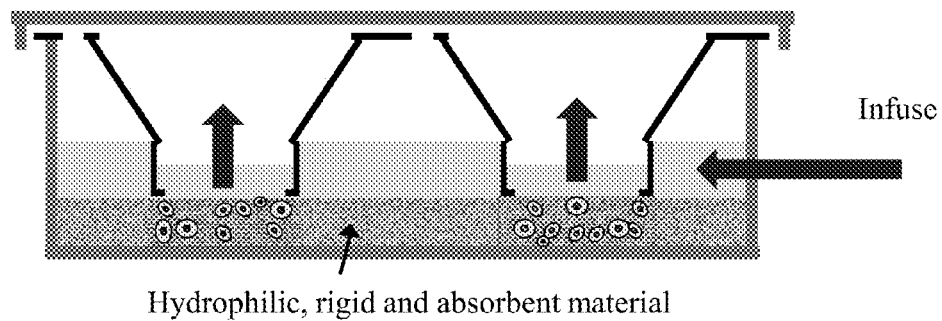
FIG. 11A depicts infusion stroke with flow directed up through the cultures.
Figure 11B:
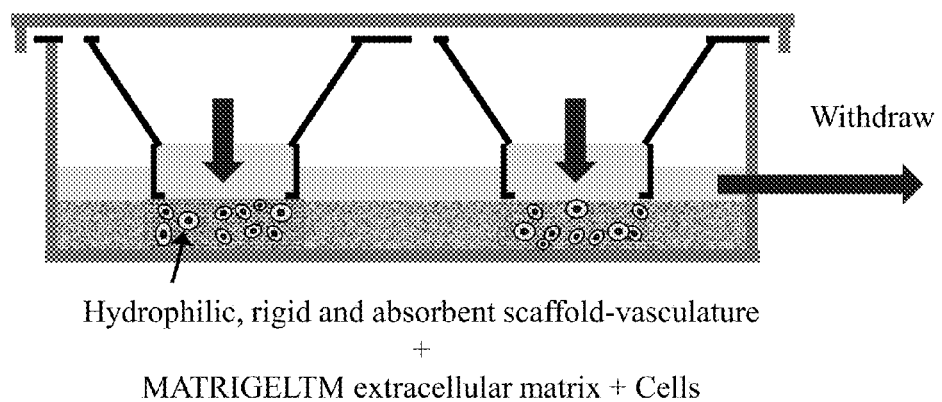
FIG. 11B shows withdrawal stroke with flow directed down through the cultures.

The schematic drawing of perfusion method and setup is shown in FIGS. 11A-11B. Only 2 wells are shown in a given row; however, there were 6 wells per row and only 3 wells per row had the 3D cultures. The medium was continuously pushed up through the cultures (FIG. 11A) for ~24 hours and then withdrawn for another 24 hours (FIG. 11B) at a rate which corresponded to approximately 2 culture volume exchanges per day; i.e. there were approximately 2 culture volume exchanges per stroke, whether up or down.

After 3 days of perfusion, at the end of the up/down stroke through the cultures, flow rate was increased to 10 culture volume exchanges per day. The medium continued to oscillate 1 mm up and down through the cultures and was reversed approximately 5 times daily for the next 96 hours (4 days). As no new media was added to the reservoir, it was thought that a higher rate more efficiently removed catabolites in an otherwise, maintenance-free automated perfusion.

(Automated perfusion provided stable culturing conditions by eliminating pipetting steps to change the medium which was known to cause abrupt fluctuations in culture conditions.)

Figure 12A:
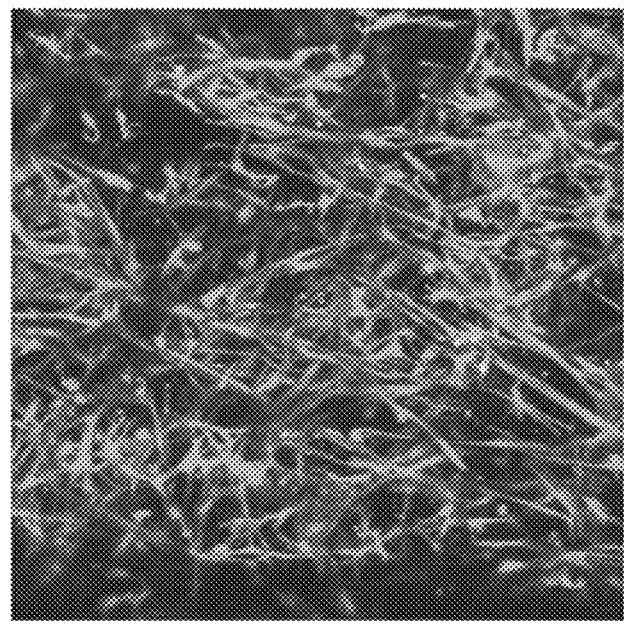
FIGS. 12A-12B are z-stacked micrographs projected onto a single plane for two representative 3D cell cultures, a 7-day perfused culture, and a 7-day matured but unperfused 3D culture control, respectively. The 3D cell cultures were cultured in MATRIGEL™ extracellular matrix and embedded in the uncoated rigid absorbent scaffold-vasculature. Perfused cultures were bi-directionally perfused intra-culture. The perfusion mode was medium recycling. In unperfused cultures, the medium was changed once in 7 days.
Figure 12B:
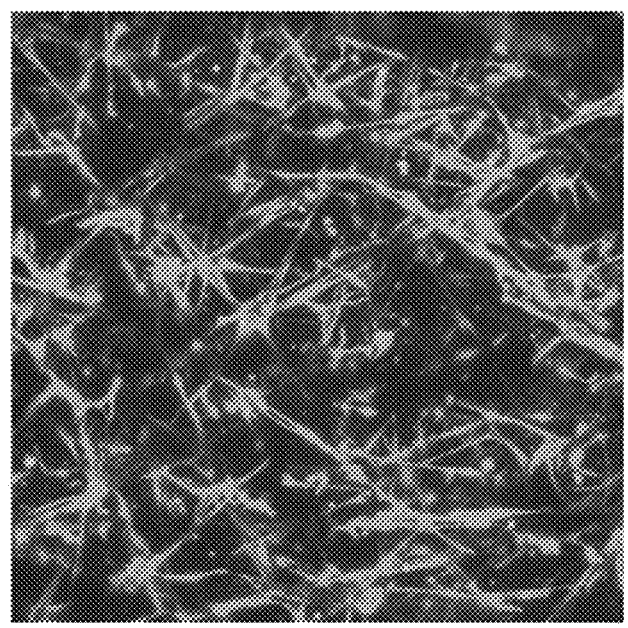
Figure 12C:
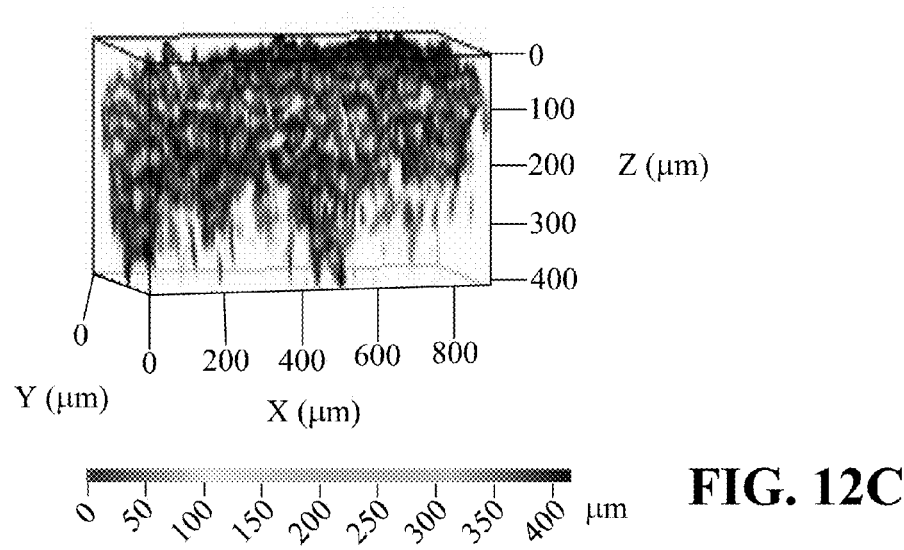
FIGS. 12C-12D are 3D renderings of z-stacked confocal micrographs acquired approximately every 20 µm through the 3D cultures through their full thicknesses. The 3D cultures shown in FIGS. 12C-12D correspond to cultures shown in FIGS. 12A-12B, respectively. The stacks were taken at 10×(x=898.24 µm, y=898.24 µm) using Zeiss LSM 510 confocal microscope.
Figure 12D:
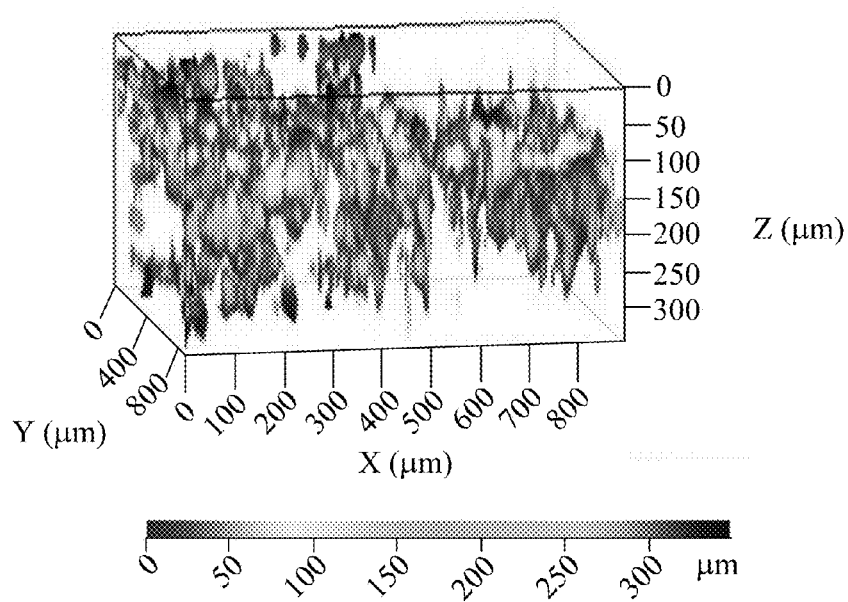

The cells were imaged after 7 days in a 3D culture using a confocal microscope (high-content live/dead assay). The cells were labeled by Calcein AM/Ethidium Homodimer-1 (Life Technologies # L-3224). FIGS. 12A-12B show z-stacked confocal micrographs (projected onto a single plane) of the Calcein AM intracellularly labeled live cells and EthD-1 labeled dead cell nuclei for representative perfused (FIG. 12A) and unperfused 3D cultures (FIG. 12B) in the uncoated G041 material, respectively. Z-stacked 3D renderings of said cultures are shown in FIGS. 12C-12D. In perfused 3D cultures (FIG. 12C) the live cell densities were higher and the cultures were healthier and thicker than unperfused controls (FIG. 12D). In unperfused 3D culture controls, the medium was changed once in 7 days as these cultures had plenty of medium in the reservoir; however, the mass transport in unperfused control cultures was limited solely to diffusion.

At a cell plating density of $5 \times 10^6$ cells/ml, it was expected that MATRIGEL™ 3D control cultures would degrade by day 7 without perfusion and synthetic intra-culture non-gel based absorbent scaffold-vasculature [Cullen, D. K., Vukasinovic, J., Glezer, A., LaPlaca M. C. 2007. J Neural Eng 4(2):159-172]. FIG. 12D shows that without perfusion 3D cultures thinned even in the presence of the absorbent scaffold-vasculature, demonstrating that perfusion intra-3D-culture was necessary to sustain these cultures healthy and maintain their thickness under said cell plating densities. The actual decay progress in the unperfused 3D control cultures was highly variable. Two out of three cultures survived well. One of the cultures that survived well is shown in FIG. 12B and FIG. 12D while the third culture exhibited a widespread decay. In contrast, the perfused 3D cultures were more consistent, healthier and thicker as shown in FIG. 12A and FIG. 12C.

Figure 13A:
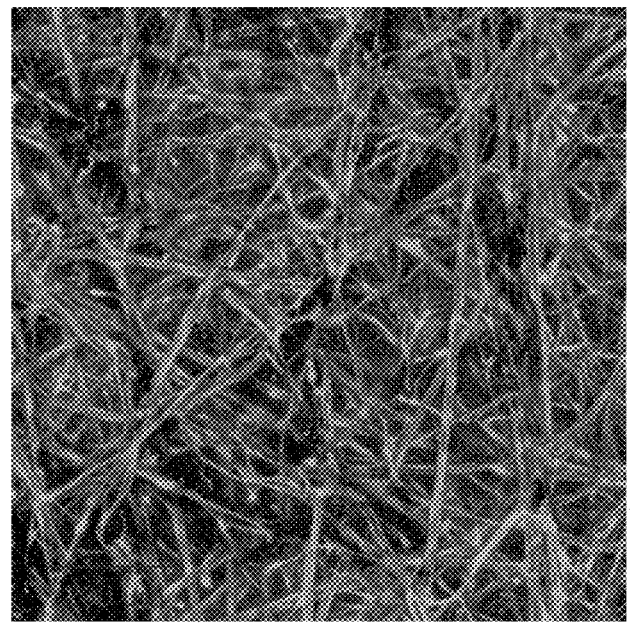
FIGS. 13A-13B are z-stacked micrographs projected onto a single plane for two representative 3D cultures, a 7-day perfused culture, and a 7-day matured but unperfused 3D control culture, respectively. The 3D cell cultures were cultured in MATRIGEL™ extracellular matrix and embedded in the PDL-coated rigid and absorbent scaffold-vasculature. Perfused cultures were bi-directionally perfused intra-culture. The perfusion mode was medium recycling. In unperfused cultures, the medium was changed once in 7 days.
Figure 13B:
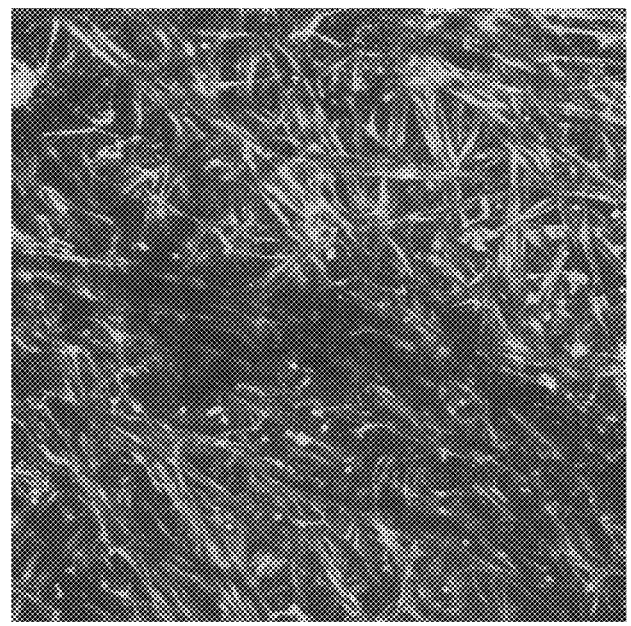
Figure 13C:
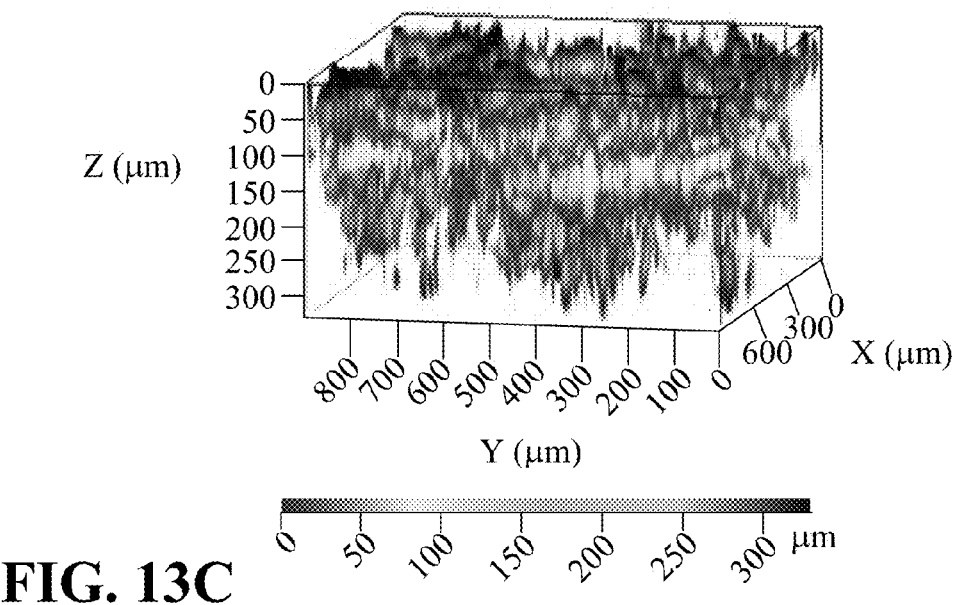
FIGS. 13C-13D are 3D renderings of z-stacked confocal micrographs acquired approximately every 20 µm through the 3D cultures through their full thicknesses. The 3D cultures shown in FIGS. 13C-13D correspond to cultures shown in FIGS. 13A-13B, respectively. The stacks were taken at 10× (x=898.24 µm, y=898.24 µm) using Zeiss LSM 510 confocal microscope.
Figure 13D:
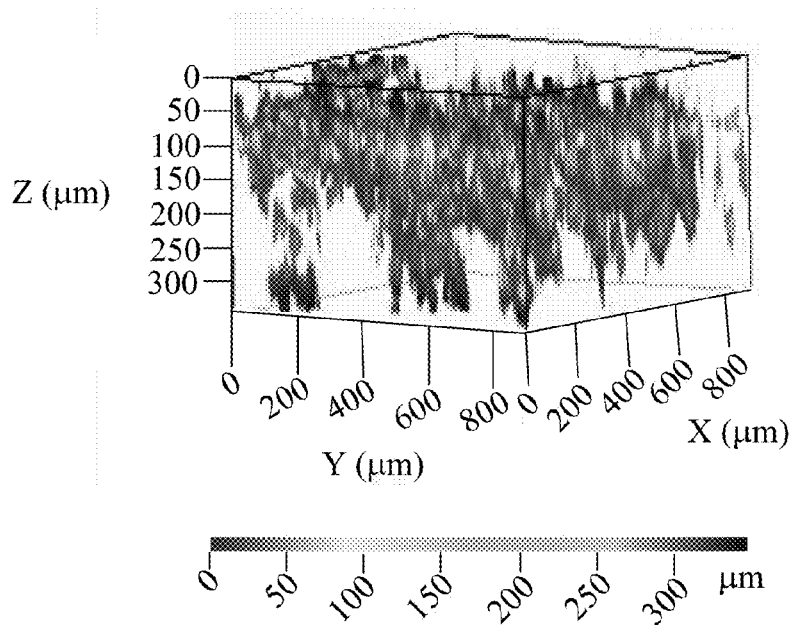

The above was further true for perfused and unperfused 3D cultures in PDL-coated absorbent scaffold-vasculature (FIGS. 13A-13D). Accordingly, the unperfused 3D cultures thinned down (FIG. 13D) and had lower cell densities (FIG. 13B and FIG. 13D) than did the corresponding perfused 3D cultures (FIG. 13A and FIG. 13C). This indicated that perfusion was necessary to meet the metabolic demands of these 3D cell cultures (FIG. 13B and FIG. 13D) despite the presence of PDL-coated absorbent scaffold-vasculature under hydrostatic and osmotic pressure differences.

Since the medium was completely replaced once in unperfused 3D cultures during a 7-day culturing period, and it was not changed but rather continuously recycled in all perfused 3D cell cultures and still the perfused 3D cultures were healthier, it was concluded that it was not the lack of extra-culture nutrient availability, but rather the lack of an efficient intra-3D-culture nutrient delivery and distribution method that caused lower survival and thinning of unperfused 3D culture controls. This demonstrated the superiority of intra-culture perfusion in delivering and distributing agents intra-3D-culture in both uncoated (FIGS. 12A-12D), and PDL-coated (FIGS. 13A-13D) scaffold-vasculature versus their respective unperfused (diffusion-limited) culture controls.

Figure 14A:
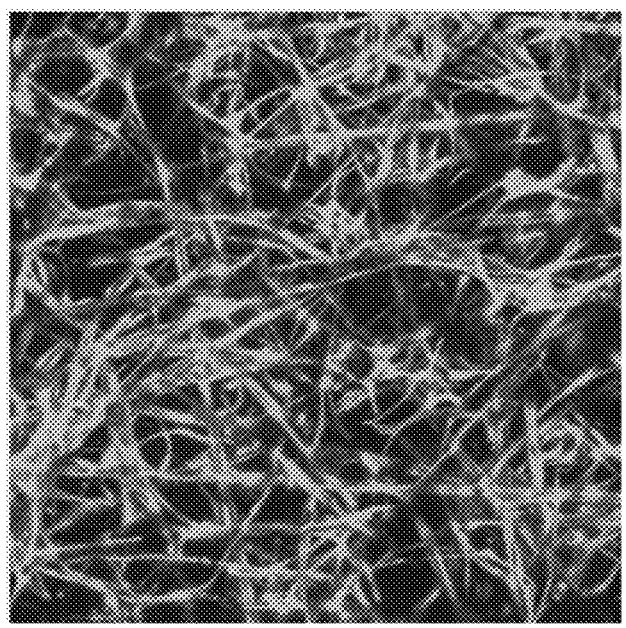
FIGS. 14A-14B are z-stacked confocal micrographs of said 3D cultures projected onto a single plane.
Figure 14B:
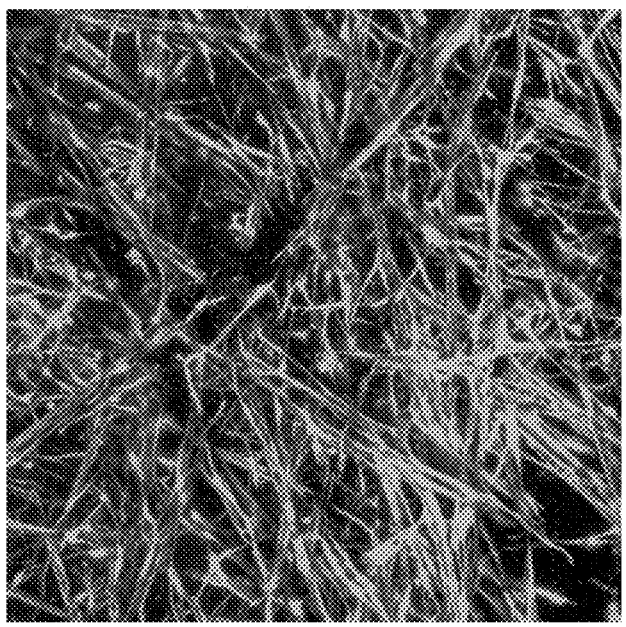
Figure 14C:
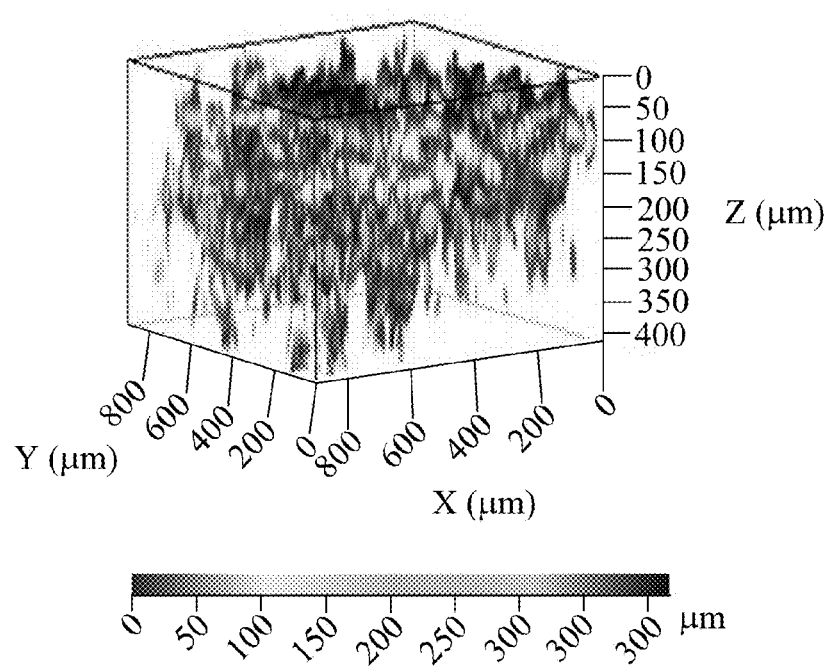
FIGS. 14C-14D are 3D renderings of z-stacked micrographs of said cultures acquired approximately every 20 µm through their full thicknesses. The cells in 3D cultures were cultured in MATRIGEL™ embedded in the rigid and absorbent scaffold-vasculature and bi-directionally perfused intra-3D- culture by recycling the medium. The images in a stack were taken at 10× (x=898.24 µm, y=898.24 µm) using Zeiss LSM 510 confocal microscope.
Figure 14D:
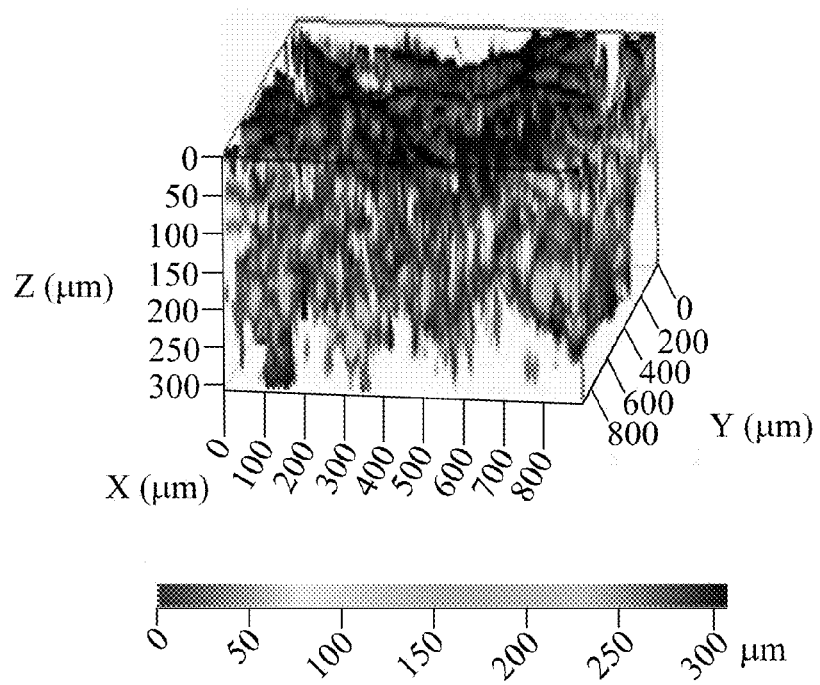

Further, cell survival and cell densities appeared consistently higher in PDL-coated versus uncoated scaffold-vasculature for both conditions, perfused and unperfused. Cell imaging in PDL-coated G041 material was more difficult in deeper layers of the 3D cultures than in uncoated material due to substantial cell growth and process development along the 3D network of fibers. Additional images of perfused 3D cultures in the uncoated (FIG. 14A and FIG. 14C) and PDL-coated scaffold vasculature (FIG. 14B and FIG. 14D) corroborate that the PDL-coated scaffold-vasculature provided higher functional benefit to the 3D cell cultures. It was thought that the combination of mass transport permeable and hydraulically conductive PVOH fibers and/or the PVOH coating on the glass fibers in conjunction with the PDL-coating which facilitated cell adhesion to said fibers, got the cells closer to the source of nutrients, which in turn helped them survive better.

The 3D cell culture perfusion study showed that perfusion improved cell survival and 3D cell culture thickness; thus, validating the intra-3D-culture perfusion method, perfusion tool comprising a perfused multiwell insert system, and the bi-directional cell culture perfusion method with medium recycling. The 3D cell cultures comprised one or more cells in a soft MATRIGEL™ scaffold anchored within the interior of an anchoring synthetic scaffold-vasculature, wherein the anchoring scaffold-vasculature was stiffer than was the gel, hydrophilic and comprised up to 10% per mass of the absorbent component in its composition.

Bi-directional perfusion worked on a principle of communicating vessels (FIG. 11). Raising medium level in the reservoir raised the medium level in the culture wells; lowering the medium level in the reservoir lowered the medium level in the culture wells. This was true so long as the intra-culture pressure drop was not too high; and it was made low by making the rigid scaffold act as artificial vasculature intra-gel either. The way by which the synthetic intra-culture vasculature worked was either by way of the absorbent mass transport permeable and hydraulically conductive fibers (more permeable and conductive than was MATRIGEL™) in the scaffold composition or by way of intra-culture capillary voids when the gel did not adhere sufficiently well to the scaffold, thus creating paths of lower resistance for the flow to pass intra-gel and a gel-based 3D cell culture. The former was validated in this Example with the cells in a 3D MATRIGEL™ cell culture and previously in the acellular MATRIGEL™ study in the Example 7. The latter was validated in the acellular MATRIGEL™ study in the Example 9.

Example 11

Perfused Multiwell Insert Systems, and Methods of Making, Using and Interfacing the Same in Sequestered and Non-Sequestered Perfused Culturing Conditions Bi-directionally perfused insert system (the exemplary system is shown in FIG. 4A-4C) for automated parallel feeding of tissue-like 3D cell cultures, and intra-culture drug delivery and distribution, was compatible with any pump. The medium could be delivered new (fresh) or recycled, more than one port was made per reservoir, ports between any of the reservoirs connected in any configuration, and a peristaltic pump, multichannel peristaltic pump, and one or more syringes in a syringe pump used to deliver medium to multiple reservoirs using a fluidic distributor/manifold (for example, 4-port or more luer stopcock manifolds, Qosina Part No. 17552, 17554, and 99876) with or without an arrangement of tees (for example, luer tees Qosina Part No. 80061, 80144, 88214, and 88215) and check valves (for example, Qosina Part No. 80107 and 80129).

Several made and tested exemplary configurations are shown schematically in FIGS. 15-17. FIG. 15 shows bi-directional perfusion arrangement with one fluidic port disposed per reservoir. In FIG. 15A the perfusion mode was medium recycling. In FIG. 15B the perfusion mode was fresh medium infuse/used medium withdraw. In the medium recycling mode (FIG. 15A) in one arrangement, the pump was a peristaltic pump which cyclically pumped the medium in and out of the reservoir (FIG. 15A (left)). In another arrangement, the pump was a syringe pump operated in a continuous push/pull infusion/withdrawal mode so as to cycle the medium in and out of the reservoir (FIG. 15A (right)). Multiple syringes in a syringe pump or multiple channels in a peristaltic pump could be used to drive one reservoir each without any tees. The reservoir was also made in a multiwell plate format (similar to the insert design but now with the wells which had bottom) and the same arrangements used to sequester cultures cultured in each well of the insert, wherein each well of the receiving multiwell plate acted as one reservoir with its own port. FIG. 15B shows bi-directional perfusion system in which fresh medium was injected into the reservoir during infusion stroke and used medium was withdrawn from the reservoir during withdrawal stroke. FIG. 15B (top) shows an arrangement comprising a peristaltic pump operated cyclically back and forth. The pump was connected to 2 bottles, the fresh medium bottle, and the used medium bottle, via tubing and a pair of check valves. During infusion stroke, fresh medium was drawn from the fresh medium bottle and delivered into the reservoir. During withdrawal stroke, the medium was drawn from the reservoir and dispensed into the used medium bottle. The same mode of operation but using a syringe pump is shown in FIG. 15B (bottom). The syringe pump was a KD Scientific Part No. Legato 270. The pump was setup with a pair of syringes such that both syringes were on the same side of the drive. Each syringe was connected to a tee with a pair of check valves for the flow from and to syringe. As shown schematically in FIG. 15B (bottom), during infusion stroke, Syringe 1 passed flow towards the reservoir through one tee leg. During withdrawal stroke, the Syringe 1 received medium from the fresh medium bottle connected to the other tee leg; this provided for continuous filling of the Syringe 1 which continuously provided for injection of the fresh medium into the reservoir. During withdrawal stroke, Syringe 2 was taking up the medium from the reservoir through one tee leg. During infusion stroke, Syringe 2 transferred the medium to the used medium bottle through the other tee leg; this provided for continuous discharge of spent medium from 3D cultures into the used medium bottle. The reservoirs were also made in a multiwell plate format such that each reservoir (well) had its own fluidic port which was fed via manifold (distributor or an arrangement of tees) on the side marked "To reservoir(s)" in FIG. 15B. This allowed to sequester cultures during perfusion such that each culture was seated in one insert well and had its own reservoir (well of the multiwell plate) with a dedicated perfusion port.

In the exemplary fluidic arrangements shown in FIG. 15 both the perfusion intra-culture was bi-directional and the flow through the reservoir was bi-directional, whether the medium was completely recycled or the fresh medium injected and the used medium withdrawn. Accordingly, this provided for a bi-directional perfusion tool with a bi-directional intra-culture perfusion. Still flow through the reservoir was also made unidirectional with bi-directional perfusion intra-culture; a unidirectional perfusion tool with bi-directional intra-culture. For example, FIG. 16 shows a bi-directional intra-culture perfusion with an inlet and one outlet fluidic port disposed in the reservoir enabling one-way flow through the reservoir. FIG. 16A shows bi-directional culture perfusion in which the flow through the reservoir was one-way but the medium was recycled. This arrangement was useful if different culture types were cultured in the wells, such that cell signaling molecules released by the one or more cultures upstream of any other culture were used as a conditioned medium for downstream cultures (with respect to direction of the one-way flow through the reservoir). FIG. 16B shows bi-directional cell culture perfusion in which the flow through the reservoir was one-way, with the fresh medium infused into the reservoir from the fresh medium bottle and the used medium (withdrawn from the reservoir) delivered into the used medium bottle in an exemplary setup in which the pump used was a peristaltic pump. In this arrangement, the same medium passed through the culture only once, but both ways, up and down intra-culture.

The disclosed exemplary, bi-directionally perfused culture methods were superior than uni-directional cell culture perfusion methods, because in the former the same medium had to pass intra-culture at least twice (up and down); thus, preserving presence of cell secreted molecules which were vital for normal cell and tissue function and were otherwise lost in one-way perfusion. Next, disclosed, tested exemplary setups showed that by controlling the external fluidic architecture it was possible to recycle the medium, replenish an amount of medium with the fresh medium continuously, or to exchange the medium by 50%-100% in every forward/reverse cycle. As G041 material scaffold-vasculature was absorbent, cultures would not dry even if the medium was completely withdrawn (100%) during every withdrawal cycle.

To sequester cultures in bi-directional intra-culture perfusion yet another system was developed and tested (FIG. 17). The key component of the system was a multiwell plate comprising shallow wells with a reservoir above the wells (FIG. 17C). The principle of operation is shown schematically in FIG. 17A-17B. The bi-directional, parallel perfusion of sequestered cell cultures was realized using an exemplary arrangement in a one-way flow through the reservoir, wherein the fresh medium was injected and used medium withdrawn. To prevent cross-well communication during perfusion each insert well was seated into its respective well in the multiwell plate. The flow was injected into the multiwell plate reservoir and then withdrawn from the multiwell plate reservoir cyclically in the same volume. To completely sequester cultures, the entire medium in the reservoir was withdrawn during withdrawal cycle; only the medium in the shallow wells seating respective insert wells remained in the multiwell plate. To sequester cultures, at least two ports were needed for perfusion, an inlet and an outlet port. To ensure that all medium was indeed withdrawn, the reservoir base was made at an angle to facilitate draining and to eliminate the well-to-well cross talk during filling and draining. The angle could have been made along any axis or axis combination (e.g. V- or otherwise shaped) which provided for that that all liquid be drained (except that in the wells) via the one exit port located at the lowest point of said inclination. The depth of each shallow culture well was identical; i.e. some wells protruded above the level of the reservoir base to ensure that all cultures had the same amount of medium at the end of withdrawal stroke as shown schematically in FIG. 16B. An exemplary 48-well plate comprising shallow wells with the reservoir above the wells is shown in FIG. 16C. It was made in glycol modified polyester material (PETG) using a mold and a vacuum former.

Next, the material into or onto which 3D cell cultures were plated (e.g. the absorbent 3D synthetic scaffold-vasculature, or any other porous hydrophilic material in any thickness or a plurality of said materials) could either be seated in the wells of the multiwell plate or built into the insert, wherein the porous material needed not contact the base of the plate wells. The methods by which said porous materials could be each separately attached or built into the wells of the insert were in part disclosed in the U.S. Provisional Patent Application Ser. No. 61/712,943 and in the U.S. patent application Ser. No. 13/962,403. An additional exemplary method, was a threaded connection between the threaded insert well and the insert well blind-cap-nut as shown in FIG. 17D. FIG. 17D shows left to right, a threaded blind well, porous material seated onto the rim of the blind well, the threaded blind-cap-nut, and the top and bottom view of the porous material sandwiched between the blind insert well and the blind cap, wherein both the insert well and the cap were threaded with matching male/female threads. Another exemplary method was a snap-fit method of sandwiching the porous materials between the insert well and its cap as shown in FIG. 17E. FIG. 17E shows from left to right, a blind well, a porous material disk, a blind cap, and the top and bottom view of the porous material sandwiched between the blind well and its cap via snap-fit method. The well caps were also formed as an integral insert blind well cap. That is, when an integral insert comprising one or plurality of blind wells was inserted and snap-fitted into another integral insert comprising one or plurality of matching blind wells (acting as caps), the porous materials seated within the integral insert blind well cap were sandwiched between the said two inserts.

As shown in FIGS. 17A-17B, the blind multiwell insert with the scaffold-vasculature seated either in the shallow wells of the multiwell plate or attached to the insert wells, enabled parallel automated perfusion of cultures which were sequestered during culturing. Next, by way of disclosed methods of attaching the porous materials to the insert wells, the spacing between the porous material and the bottom of the well plate seating the insert was adjustable, so long as the culture seated into the well insert was entirely submerged during perfusion. This design solution with no well-to-well cross-talk was realized without any microfluidic elements prone to clogging and failure. An exemplary external fluidic architecture used in this arrangement was a peristaltic pump, two bottles, stiff tubes, 2 tees, and 4 check valves.

In addition to structural design, cultures could be sequestered even if perfused in a shared reservoir using dimensional (flow and mass transport) analysis. In the arrangement shown in FIG. 16B diffusive length scales were made negligible relative to the respective convective length scales when the medium in the reservoir was displaced sufficiently fast in a one way flow, or when a constant one-way flow was superimposed on cyclic flow by way of two additional ports disposed in the opposing sides of the reservoir. In the latter arrangement, additional pump provided continuous one way flow through the reservoir to sequester cultures without injuries due to mass continuity. In essence, the constant one-way flow acted as a DC offset to an alternating bi-directional flow intra-cultures, or cyclic medium infusion and withdrawal from the reservoir, wherein the cultures only "felt" the bi-directional flow.

A simple length scale analysis worked as follows. First, it was assumed that a very small molecule which was easy to diffuse; and therefore, reach the neighboring culture was secreted by a culture. Next, it was assumed that such molecule had a diffusion coefficient equivalent to that of glucose in water ($D \sim 0.66 \times 10^{-9}$ $m^2/s$). Then it was calculated that diffusive path length of said molecule was approximately 1.5 mm in one hour. Next, it was assumed that the "DC" offset one-way uniform flow provided for full medium exchange in the reservoir in one hour. Then, assuming that the reservoir was an entire multiwell plate (width×length or approximately 86 mm×128 mm) with the inlet and outlet for the "DC" offset flow placed on two opposing sides of the plate and separated by 128 mm, and for a liquid level in the reservoir maintained constant at 5 mm, the "DC" offset flow rate was approximately 0.9 ml/min. At this flow rate the glucose molecule was advected by the one-way continuous flow 128 mm downstream from the well which "secreted" it; making it unlikely to reach the neighboring well or any other well for that matter as it was outside of the reservoir before making its 1.5 mm long diffusive path. In other words, by exchanging the medium in the reservoir once every hour by way of a superimposed uniform one-way flow through the reservoir eliminated culture cross talk based on length scale analysis.

For practical purposes, a method to control well-to-well cross talk while keeping the system straightforward to setup, without miniature fluidic components prone to clogging and failure in operation, and in the industry standard format was to use a simple dimensional analysis, and more specifically the Peclet number; a dimensionless number relevant in the study of transport phenomena in fluid flows. The Peclet number (Pe) is the ratio of the rate of advection of a physical quantity by the flow to the rate of diffusion of the same quantity driven by an appropriate gradient. For mass diffusion of molecules in the flow, the Peclet number was defined as length scale×velocity/mass diffusivity. Specifically, when the Pe=1, diffusive mass transport in the reservoir would have been considered at the same order of magnitude as the convective mass transport in the reservoir. For Pe>>1 the convective transport would dominate over diffusion, and for Pe<<1 the convection would have been considered negligible, with diffusion being the dominant mass transport mechanism. For a glucose molecule in the above described superimposed one way-flow through the reservoir measuring 128 mm×86 mm, with a liquid level of 5 mm at a flow rate of approximately 0.9 ml/min, the Peclet number was approximately Pe ~500 meaning that the diffusion was negligible relative to convection, well-to-well cross talk was considered insignificant, and cultures sequestered for practical purposes.

Fluidic components for all the systems shown were miniature, and easy to setup and interface. For the exemplary setup tested and shown in FIG. 15B2 they included miniature luer-lock check valves (permitting one way flow) such as Qosina part No. 11582, in combination with male-to-male or female-to-female luer lock connectors Qosina part No. 12090 and 17642, to connect to stiff FEP tubing with attached LuerTight™ connectors. For setup transfer or maintenance of sterile conditions after stopping the flow, the fluidic ports were closed using luer lock plugs female or male McMaster part No. 51525K372 and 51525K371, respectively. Except for check valves which were sterilized by 1-hour soaking in 70% Ethanol followed by 3× rinses in sterile DI water, all other components of the system including connectors, tube fittings, and tubes were autoclave steam sterilized in the Example 10 and in this Example.

The perfusion tool, comprising a perfused multiwell insert system provided for routine plating of cultures, and for ease of outgassing the system outside of the cultures on the start of flow via the vented ports in the inserts which also served for medium sampling. The intra-culture perfusion was achieved via hydrophilic or hydrophilic and absorbent anchoring scaffolds which also functioned as intra-culture vasculature. Bi-directional perfusion methodology served to prevent the loss of cell signaling molecules, while allowing at the same time the sampling of more concentrated cell secretions than in one-way flow intra-culture. Taken together, the perfusion tool comprising a standard format multiwell insert system; the intra-culture perfusion method in which the medium was forced to pass through the culture by way of an anchoring scaffold-vasculature; the intra-culture scaffold-vasculature which reduced pressure drop through an otherwise difficult to plate, handle and outgas 3D gel plugs comprising cells; and the bi-directional perfusion method which prevented loss of cell signaling molecules, provided for routine high-throughput plating, handling, perfusion and screening of engineered tissue reconstructions in an automated, maintenance free feeding regimen, for at least one week in culture. Finally, various perfusion modalities developed and tested showed that each culture can be perfused independently or dependent on other cultures, in situations where, for example, a culture is pre-conditioned with the medium from another culture in an automated fashion.

The exemplary insert systems were made using a mold and a vacuum former in the glycol modified polyester material (PETG, Polyethylene Terephtalate Glycol-modified). However, any material and any process known in the art can be used to make the insert system in large quantities with plurality of wells, such as injection molding. The scaffold-vasculature was either attached to the reservoir or to the insert wells using methods described here; however, any method known in the art including ultrasonic welding, thermal bonding, and other methods disclosed in the U.S. Provisional Patent Application Ser. No. 61/712,943 and U.S. patent application Ser. No. 13/962,403, among other methods, could be used.

For all exemplary disclosed perfusion platforms, the reservoir, the insert, and the lid could be made using any method known in the art allowing to fabricate the same in a mono-well or multiwell configuration of any footprint or well arrangement. It is also to be understood that fluidic ports could be disposed on any side of the reservoir; however, for practical purposes if the perfused system was to be imaged in operation, the preferred location of the ports was on the sides of the reservoir which were closest to being vertical. The ports could also be made by any method known in the art which provided for an opening, including piercing or puncturing the material.

It is to be understood that when scaffold/synthetic intra-culture vasculature was built-into the reservoir, the surface of the reservoir on which the scaffold/synthetic vasculature was attached or built into it could have been recessed down or protruded up from the interior surface of the reservoir base. It is also understood, that when the scaffold/synthetic intra-culture vasculature was built into the insert well, the distance between the bottom of the scaffold/synthetic vasculature from the interior surface of the reservoir under it was arbitrary for the perfusion system to function properly, so long as the cultures plated into the scaffold/synthetic intra-culture vasculature were submerged during perfusion. It is also understood that additional components could be added to the underside of the scaffold/synthetic intra-culture vasculature so long as these additional components did not hinder flow in bi-directional intra-culture perfusion. An exemplary component adhered to the underside of the scaffold/synthetic vasculature was a capillary PET membrane as was shown in the Example 6, wherein the scaffold/vasculature was adhered to the membrane of a commercially available insert by way of PDL coating. Other exemplary materials included thermally bonded or ultrasonically welded 0.22 μm filter membranes to prevent cross-well contamination and bacterial infection spread well-to-well; dialysis membranes for sampling of concentrated cell secretions, wherein said secretions were sampled above the scaffold/synthetic vasculature via the accessible top of the insert well; or another scaffold/synthetic vasculature seated onto another scaffold/vasculature, among other components and methods of adhering and attaching the same to the scaffold/vasculature.

Figure 18A:
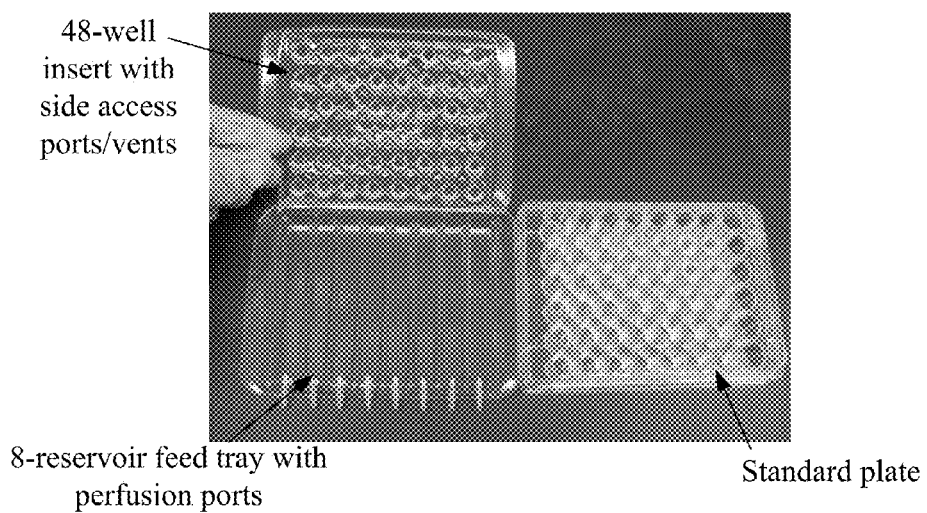
Figure 18B:
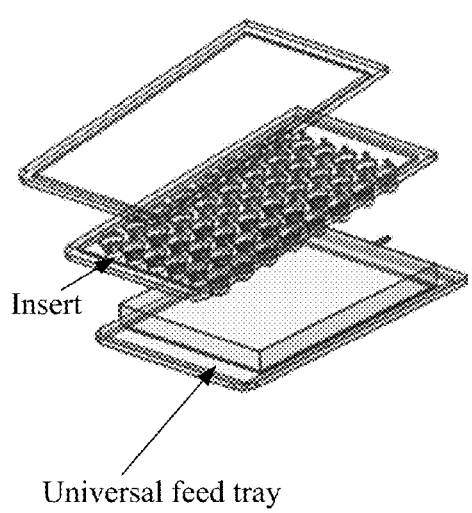
Figure 18C:
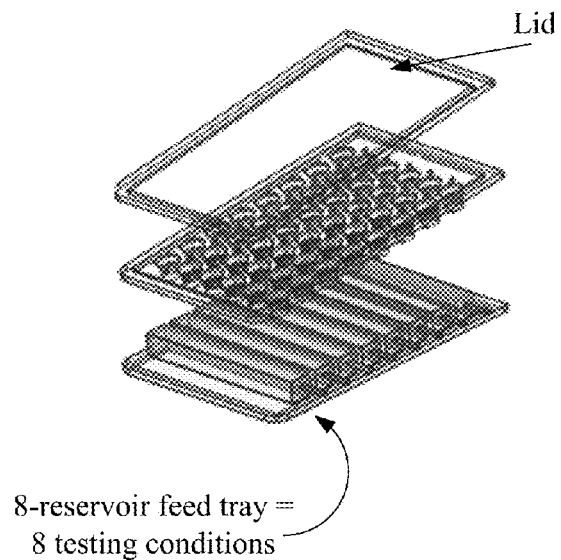
Figure 18D:
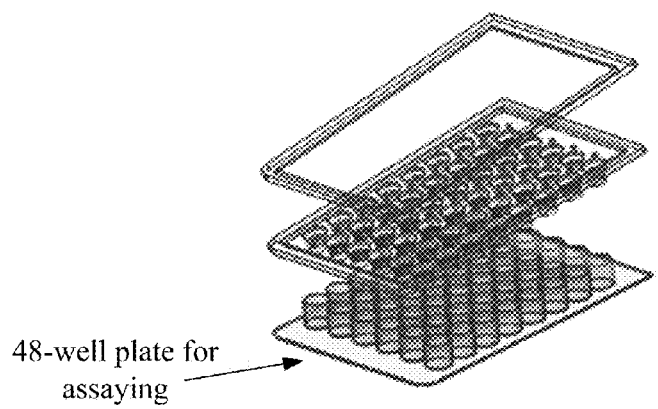

An exemplary, thermoformed 48-well perfused insert system comprising 8 perfused reservoirs (WITHOUT LID) is shown in FIG. 18A. FIG. 18A shows a schematic drawing of an exemplary 48-well insert system in which the scaffolds are built-into the insert wells, and shows an exemplary 48-well well insert as it was vacuum formed and after making the wells blind via a circular punch tool. The exemplary feed tray comprising 8 reservoirs with interfaced fluidic ports is shown next to a standard multiwell plate into which the insert comprising cultures was transferred to for assaying.

For cell culture perfusion prior to drug testing, including preconditioning, followed by drug testing in perfused or unperfused conditions, followed by assaying, followed by screening, various multiwell insert system arrangements were developed. An exemplary solution comprised a multiwell insert system whether perfused or unperfused, a perfused feed tray comprising one or more reservoirs or wells with a reservoir above the wells, a multiwell plate, and a lid.

An exemplary assay arrangement is shown in FIG. 18 for use with the insert system comprising an integral insert, universal feed tray, multi-reservoir feed tray, a multiwell plate and a lid. In this arrangement, cells and matrix were seeded into the insert wells for automated perfusion feeding in a universal feed tray for 1-2 weeks (FIG. 18B). Next, the insert was transferred into the 8-reservoir feed tray, and perfused with different drugs/concentrations; one per reservoir (FIG. 18C). Next, the insert was transferred to a standard 48 well plate for assaying individual cultures (FIG. 18D). In another arrangement, the universal feed tray was replaced with the multi-reservoir feed tray, and multi-reservoir feed tray replaced with perfused shallow-well multiwell plate.

All of the above arrangements demonstrated a method of making and using cell culture disposables in conjunction with 3-D cell culture scaffold and synthetic vasculature compositions and the intra-culture perfusion methods in high-throughput screening applications, high-content screening applications, and assay development.

Example 12

The Methods of Using Liquids of Different Densities as Pumping Fluids for Sequestered Bi-Directional Culture Perfusion in a Multiwell Plate and a Multiwell Insert Format, and the Methods of Making, Using and Interfacing the Same Two pumping fluids one of lower- (FIG. 19) and of higher density (FIG. 20) than was that of water and the exemplary culture medium (Neurobasal+2% B-27+1% G5+0.5 mM Glutamax) were tested each in sequestered 3D culture perfusion using acellular MATRIGEL™ 3D culture surrogates. During the process of selection of the pumping liquid, the following criteria were used—the pumping liquids had to be (1) non-toxic to the cells in culture, (2) immiscible or substantially immiscible in water and aqueous solutions as was the culture medium, and (3) remained separated from the cell culture medium during perfusion.

FIGS. 19A-19B show schematic drawings of the experimental arrangement used when the pumping fluid had a lower density than the culture medium. FIG. 19A shows the infusion stroke. FIG. 19B shows the withdrawal stroke. (To simplify the explanation, FIGS. 19A-19B assume infinitesimally small density difference between said liquids to demonstrate the principle of operation of communicating vessels, the insert wells and the wells of the shallow-well multiwell plate, communicating through the cultures residing in the insert wells.) The system was operated using a push/pull syringe pump (KDS Legato 270). The custom multiwell insert system comprised (1) a multiwell plate with plurality of shallow wells, a reservoir above the shallow wells, and a perfusion port disposed in the reservoir such that it was positioned above the top of the shallow wells; (2) an integral insert with plurality of blind wells and air vents (seated into an optional server-insert comprising matching blind wells and air vents); (3) hydrophilic synthetic scaffold-vasculature G041 material disks, wherein each disk was seated into and attached to the respective blind well of the non-server insert; and (4) the lid. Server insert served to eliminate the contact between non-server insert (the insert) comprising cultures and the pumping medium. In essence, it provided a double-wall for the inner insert wells. The air vents (a vent per insert well) served to vent air during perfusion, and sample the fluids, add them or remove them. The culture medium, drugs, test agents or other ingredients were typically added and sampled via the top-accessible insert well, by simply removing the lid.

The perfusion setup/assay preparation steps included (a) the plating of 8 mg/ml MATRIGEL™ 3D culture surrogates into the G041 material, (b) transfer of the setup to incubator for MATRIGEL™ gelation for 45 minutes, (c) the addition of cell culture medium into all insert wells and the respective wells of the shallow-well multiwell plate, followed by (d) the addition of the low density pumping medium (with the density lower than that of the culture medium) into the multiwell plate reservoir, and the (e) filling of syringes and tubes with said low density medium, prior to the start of perfusion. The exemplary candidate low-density pumping fluids were the non-toxic cooking oils, non-toxic mineral oils, non-toxic silicone oils and non-toxic liquids used in density gradient separation techniques, among others. The low-density pumping fluid tested was Bertolli extra virgin olive oil. The oil was not toxic, stayed separated above water when added to a beaker, and remained separated from the culture medium when delivered into the custom multiwell insert system.

In a low-density-pumping-fluid perfusion study, there was no cross-talk between culture media in different wells of the multiwell plate. That is, each well of the shallow well multiwell plate self-contained its respective medium. Accordingly, each well of the insert, and thus each culture was perfused by its own dedicated medium. This was realized by a specific multiwell plate design and perfusion conditions in which the interface between the low density pumping liquid and the culture medium was made to oscillate up and down such that (1) the interface between the liquids always remained in the wells of the multiwell plate and (2) the culture was always submerged in the medium. In this study, the delivered volume of the olive oil in infusion- and withdrawal stroke provided for a 2 mm rise and the respective 2 mm fall of the oil level (height) in the reservoir. The flow rate used provided that the oil-to-air interface moved up and down by 2 mm in each direction 20 times in 24 hours. During a 24-hour study, it was seen that the culture-medium-to-air interface oscillated synchronously. That is, the insert wells and the multiwell plate functioned as communicating vessels which were connected via the hydraulically conductive synthetic intra-culture vasculature. At such, relatively slow changes of the pumping fluid level in the plate reservoir, the pumping fluid and the culture medium remained separated during perfusion which was easy to visualize owing to Phenol Red in the medium and yellowish color of the olive oil pumping fluid. Under hydrostatic condition (when the flow was stopped) the oil-to-air interface in the multiwell plate reservoir was at a higher elevation than the culture-medium-to-air interface in the insert, because the multiwell plate had a lower density pumping liquid above the culture medium, whereas the insert did not. Without the culture and in a hydrostatic equilibrium, as shown in FIG. 19C, the hydrostatic pressure balance was given by $$p_a + \rho_1 * g * h_1 = p_a + \rho_2 * g * h_2 + \rho_1 * g * h, \quad \text{Eq. 1,}$$

where $p_a$ was the atmospheric pressure, $h_1$ was the height of the column of culture medium in the insert measured from the bottom of the well of the multiwell plate, $h_2$ was the height of the column of low density pumping liquid measured from the interface with the culture medium to the air interface, h was the height of the column of the culture medium in the well plate measured from the bottom of the well in the well plate, and $\rho_1$ and $\rho_2$ were the respective densities of the culture medium and the low density pumping fluid. Accordingly, the height of the column of the culture medium in the insert, $h_1$, measured from the bottom of the well of the multiwell plate was given by $$h_1 = h + h_2 * \rho_2 / \rho_1. \quad \text{Eq. 2,}$$

Hence, the total liquid height in the reservoir, or the elevation of air-to-liquid interface in the reservoir was greater than that in the insert as given by $$h_2 + h - h_1 = (1 - \rho_2/\rho) * h_2. \quad \text{Eq. 3,}$$

In perfusion, MATRIGEL 3D culture models appeared to have posed negligible resistance to fluid flow and slow rates of flow driven by a stepper pump motor provided for quasi static operation in which the Equation 2 was applicable. Accordingly, this provided for a method to control the flow rate and the volume exchange rate in intra-culture perfusion by controlling the injection volume and the rate of flow of a low density pumping liquid. Specifically, the height of the column of culture medium in the insert could be calculated by $$h_1 = 4 * V_1/(\pi * D^2) + h_2 * (\rho_2/\rho_1) * (D^2 - d^2)/D^2, \quad \text{Eq. 4,}$$

where $V_1$ was the volume of the culture medium, D was the diameter of the well of the multiwell plate, and d was the diameter of the insert well, where $V_1$ was given by $$V_1 = h * (D^2) * \pi/4 + (h_1 - h) * (d^2) * \pi/4. \quad \text{Eq. 5,}$$

Since the terms $(D^2 - d^2)/D^2$ and $\rho_2/\rho_1$ were each less than 1, the vertical displacement of the culture-medium-to-air interface in the insert was always smaller than that of the pumping liquid-to-air interface. However in the conducted experiment, the insert well diameter was much smaller than that of the well of the multiwell plate. Further, the ratio of the olive oil to culture medium density was approximately 0.8-0.92. Accordingly, a 2 mm vertical displacement of the low density pumping fluid in the reservoir produced approximately 1.5-1.8 mm vertical displacement of the culture medium in the insert well. Hence, in this study, the approximate number of culture volume exchanges per day was 120-144, as the thickness of MATRIGEL™ model 3D cultures was approximately 500 μm.

The applied flow rate was one to two orders of magnitude higher than in Example 10 where 3D brain cultures in MATRIGEL™ in G041 material survived in a one week study at 2-10 culture volume exchanged per day. This showed that sequestered 3D culture perfusion can be done even at high rates of flow, much higher than was that necessary to sustain brain 3D cell cultures in MATRIGEL™ extracellular matrix plug, yet the fluids remained separated and the medium in the insert well oscillated up and down. Next, the disclosed design enabled not only to bi-directionally perfuse sequestered cultures but also to perfuse said cultures by recycling their dedicated medium. This was significant because said medium contained cell secreted signaling molecules (e.g trophic factors) necessary for normal cell and cell-network function. These molecules are normally lost with the flow in one-way cell culture perfusion.

During perfusion MATRIGEL™ model 3D cultures were accessible from the top of the insert well, and the medium was sampled, new medium added, and the medium partly changed without removing the insert from the plate. Drugs or other molecules could also be added, medium exchanged, and the perfusate comprising concentrated cell metabolites/catabolites (due to medium recycling) sampled controllably, and the process of sampling and additions automated owing to microtiter plate footprint. The disclosed setup further enabled the in situ culture imaging during perfusion. Next, to improve the imaging resolution by keeping the cultures as close as possible to the bottom of the multiwell plate, another design was made. In this design, which was also compliant with the low-density-pumping-medium culture perfusion (FIGS. 19A-19B), the G041 material disks were first seated into the wells of the shallow-well multiwell plate. Next, an integral was made and used to sandwich each disk between the blind insert well and the respective well in a shallow-well multiwell plate. This enabled high resolution imaging of the 3D cultures embedded into G041 material during, before or after perfusion, because the bottom of the culture was adhered to the bottom of the well of the custom multiwell plate and close to the objective lens. Next, by way of the custom thermoforming approach the thickness of the bottom of the multiwell plate was adjustable by using thinner starting materials, e.g. 0.03-0.04 inch think sheets, which made the well base thinner than in standard microtiter (multiwell) plates.

FIGS. 20A-20B show infusion and withdrawal stroke, respectively, in experimental arrangement for sequestered 3D culture perfusion with high-density pumping fluid. To simplify the explanation, FIGS. 20A-20B assume infinitesimally small density difference between said liquids to demonstrate the principle of operation of communicating vessels (the insert wells and the reservoir) communicating through the cultures residing in the insert wells. The system was operated using the push/pull syringe pump (KDS Legato 270). The custom multiwell insert system comprised (1) a reservoir with one perfusion port; (2) an integral insert with plurality of blind wells and air vents (an optional server insert, not shown); (3) hydrophilic synthetic vasculature disks (G041 material), wherein each disk was attached to the respective blind well via the threaded connection between the threaded insert well and the insert well blind-cap-nut (see FIG. 17D); and (4) the lid. The insert was made from an integral plastic sheet in which the well openings and vents were made by a plastic cutter, followed by insertion and silicone-sealing of the blind wells (FIG. 17D) to the sheet. During perfusion, the culture medium, drugs, test agents or other ingredients were added and sampled via the top-accessible insert wells, by simply removing the lid.

The perfusion setup/assay preparation steps included (a) the plating of 8 mg/ml MATRIGEL™ 3D culture surrogates into the G041 material, (b) transfer of the setup to incubator for MATRIGEL™ gelation for 45 minutes, (c) addition of the high density pumping medium (with the density higher than was that of the cell culture medium until the height of pumping liquid in the reservoir and the insert was 1 mm below the culture, (d) the addition of cell culture medium into all insert wells, followed by (e) filling of syringes and tubes with said high density medium, prior to the start of perfusion. In the event that a gas bubble was trapped between the liquids in the insert, the pumping fluid was drawn down, the insert pushed back and forth in the horizontal plane until the air bubble was able to move into the reservoir, and then withdrawn volume of the pumping fluid replenished.

The exemplary candidate high-density pumping fluids were non-toxic fluorocarbon (perfluorinated) fluids used in liquid ventilation (liquid breathing) and blood substitution (e.g. Perfluorodecalin used in artificial blood products), non-toxic barium sulfate suspensions (e.g. those used in CT scans of the gastrointestinal region) and non-toxic fluids used in density gradient separation techniques (e.g. Fluorinert FC-40 or FC-70), among others. Perfluorodecalin (and other fluorocarbons) provided for a convenient all-in-one solution for (a) good culture gas exchange owing to high gas solubility, (b) relatively high-density suitable for use as the pumping liquid herein, and (c) deep imaging access owing to low refractive index (lower than that of water).

First, Perfluorodecalin (Sigma Aldrich # P9900) was tested as the high density pumping liquid in a 24-hour perfusion study (FIGS. 20A-20B). At the start of perfusion, Perfluorodecalin was first withdrawn (FIG. 20B). Throughout the perfusion there was no cross-talk between cultures residing in different insert wells and each culture was perfused in its own medium. This was realized by a specific multiwell insert system design and perfusion conditions in which the interface between the high density pumping liquid and the culture medium remained in the insert, and was always below the culture (throughout perfusion). In this study, the delivered volume of Perfluorodecalin in infusion- and withdrawal stroke provided for a 2 mm rise and the respective 2 mm fall of its level in the reservoir. The flow rate used provided that this level moved up and down by 2 mm in each direction 4 times per hour.

During a 24-hour study, it was seen that the level of Perfluorodecalin column in the reservoir and that of the culture medium in the insert wells oscillated synchronously. That is, the insert wells and the reservoir functioned as communicating vessels which were connected via the hydraulically conductive synthetic intra-culture vasculature. At such, relatively slow oscillations of the liquid levels, the immiscible pumping fluid and the culture medium remained separated during perfusion. That is, in each insert well, clear Perfluorodecalin was always below the culture medium containing Phenol Red. Next, it was also seen that a vertical 2 mm displacement of Perfluorodecalin in the reservoir produced approximately 2 mm vertical displacement in the culture-medium-to-air interface in the insert well. Further, when perfusion was stopped, it was seen that the total liquid height in the insert, or the culture-medium-to air interface was above the Perfluorodecalin-to-air interface in the reservoir. This was because the lighter, culture medium was present in the insert and not present in the reservoir. Without the cultures and in hydrostatic conditions, the liquid levels in the insert and the reservoir correspond to those shown in FIG. 20C.

Based on a hydrostatic pressure balance, the height of the liquid-to-liquid interface (Perfluorodecalin-to-culture-medium) in the insert, h, measured from the bottom of the reservoir was given by $$h=h_2-h_1*\rho_1/\rho_2,\qquad\text{Eq. 6,}$$

where $h_2$ was the height of the column of the pumping fluid in the reservoir measured from the bottom of the reservoir, $h_1$ was the height of the column of the culture medium measured from the interface with the pumping fluid in the insert, and $\rho_1$ and $\rho_2$ were respective densities of the culture medium and the high density pumping fluid. Accordingly, the total liquid height in the insert was greater than that in the reservoir as given by the $$h_1+h-h_2=(1-\rho_1/\rho_2)*h_1.\qquad\text{Eq. 7,}$$

In perfusion, MATRIGEL 3D culture models appeared to have posed negligible resistance to fluid flow and slow rates of flow driven by a stepper pump motor provided for quasi static operation in which the Equation 6 was applicable. Accordingly, this provided for a method to control the flow rate and the volume exchange rate in intra-culture perfusion by controlling the injection volume and the rate of flow of a high density pumping liquid. Specifically, the height of air-to-culture-medium interface in the insert well, measured from the bottom of the reservoir, could be calculated by $$h+h_1=h_2+(1-\rho_1/\rho_2)*h_1.\qquad\text{Eq. 8,}$$

Accordingly, the height of air-to-culture-medium interface in the insert was proportional to the height of the pumping-fluid-to-air interface in the reservoir by a factor of 1. Thus, the 2 mm vertical displacement in Perfluorodecalin-to-air interface in the reservoir produced the 2 mm vertical displacement in the culture-medium-to-air interface in the insert, as observed visually. Accordingly, in this perfusion study, the intra-culture exchange rate was approximately 8 MATRIGEL™ 3D culture surrogate volume exchanges per hour or approximately 192 volume exchanges per day. Next, in yet another design variation, the perfused reservoir was substituted by a shallow-well multiwell plate with the reservoir above the plate wells, with the same result observed.

Next, another high-density pumping liquid was tested. This liquid was miscible with aqueous solutions. However, it was still used to show that even miscible fluids could be made isotonic and as such used as pumping liquid in sequestered cell culture perfusion. To do so, Percoll (Sigma Aldrich #P4937, cell culture grade, density 1.13 g/cm$^3$) was first made isotonic by adding 9 parts (v/v) Percoll to 1 part (v/v) 10×HBSS and as such used as the pumping fluid. During a 2-hour study, in which the cell culture medium was replaced by Hank's Balanced Salt Solution (HBSS), the HBSS level in the insert was made to move up and down by 2 mm in each direction once per hour. (Note that 9 parts (v/v) Percoll to 1 part (v/v) 10× concentrated cell culture medium was also suitable, if culture medium was perfused not HBSS intra-culture).

The disclosed density-gradient driven perfused systems provided for sequestered bi-directional perfusion of MATRIGEL™ 3D culture surrogates in a multiwell plate and multiwell insert format. It is to be understood, that for all cell culture perfusion Examples disclosed herein, cells needed not be seeded in a gelling MATRIGEL™ and then perfused. Instead, 3D cell cultures were previously seeded in gelling and non-gelling extracellular matrix materials into a rigid scaffold-vasculature, or seeded without the gel in the uncoated or coated rigid and absorbent scaffolds such as those disclosed in U.S. Provisional Patent Application Ser. No. 61/712,943 and the U.S. patent application Ser. No. 13/962,403. Further cells seeded into said materials were also cell aggregates such as 3D cell spheroids, or cells seeded in any suspension which could be wicked by said materials as disclosed in the U.S. patent application Ser. No. 13/962,403.

For cells embedded in flow permeable hydrophilic scaffolds (wherein the scaffolds were permeable to fluid flow via either 3D-connected intra-scaffold void volume which extended to at least two opposing surfaces of the scaffold, or the mass transport permeable and hydraulically conductive 3D network of the absorbent material in the scaffold composition, or both) without gel, the disclosed methods of sequestered and non-sequestered 3D culture perfusion were applicable so long as the pressure drop through cultures was not too high and the liquid level made to oscillate up and down through the cultures. For example, without gelled MATRIGEL™ "plugs", the pressure drop intra-3D-culture (embedded in the hydrophilic scaffold) reduced. This facilitated perfusion and reduced normal and shear stresses experienced by the cells in a 3D culture. However, even for gel-based 3D cultures, imperfections in gel adhesion to the scaffold created 3D-distributed intra-culture pumping network (see Example 9), or the addition of hydraulically conductive and mass transport permeable constituent in the scaffold composition enabled intra-culture perfusion (Example 7) which was non-invasive even to brain cells embedded in the gel plug, resulting in improved cell survival (Example 10) relative to unperfused gel cultures. This was validated with MATRIGEL™ extracellular matrix gel which was known to partition solutes [Fissell, W. H, Hofmann, C. L., Ferrell, N. et al. 2009. Am J Physiol Renal Physiol 297(4):F1092-F1100], was less permeable to mass transport than certain cell layers [Marasanapalle, V., Li, X., Polin, L., et al. 2006. Invest New Drugs 24(2):111-116], and known to generate relatively high resistance to fluid flow [McCarty, W. J. and Johnson, M. 2007. Biorheology 44(5-6):303-317]. Accordingly, by showing that difficult to perfuse 3D gel-based cell cultures (intra-MATRIGEL™ perfusion) were perfused in parallel, and perfused successfully, served to corroborate the utility of the disclosed perfusion methods, perfusion platforms and the methods of making and using the same, in the disclosed and other easier-to-operate 3D cell culture perfusion conditions; for example, in perfusion of 3D cultures without the gel. In all these examples, the hydrophilic scaffold in which cells were embedded served to facilitate intra-3D-culture perfusion and functioned as synthetic intra-culture vasculature.

It is to be understood, that perfused cells needed not be cells in a 3D culture but any cells, any other material, or any other material with cells, placed above, below, embedded or suspended in the hydrophilic scaffold; or any cells, any other material, or any other material with cells, placed above, below, between, embedded or suspended in some or all hydrophilic scaffolds in a scaffold stack wherein the scaffolds in a stack were hydrophilic but generally different.

In the Examples presented herein, the disclosed methods of bi-directional cell culture perfusion solved the majority of problems associated with cell culture perfusion, whether 3D culture perfusion or 2D culture perfusion. In general, available microfluidic systems with microchannels and miniature components were prone to failure due to bio-fouling (non-specific adhesion to the interior of small channels), problems with outgassing, cumbersome protocols with respect to culture plating and system priming, and the logistics of maintaining equal perfusion conditions in all wells.

Specifically, in prior art microfluidic systems, when cultures were fed from the common source, the variations in culture health produced variations in flow rates that were feeding wells. In a microfluidic network this led to increased flow rates to those wells where cultures decayed, thinned down, or adhered poorly (low resistance to flow); while drying healthy cultures that posed higher resistance to flow. This required devising a high pressure drop source (one per culture well) placed in series with each culture well, to ensure mass-equilibrated flow to all wells. While these strategies could be successful in providing relatively constant flow rates to all cultures, these pressure drop generating components posed sealing risk in application and generated high values of normal stress. In contrast, the perfusion system designs and perfusion methodologies disclosed herein, did not use any high pressure drop generating components to maintain equal flow in culture wells, and did not use any miniature components prone to clogging in operation. Instead, the designs focused on minimizing pressure drop through the 3D cultures with sequestered yet nominally equal 3D culture well perfusion maintained by way of a specific 3D culture well design and flow configuration, density gradient perfusion approach etc. The second problem of perfusion systems in a multiwell plate format is the air outgassing in the microfluidic network when the flow is started.

Accordingly, venting air in prior art microchannel-based systems required a bubble trap, one per each channel. Unfortunately, in case of gel-based 3D cultures, after the culture is plated, an air bubble was inevitably trapped. This bubble was then either forced through the culture on the start of flow or it hindered (obstructed or partially blocked) the flow towards the culture. Hence, gel-based 3D cultures were typically injured by forcing the bubble into the culture during perfusion, or exposed to high-pressure surges when the bubble otherwise burst followed by sudden uncontrollably high rates of flow. In contrast, in the disclosed designs, air was vented through the respective vent ports without disturbing the cultures. Accordingly, the disclosed designs did not have problems with bio-fouling, outgassing and pressure surges during system priming/venting or clogging in operation. Finally, the disclosed methods of bi-directional perfusion responded, for the first time, to critical user requirements with respect to concentration of cell generated signaling molecules in perfused cultures in a multiwell plate and multiwell insert format. (For example, even when the medium was recycled in one-directional perfusion, there would be a time-delay in which it could be sent back to the same culture it was collected from. In contrast, in bi-directional perfusion that same culture medium was there for the culture and simply cycled up and down.) By recycling the medium, bi-directional perfusion prevented loss of trophic factors, autocrine and paracrine signaling molecules cells secrete to regulate their environment, growth and many other functions. Further, medium cycling up and down through respective cultures, enabled further to sample more concentrated cell secretions from the cultures; thus, saving time and money on concentrating and processing medium later. Next, in sequestered 3D culture perfusion, different cultures could be perfused, mimicking for example, organs in the human body, or the cultures could be incompletely sequestered enabling for example slow flow of liver metabolites to a brain 3D culture (see FIGS. 17A-17B; under suitable flow rate). Accordingly, without microchannels to clog, complicated designs, cumbersome system priming and setup protocols, the disclosed perfusion systems and the disclosed perfusion methodologies enabled successful parallel perfusion of gel-based 3D cell cultures bi-directionally that could not be achieved using any other method or tool known or available in the art.

The invention claimed is:

1. A method of culturing cells, comprising providing the cells, and culturing each of the cells in a plurality of liquids, wherein the liquids are of a different density and two or more of the plurality of liquids form separate air-liquid interfaces.

2. The method of claim 1, wherein the plurality of liquids are immiscible.

3. The method of claim 1, wherein the plurality of liquids include a cell culture medium and perfluorodecalin.

4. The method of claim 1, wherein the cells are cell aggregates or spheroids.

5. The method of claim 1, wherein the cells are in a sol-state suspension and are placed in a hydraulically conductive scaffold.

6. The method of claim 5, wherein the hydraulically conductive scaffold has a void volume of between approximately 60% and 95%, and comprises between approximately 70% and 95% w/w insoluble borosilicate glass fibers having an absorbent polymer coating.

7. The method of claim 6, wherein the hydraulically conductive scaffold further comprises an absorbent material which extends to all surfaces of the scaffold.

8. The method of claim 6, wherein the absorbent polymer coating is polyvinyl alcohol.

9. The method of claim 5, wherein the hydraulically conductive scaffold is coated with a cell-adhesive coating or a non-cell adhesive coating.

10. The method of claim 1, wherein the cells are cultured in a housing for use in cell culture experiments, wherein the housing comprises a plate, a well insert, and a lid, and wherein
   a. the plate comprises sides and a bottom which form a plate reservoir,
   b. the well insert comprises one or more air openings and a plurality of insert wells configured to contain a cell culture, wherein each insert well has an open top portion, an open bottom portion, and a hydraulically conductive three dimensional scaffold disposed in between,
   c. the well insert is disposed within the plate reservoir,
   d. a first liquid is added to the insert wells containing cells, and
   e. a second liquid is added to the plate reservoir.

11. The method of claim 10, wherein the plate reservoir comprises
   a. a plurality of large wells configured to contain a cell culture, each large well having a height lower than the plate sides, and
   b. wherein each of the plurality of insert wells is smaller in width and depth and greater in height than the corresponding large well that it fits within.

12. The method of claim 11, wherein the first liquid has a higher density than the second liquid.

13. The method of claim 10, wherein the first liquid has a lower density than the second liquid.

14. The method of claim 13, wherein the first liquid is a cell culture medium and the second liquid is perfluorodecalin.

15. The method of claim 10, further comprising adding the cells in a sol-state suspension to the each hydraulically conductive scaffold.

16. The method of claim 15, wherein the sol-state suspension is a sol-state composition comprising Laminin, Collagen IV, Entactin, and heparin sulfate proteoglycan.

17. The method of claim 10, wherein the plate further comprises at least one perfusion port and the second liquid is injected and then withdrawn via the at least one perfusion port.

18. The method of claim 17, wherein the plate comprises an inlet port and an outlet port, each disposed on opposite sides of the plate, and the second liquid is injected via the inlet and withdrawn via the outlet.

19. The method of claim 18, wherein the process of the second liquid injection and withdrawal is repeated.

20. The method of claim 19, wherein a continuous flow of the second liquid is further superimposed by way of an additional inlet and outlet perfusion port disposed in the opposing sides of the plate.

21. The method of claim 19, wherein the injected liquid volume is the volume of the injected liquid which was not in the plate prior to injection.

\* \* \* \* \*